(12) United States Patent
Ferro, Jr. et al.

(10) Patent No.: US 11,929,168 B2
(45) Date of Patent: *Mar. 12, 2024

(54) SYSTEMS, DEVICES, AND METHODS FOR DIAGNOSTIC AID KIT APPARATUS

(71) Applicant: EMED LABS, LLC, Miami, FL (US)

(72) Inventors: Michael W. Ferro, Jr., Palm Beach, FL (US); Colman Thomas Bryant, Fort Lauderdale, FL (US); Sam Miller, Hollywood, FL (US); Zachary Carl Nienstedt, Wilton Manors, FL (US); Marco Magistri, Miami, FL (US); John Ray Permenter, Miami, FL (US)

(73) Assignee: EMED LABS, LLC, Miama, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/645,223

(22) Filed: Dec. 20, 2021

(65) Prior Publication Data

US 2022/0375596 A1    Nov. 24, 2022

Related U.S. Application Data

(63) Continuation of application No. 17/514,891, filed on Oct. 29, 2021, now Pat. No. 11,369,454, and a (Continued)

(51) Int. Cl.
  *G16H 40/67* (2018.01)
  *G16H 20/10* (2018.01)
  *G16H 80/00* (2018.01)

(52) U.S. Cl.
  CPC ............. *G16H 40/67* (2018.01); *G16H 20/10* (2018.01); *G16H 80/00* (2018.01)

(58) Field of Classification Search
None
See application file for complete search history.

(56) References Cited

U.S. PATENT DOCUMENTS

| 7,110,525 B1 | 9/2006 | Heller et al. |
| 7,176,936 B2 | 2/2007 | Sauer et al. |

(Continued)

FOREIGN PATENT DOCUMENTS

| CN | 103153248 | 6/2013 |
| CN | 105266897 | 1/2016 |

(Continued)

OTHER PUBLICATIONS

Uber Blog, "Uber expands options for prescription delivery service with ScriptDrop", Mar. 24, 2021. (Year: 2021).*

(Continued)

*Primary Examiner* — Evangeline Barr
*Assistant Examiner* — Anne-Marie K Alderson
(74) *Attorney, Agent, or Firm* — Perkins Coie LLP

(57) ABSTRACT

An at-home medical diagnostic test kit container including a plurality of at-home medical diagnostic test kits is provided herein. In particular, the medical diagnostic test kit container may include a machine-readable code (e.g., QR code) configured to facilitate an augmented reality experience associated with the at-home medical diagnostic test kit container. In some embodiments, a testing and diagnostic platform may facilitate tracking of inventory within the at-home medical diagnostic test kit container and/or may facilitate coordination of prescription medication order fulfillment and delivery upon indication of a medical condition that could benefit from taking prescription medication.

20 Claims, 43 Drawing Sheets

Related U.S. Application Data continuation of application No. 17/452,966, filed on Oct. 29, 2021, now Pat. No. 11,373,756.

(60) Provisional application No. 63/202,723, filed on Jun. 22, 2021, provisional application No. 63/202,028, filed on May 24, 2021.

(56) References Cited

U.S. PATENT DOCUMENTS

| | | | |
|---|---|---|---|
| 7,491,198 B2 | 2/2009 | Kockro | |
| 7,662,113 B2 | 2/2010 | Pearl et al. | |
| 8,108,190 B2 | 8/2012 | Riener et al. | |
| 8,253,778 B2 | 11/2012 | Atsushi | |
| 8,314,815 B2 | 11/2012 | Navab et al. | |
| 8,485,038 B2 | 12/2013 | Sengupta et al. | |
| 8,611,988 B2 | 12/2013 | Miyamoto | |
| 8,713,130 B2 | 7/2014 | Logan et al. | |
| 8,768,022 B2 | 8/2014 | Miga et al. | |
| 8,814,691 B2 | 12/2014 | Haddick et al. | |
| 8,911,358 B2 | 12/2014 | Koninckx | |
| 8,948,935 B1 | 3/2015 | Peeters et al. | |
| 8,982,156 B2 | 5/2015 | Maggiore | |
| 9,030,446 B2 | 7/2015 | Mistry et al. | |
| 9,082,319 B2 | 8/2015 | Shimada et al. | |
| 9,111,383 B2 | 8/2015 | Fein et al. | |
| 9,256,711 B2 | 2/2016 | Horseman | |
| 9,262,743 B2 | 3/2016 | Heins et al. | |
| 9,285,871 B2 | 5/2016 | Geisner et al. | |
| 9,338,622 B2 | 5/2016 | Bjontegard | |
| 9,345,957 B2 | 6/2016 | Geisner et al. | |
| 9,380,177 B1 | 8/2016 | Rao et al. | |
| 9,424,761 B2 | 11/2016 | Tuchschmid et al. | |
| 9,498,132 B2 | 11/2016 | Pugh et al. | |
| 9,547,917 B2 | 2/2017 | Zamer | |
| 9,563,266 B2 | 3/2017 | Banerjee et al. | |
| 9,600,934 B2 | 3/2017 | Odessky et al. | |
| 9,606,992 B2 | 5/2017 | Geisner et al. | |
| 9,648,436 B2 | 10/2017 | Kraft | |
| 9,788,714 B2 | 12/2017 | Krueger | |
| 9,836,888 B2 | 12/2017 | Skidmore | |
| 9,877,642 B2 | 2/2018 | Duret | |
| 9,886,458 B2 | 2/2018 | Jung et al. | |
| 9,892,561 B2 | 2/2018 | Choukroun et al. | |
| 9,898,662 B2 | 3/2018 | Tsuda et al. | |
| 9,916,002 B2 | 5/2018 | Petrovskaya et al. | |
| 9,972,137 B2 | 7/2018 | Petrovskaya et al. | |
| 10,013,896 B2 | 8/2018 | Feins et al. | |
| 10,052,026 B1 | 10/2018 | Tran | |
| 10,106,172 B2 | 10/2018 | Wingfield et al. | |
| 10,108,266 B2 | 11/2018 | Banerjee et al. | |
| 10,127,734 B2 | 11/2018 | Stroila | |
| 10,156,900 B2 | 12/2018 | Publicover et al. | |
| 10,197,803 B2 | 2/2019 | Badiali et al. | |
| 10,216,957 B2 | 3/2019 | Jung et al. | |
| 10,231,614 B2 | 5/2019 | Krueger | |
| 10,295,815 B2 | 6/2019 | Romanowski et al. | |
| 10,322,313 B2 | 7/2019 | McKirdy | |
| 10,346,889 B1* | 7/2019 | Reiss | G06Q 10/0833 |
| 10,386,918 B2 | 10/2019 | Shin | |
| 10,430,985 B2 | 11/2019 | Harrises et al. | |
| 10,474,233 B2 | 11/2019 | Swaminathan et al. | |
| 10,511,597 B1 | 12/2019 | Phillips et al. | |
| 10,524,715 B2 | 1/2020 | Sahin | |
| 10,535,202 B2 | 1/2020 | Schmirler et al. | |
| 10,540,776 B2 | 2/2020 | Tran et al. | |
| 10,559,117 B2 | 3/2020 | Kaeser et al. | |
| 10,593,092 B2 | 5/2020 | Solomon | |
| 10,643,210 B2 | 5/2020 | Smith et al. | |
| 10,660,522 B2 | 5/2020 | Redei | |
| 10,664,572 B2 | 9/2020 | Bitran et al. | |
| 10,758,209 B2 | 9/2020 | Boctor et al. | |
| 10,788,791 B2 | 10/2020 | Gelman et al. | |
| 10,802,695 B2 | 11/2020 | Daniels et al. | |
| 10,824,310 B2 | 11/2020 | Acharya et al. | |
| 10,832,488 B2 | 12/2020 | Petrovskaya et al. | |
| 10,849,688 B2 | 12/2020 | Rios et al. | |
| 10,885,530 B2 | 1/2021 | Mercury et al. | |
| 10,888,389 B2 | 1/2021 | Draelos et al. | |
| 10,892,052 B2 | 2/2021 | Jordan et al. | |
| 10,910,016 B2 | 3/2021 | Rothschild et al. | |
| 10,932,705 B2 | 3/2021 | Muhsin et al. | |
| 10,943,407 B1 | 3/2021 | Morgan et al. | |
| 10,945,807 B2 | 3/2021 | Gibby et al. | |
| 10,957,111 B2 | 4/2021 | Weisman et al. | |
| 10,984,910 B2 | 4/2021 | Burkholz et al. | |
| 10,991,185 B1 | 4/2021 | Luthra et al. | |
| 10,991,190 B1 | 4/2021 | Luthra et al. | |
| 10,991,461 B2 | 5/2021 | Divine et al. | |
| 11,004,271 B2 | 5/2021 | Cvetko et al. | |
| 11,017,694 B2 | 10/2021 | Buras et al. | |
| 11,152,093 B1 | 10/2021 | Hopen et al. | |
| 11,194,995 B1 | 12/2021 | Profida Ferreira et al. | |
| 11,257,572 B1 | 2/2022 | Narke et al. | |
| 11,219,428 B2 | 3/2022 | Burkholz | |
| 11,270,235 B1 | 3/2022 | Daianu et al. | |
| 11,289,196 B1 | 3/2022 | Ferro, Jr. et al. | |
| 11,315,053 B1 | 4/2022 | Powell et al. | |
| 11,373,756 B1 | 6/2022 | Ferro, Jr. et al. | |
| 2007/0048723 A1 | 3/2007 | Brewer et al. | |
| 2009/0004055 A1 | 1/2009 | Darrigrand et al. | |
| 2009/0263775 A1 | 10/2009 | Ullrich | |
| 2010/0121156 A1 | 5/2010 | Yoo | |
| 2010/0159434 A1 | 6/2010 | Lampotang et al. | |
| 2011/0164105 A1 | 7/2011 | Lee | |
| 2011/0207108 A1 | 8/2011 | Dorman | |
| 2012/0053955 A1* | 3/2012 | Martin | G16H 10/60 358/1.11 |
| 2013/0096937 A1 | 4/2013 | Campbell et al. | |
| 2013/0253339 A1 | 9/2013 | Reyes | |
| 2013/0344470 A1 | 12/2013 | Morgan et al. | |
| 2014/0160264 A1 | 6/2014 | Taylor et al. | |
| 2014/0253590 A1 | 9/2014 | Needham et al. | |
| 2014/0304335 A1 | 10/2014 | Fung et al. | |
| 2016/0125765 A1 | 5/2016 | Meretei et al. | |
| 2016/0189573 A1 | 6/2016 | Bush | |
| 2016/0292378 A1 | 10/2016 | Saric | |
| 2016/0371884 A1 | 12/2016 | Benko et al. | |
| 2017/0103440 A1 | 4/2017 | Xing et al. | |
| 2017/0115742 A1 | 4/2017 | Xing et al. | |
| 2017/0146801 A1 | 5/2017 | Stempora | |
| 2017/0173262 A1 | 6/2017 | Veltz | |
| 2017/0323062 A1 | 11/2017 | Djajadiningrat et al. | |
| 2018/0039737 A1 | 2/2018 | Dempers et al. | |
| 2018/0092595 A1* | 4/2018 | Chen | A61M 15/00 |
| 2018/0140362 A1 | 5/2018 | Cali et al. | |
| 2018/0173913 A1 | 6/2018 | Pulitzer et al. | |
| 2018/0197624 A1 | 7/2018 | Robaina et al. | |
| 2018/0225982 A1 | 8/2018 | Jaeh et al. | |
| 2018/0253840 A1 | 9/2018 | Tran | |
| 2018/0341919 A1 | 11/2018 | Luhman | |
| 2018/0353073 A1 | 12/2018 | Boucher et al. | |
| 2018/0365641 A1* | 12/2018 | Zhu | G06K 7/1417 |
| 2019/0000564 A1 | 1/2019 | Navab et al. | |
| 2019/0005195 A1 | 1/2019 | Peterson | |
| 2019/0012176 A1 | 1/2019 | McHale | |
| 2019/0020651 A1 | 1/2019 | Soon-Shiong et al. | |
| 2019/0025919 A1 | 1/2019 | Tadi et al. | |
| 2019/0064520 A1 | 2/2019 | Christensen | |
| 2019/0073110 A1 | 3/2019 | Bradley et al. | |
| 2019/0139318 A1 | 5/2019 | Tierney et al. | |
| 2019/0179584 A1 | 6/2019 | Masters | |
| 2019/0206134 A1 | 7/2019 | Devam et al. | |
| 2019/0216452 A1 | 8/2019 | Nawana et al. | |
| 2019/0259483 A1 | 8/2019 | Potts | |
| 2019/0261914 A1 | 8/2019 | Davis et al. | |
| 2019/0266663 A1 | 12/2019 | Keeler et al. | |
| 2019/0378080 A1* | 12/2019 | Srinivasan | G06Q 20/3224 |
| 2019/0380790 A1 | 12/2019 | Fuchs et al. | |
| 2019/0391638 A1 | 12/2019 | Khaderi et al. | |
| 2020/0000401 A1 | 1/2020 | Dullen | |
| 2020/0020171 A1 | 3/2020 | Hendricks et al. | |
| 2020/0073143 A1 | 4/2020 | Macnamara et al. | |
| 2020/0101367 A1 | 5/2020 | Tran et al. | |

(56) References Cited

U.S. PATENT DOCUMENTS

| | | | |
|---|---|---|---|
| 2020/0152339 A1* | 5/2020 | Pulitzer | G16H 10/40 |
| 2020/0174756 A1 | 6/2020 | Cerar et al. | |
| 2020/0175769 A1 | 7/2020 | Mandala | |
| 2020/0205913 A1 | 7/2020 | Carnes et al. | |
| 2020/0207501 A1 | 7/2020 | Urquhart et al. | |
| 2020/0211291 A1 | 7/2020 | Miller et al. | |
| 2020/0226758 A1 | 8/2020 | Carnes et al. | |
| 2020/0250389 A1 | 9/2020 | Pulitzer et al. | |
| 2020/0303044 A1 | 9/2020 | Stephen | |
| 2020/0312038 A1 | 10/2020 | Samec et al. | |
| 2020/0312437 A1 | 10/2020 | Wendland | |
| 2020/0337631 A1 | 10/2020 | Sahin | |
| 2020/0342679 A1 | 12/2020 | Soon-Shiong | |
| 2020/0405257 A1 | 12/2020 | Samec et al. | |
| 2020/0409159 A1 | 12/2020 | Samec et al. | |
| 2021/0015583 A1 | 1/2021 | Avisar | |
| 2021/0022810 A1 | 2/2021 | Mahfouz | |
| 2021/0058485 A1 | 3/2021 | Devam et al. | |
| 2021/0086989 A1 | 4/2021 | Luxford | |
| 2021/0118029 A1 | 6/2021 | Koritala | |
| 2021/0183507 A1* | 6/2021 | Shaya | H04N 7/141 |
| 2021/0223239 A1 | 7/2021 | De et al. | |
| 2021/0293805 A1* | 9/2021 | Rothberg | G16B 25/20 |
| 2021/0295954 A1* | 9/2021 | Rothberg | G16H 30/40 |
| 2021/0326474 A1 | 10/2021 | Sparks et al. | |
| 2021/0327304 A1 | 11/2021 | Buras | |
| 2021/0350883 A1 | 11/2021 | Li et al. | |
| 2021/0358064 A1 | 11/2021 | Kudo | |
| 2021/0358068 A1 | 11/2021 | Boszczyk et al. | |
| 2022/0020236 A1* | 1/2022 | Luthra | G16H 50/80 |
| 2022/0084659 A1* | 3/2022 | Rowe | G06V 10/56 |
| 2022/0101608 A1 | 3/2022 | Hu | |
| 2023/0107915 A1 | 4/2023 | Lyon et al. | |

FOREIGN PATENT DOCUMENTS

| | | |
|---|---|---|
| KR | 10-2008-0012745 | 2/2008 |
| KR | 10-2018-0068703 | 6/2018 |
| WO | 2021044064 A1 | 3/2021 |
| WO | WO 21/044064 | 3/2021 |
| WO | WO 21/171226 | 9/2021 |

OTHER PUBLICATIONS

Baruah, Basant, "Augmented reality and QR codes—What you need to know", accessed via wayback machine for Apr. 14, 2021, beaconstac blog.

Zheng, Lixia, "Using Augmented Reality with Interactive Narrative to Help Paediatric Patients Take Prescription Medication", 2020, University College London.

Abbott, Dec. 2020, Binaxnow™ covid-19 Ag card home test and Navica™ app, https://web.archive.org/web/20201224151604/https://wwww.globalpointofcare/abbott, 3 pp.

Baruah, Basant, "Augmented reality and QR codes—what you need to know", Apr. 13, 2020, Beaconstac blog (www.beaconstac.com) (Year: 2020).

U.S. Appl. No. 17/645,222, Non-Final Office Action dated Feb. 3, 2023, pp. 1-54.

U.S. Appl. No. 17/645,223, Final Office Action dated Apr. 14, 2023, pp. 1-62.

U.S. Appl. No. 17/645,223, Non-final Office Action dated Feb. 2, 2023, pp. 1-18.

U.S. Appl. No. 18/171,018 Final Office Action dated Aug. 10, 2023, pagers 1-38.

U.S. Appl. No. 18/171,018 Non-Final Office Action dated May 2, 2023, pp. 1-40.

U.S. Appl. No. 17/645,222 Final Office Action dated Apr. 12, 2023, pp. 1-55.

Zheng, Lixia, "Using Augmented Reality with Interactive Narrative to Help Paediatric Patients Take Prescription Medicine", University College London, 2020. (Year: 2020).

* cited by examiner

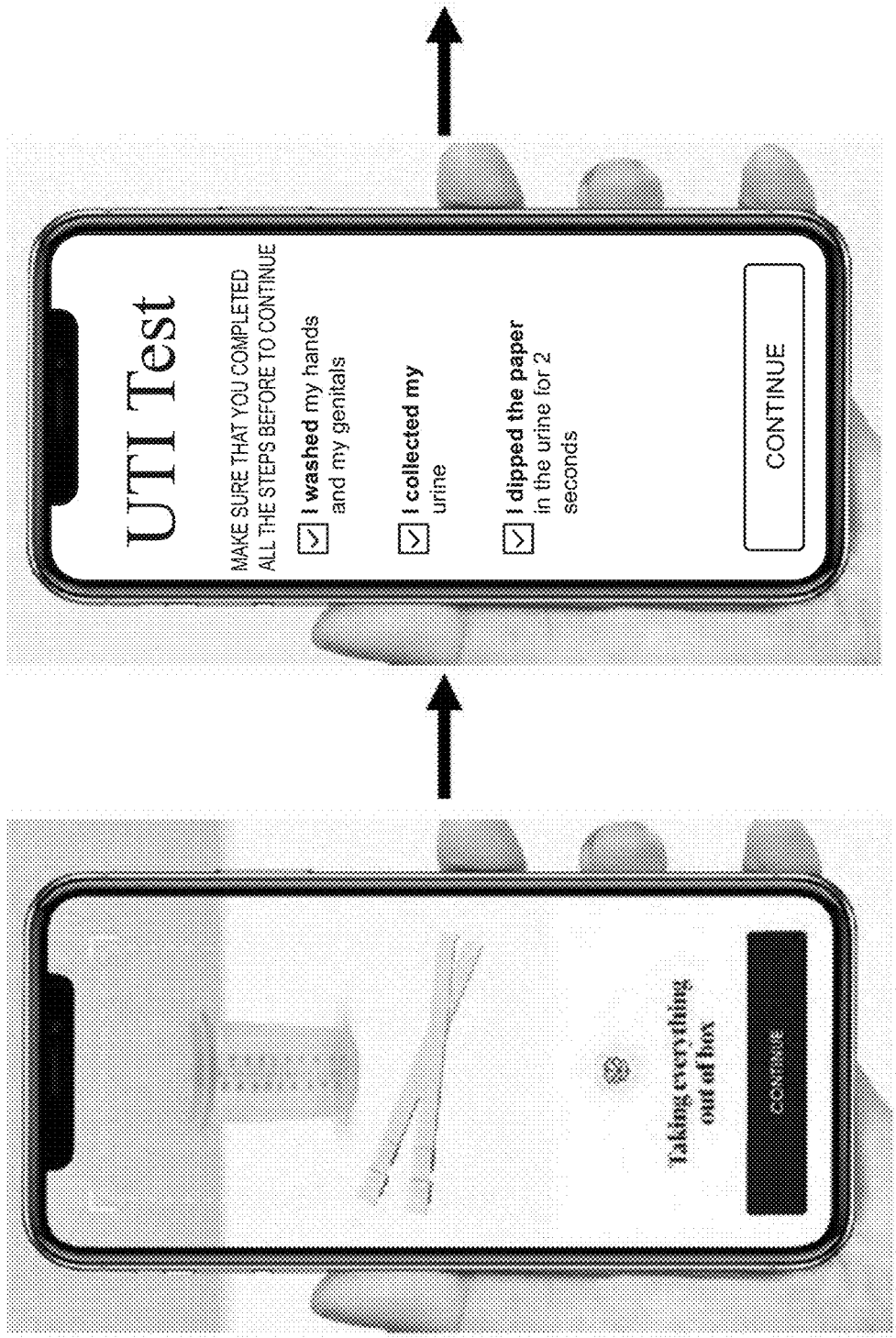

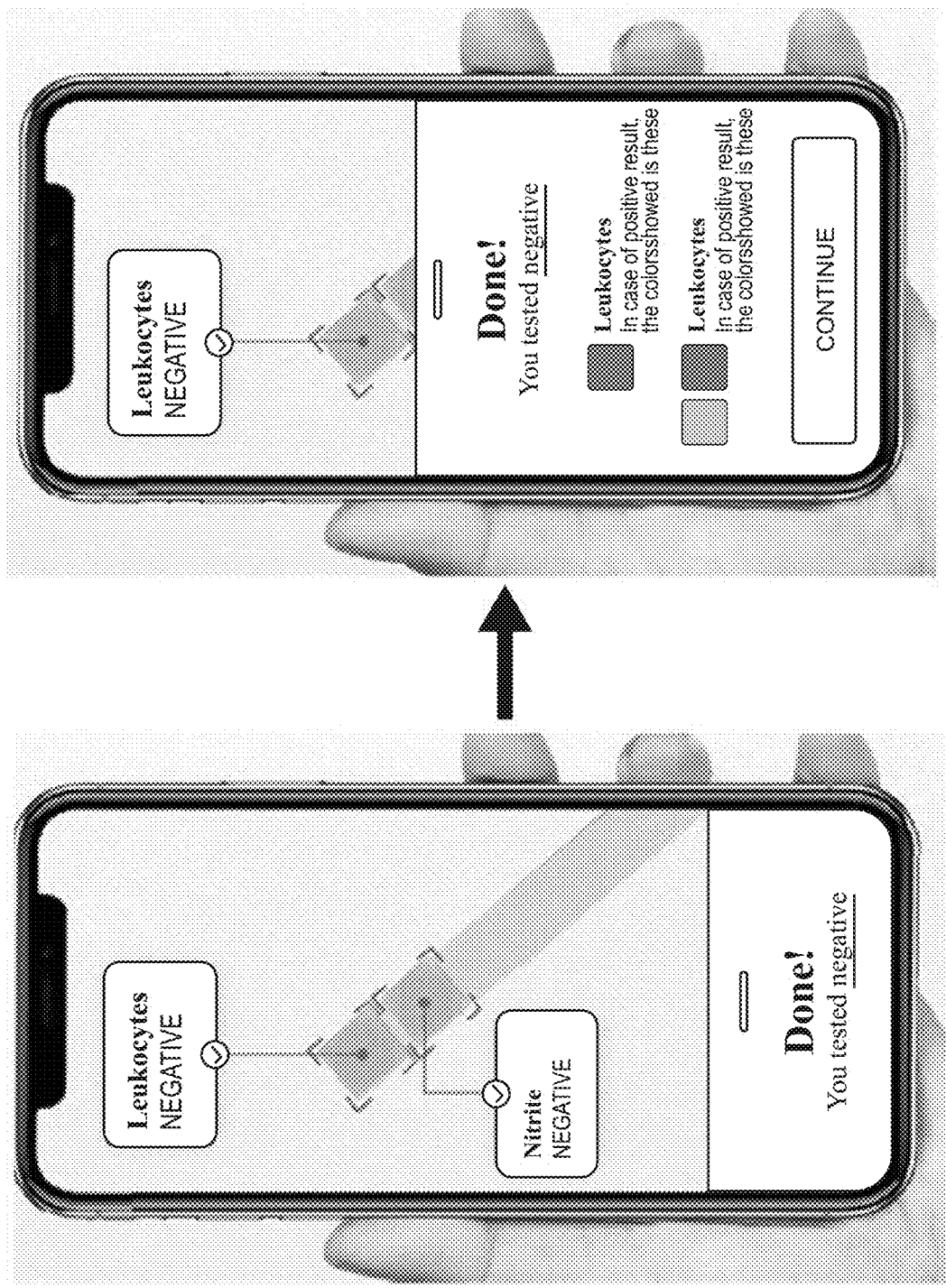

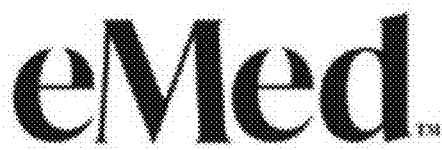

DIGITALLY ENABLED AT-HOME RAPID TESTING

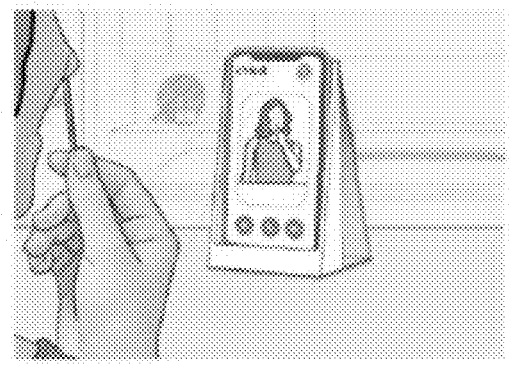

Third-party verified diagnostic testing with certified and validated result reporting powered by eMed. Digital health pass available via mobile app with negative test result.

- Negative test result is CDC accepted for travel.
- Meets CDC requirements for international air traveler U.S. reentry
- Same day Rx deliverly available if test result is positive.

Rx delivery via

STEPS TO BEGIN TESTING

 SCAN YOUR CHOSEN TEST QR CODE.

 LOGIN OR SETUP YOUR ACCOUNT.

 BEGIN YOUR TEST PROCESS.

 VIEW TEST RESULTS.

 RECEIVE YOUR HEALTH PASS OR ADDITIONAL GUIDANCE.

(A) COVID-19 ANTIGEN TEST
(B) INFLUENZA A + B TEST
(C) STREP THROAT TEST
(D) UTI TEST

FIG. 13

✚ AT-HOME RAPID TEST KIT

Ⓐ COVID-19 ANTIGEN TEST*

Test provides a positive accuracy rate of 83.5% detection of SARS-CoV-2 protein antigen.

Ⓑ INFLUENZA A + B TEST**

Test detects influenza type A and type B.

Ⓒ STREP THROAT TEST**

Test detects Group A streptococcal antigen proteins.

Ⓓ UTI TEST**

Urine test that quickly detects whether nitrite and leukocytes are present.

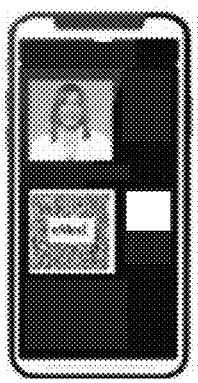

Third-party verified diagnostic testing with certified and validated result reporting powered by eMed. Digital health pass available via mobile app with negative test result is accepted for travel.

*Meets CDC requirements for international air traveler U.S. reentry.
**Some day Rx delivery available if test result is positive.

Rx delivery via

✚ CERTIFIED GUIDE PROCTORED     🕒 RESULTS IN MINUTES     ✓ CERTIFIED HEALTH PASS

FIG. 14

SYSTEMS, DEVICES, AND METHODS FOR DIAGNOSTIC AID KIT APPARATUS

INCORPORATION BY REFERENCE TO ANY PRIORITY APPLICATIONS

This application is a continuation of U.S. patent application Ser. No. 17/452,966, filed Oct. 29, 2021, which is a continuation of U.S. Ser. No. 17/514,891, filed Oct. 29, 2021, which claims priority to U.S. Provisional Patent Application No. 63/202,028, filed May 24, 2021, and U.S. Provisional Patent Application No. 63/202,723, filed Jun. 22, 2021, each of which are incorporated herein by reference. Any and all applications for which a foreign or domestic priority claim is identified in the Application Data Sheet as filed with the present application are hereby incorporated by reference under 37 CFR 1.57.

FIELD

Some embodiments of the present disclosure are directed to systems and methods for conducting remote health testing and diagnostics.

BACKGROUND

Use of telehealth to deliver health care services has grown consistently over the last several decades, and has exploded in usage during the Coronavirus disease 2019 (COVID-19) Public Health Emergency (PHE). Telehealth is the distribution of health-related services and information via electronic information and telecommunication technologies. Telehealth allows long-distance patient and health provider contact, care, advice, reminders, education, intervention, monitoring, and remote admissions. In situations such as the COVID-19 PHE, when many medical and hospital resources are devoted to treating the sick, patients are more reluctant to travel to their health provider in-person, and when access to care is restricted, telehealth provides an invaluable resource.

During the COVID-19 pandemic, testing for coronavirus disease (COVID-19) was extremely limited in various places throughout the world, including the United States. Tracing infected individuals was and continues to be an important step in preventing new cases of infectious diseases. In response, the United States Food and Drug Administration (FDA) has authorized various at-home COVID-19 tests.

At-home testing solves some of the problems with in-person testing. For example, health insurance may not be required, travel to a testing site is avoided, and tests can be completed at a patient's convenience. However, at-home testing introduces various additional logistical and technical issues, such as guaranteeing timely test delivery to a patient's home, providing test delivery from a patient to an appropriate lab, ensuring test verification and integrity, providing test result reporting to appropriate authorities and medical providers, and connecting patients with medical providers, who are needed to provide guidance and/or oversight of the testing procedures remotely. These issues are not unique to COVID-19 and will need to be addressed in relation to remote health diagnostic testing generally.

SUMMARY

For purposes of this summary, certain aspects, advantages, and novel features of the invention are described herein. It is to be understood that not all such advantages necessarily may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

In some embodiments, a kit for use in performing a medical diagnostic test-taking procedure comprises a plurality of components including at least one medical diagnostic test kit and a box or container within which the at least one medical diagnostic test kit is housed. In some such embodiments, at least one of the plurality of components bears graphics on a surface thereof that, when scanned by a user device (e.g., mobile phone, smartphone, tablet, smartwatch, smart glasses), cause the user device to one or both of provide information on the at least one medical diagnostic test kit (or the test to be performed using the medical diagnostic test kit) and establish a connection with a proctoring platform for overseeing a test-taking procedure using the at least one medical diagnostic test kit and verifying corresponding results thereof.

In a first aspect, a medical diagnostic first aid kit can include a container; a plurality of medical diagnostic test kits located within the container, wherein each of the plurality of medical diagnostic test kits comprises equipment necessary to perform a particular self-administered medical diagnostic test, wherein the plurality of medical diagnostic test kits comprise at least a first medical diagnostic kit adapted to facilitate user completion of a first medical diagnostic test and a second medical diagnostic kit adapted to facilitate user completion of a second medical diagnostic test different from the first medical diagnostic test, wherein the container comprises a QR code located on an external surface of the container, the QR code configured to be imaged by a camera of a portable user computing device to enable: providing a fiducial point from which a coordinate frame for an augmented reality presentation can be established using the camera and a display of the portable user computing device; and causing the portable user computing device to display a user-selectable graphic on the display of the portable user computing device that, when selected by a user, causes a software application stored on the portable user computing device to access a provider webpage that enables initiation of the augmented reality presentation that includes display of augmented reality content relating to the plurality of medical diagnostic test kits.

The medical diagnostic first aid kit can include one or more of the following features in any combination: (a) wherein the QR code is printed on the external surface of the container; (b) wherein the QR code is printed on an adhesive sticker that is adhered to the external surface of the container; (c) wherein the augmented reality content relating to the plurality of medical diagnostic test kits comprises information about each of the particular medical diagnostic tests; (d) wherein the augmented reality content relating to the plurality of medical diagnostic test kits comprises information about various steps in a testing process for each of the particular medical diagnostic tests; (e) wherein the QR code is an augmented reality QR code; (f) wherein each of the plurality of medical diagnostic test kits comprises a respective QR code located on an external surface of a package of the medical diagnostic test kit that, when scanned by the portable user computing device, causes the portable user computing device to display information relating to the particular medical diagnostic test and/or instructions on how to perform the particular medical diagnostic test on the display of the portable user computing device; and/or other features as described herein.

In another aspect, a medical diagnostic test kit container can include: a plurality of medical diagnostic test kits located within the container, wherein each of the plurality of medical diagnostic test kits comprises equipment necessary to perform a particular medical diagnostic test, wherein the plurality of medical diagnostic test kits comprise at least a first medical diagnostic kit adapted to facilitate user completion of a first medical diagnostic test and a second medical diagnostic kit adapted to facilitate user completion of a second medical diagnostic test different from the first medical diagnostic test; a machine-readable code located on a surface of the container that, when scanned by a portable user computing device: provides a fiducial point from which a coordinate frame for an augmented reality presentation can be established using a camera and a display of the portable user computing device; and causes the portable user computing device to display a user-selectable graphic on the display of the portable user computing device that, when selected by a user, causes a software application stored on the portable user computing device to access a provider webpage that enables initiation of the augmented reality presentation that includes display of augmented reality content relating to the plurality of medical diagnostic test kits.

The medical diagnostic test kit container can include one or more of the following features in any combination: (a) wherein the machine-readable code is printed on an external surface of the container; (b) wherein the machine-readable code is printed on an internal surface of the container; (c) wherein the machine-readable code is printed on an adhesive sticker that is adhered to an external surface of the container; (d) wherein the machine-readable code is a QR code; (e) wherein the machine-readable code is an augmented reality QR code; (f) wherein the augmented reality content relating to the plurality of medical diagnostic test kits comprises information about each of the particular medical diagnostic tests; (g) wherein the augmented reality content relating to the plurality of medical diagnostic test kits comprises information about various steps in a testing process for each of the particular medical diagnostic tests; and/or other features as described herein.

In another aspect, a method of facilitating an augmented reality experience to familiarize a user with a plurality of at-home medical diagnostic tests provided within a medical diagnostic test kit container can include: providing a user with the medical diagnostic test kit container including a plurality of medical diagnostic test kits, wherein each of the plurality of medical diagnostic test kits comprises equipment necessary to perform a particular medical diagnostic test, wherein the plurality of medical diagnostic tests comprise at least a first medical diagnostic kit adapted to facilitate user performance of a first medical diagnostic test and a second medical diagnostic kit adapted to facilitate user performance of a second medical diagnostic test different from the first medical diagnostic test, wherein the medical diagnostic test kit container comprises a machine-readable code that, when imaged by a camera of a portable user computing device: provides a fiducial point from which a coordinate frame for an augmented reality presentation can be established using the camera and a display of the portable user computing device; and causes the portable user computing device to display a user-selectable graphic on the display of the portable user computing device that, when selected by a user, causes a software application stored on the portable user computing device to access a provider webpage that enables initiation of the augmented reality presentation that includes display of augmented reality content relating to the plurality of medical diagnostic test kits; receiving, by an application server, a request from the user to launch the augmented reality presentation via a graphical user interface displayed on the portable user computing device; and causing, in response to receiving the request from the user, the display of the augmented reality content on the display of the portable user computing device.

The method can include one or more of the following features in any combination: (a) wherein the machine-readable code is a QR code; (b) wherein the machine-readable code is an augmented reality QR code; (c) connecting the user with a provider proctor, via the application server, to facilitate remote proctoring of one or more of the plurality of medical diagnostic tests; (d) providing, by the application server, a virtual pass indicative of a result of the one or more medical diagnostic tests after verification by the provider proctor; (e) providing, by the application server, a prescreening survey to the user to help the user decide whether or not to proceed with self-administration of one or more of the plurality of medical diagnostic tests; and/or other features as described herein.

In another aspect, a computer-implemented system for a proctored examination platform for a medical diagnostic test, can include: an electronic storage medium of a computing system, the electronic storage medium comprising computer-executable instructions; one or more processors of the computing system, the one or more processors in electronic communication with the electronic storage medium, the one or more processors in electronic communication through an electronic network with a user computing device and a courier computing device of a courier, the one or more processors configured to execute the computer-executable instructions stored in the electronic storage medium for implementing the proctored examination platform for the medical diagnostic test by: receiving, by the computing system, through the electronic network a user request from a user for a proctored examination, the user request received from the user computing device; generating, by the computing system, display data for displaying a graphical user interface (GUI) on a display of a proctor device, the display data configured to display to a proctor a set of two or more phases of the medical diagnostic test and a first phase indicator showing a current phase of the first user in the two or more phases of the medical diagnostic test; transmitting, by the computing system, through the electronic network the display data to the proctor device; receiving, by the computing system, through the electronic network a first video conference connection request from the proctor device; establishing, by the computing system, a first electronic video conference session between the proctor device and the first user computing device; receiving, by the computing system, through the electronic network a positive medical diagnostic indicator from the proctor device; generating, by the computing system, user display data for displaying a graphical user interface (GUI) on the display of the user computing device, the user display data configured display medical content data about a positive result for the medical diagnostic test and a user prompt for determining whether the user desires to order prescription drugs for treatment responsive to the positive result for the medical diagnostic test; transmitting, by the computing system, through the electronic network the user display data to the user computing device; receiving, by the computing system, through the electronic network a request to order the prescription drugs from the user computing device; generating, by the computing system, physician display data for displaying a graphical user interface (GUI) on the display of a physician device, the physician display data configured display medical diagnostic data about the positive result for the medical diagnostic test and a physician prompt for generating a prescription for ordering the prescription drugs for treatment responsive to the positive result for the medical diagnostic test; transmitting, by the computing system, through the electronic network the physician display data to the physician device; receiving, by the computing system, through the electronic network a request for generating the prescription for the prescription drugs from the physician device; transmitting, by the computing system, through the electronic network the prescription for the prescription drugs to a pharmacy device; generating, by the computing system, courier data for displaying a graphical user interface (GUI) on the display of the courier computing device, the courier display data configured to cause to display a prescription release code and directions to a pharmacy fulfilling the prescription drug; transmitting, by the computing system, through the electronic network the courier data to the courier computing device; receiving, by the computing system, through the electronic network a pick-up confirmation that the prescription drug was picked up by the courier from the pharmacy device; generating, by the computing system, based on the pick-up confirmation supplemental courier data for displaying the graphical user interface (GUI) on the display of the courier computing device, the supplemental courier display data configured to cause to display directions to the user; and receiving, by the computing system, through the electronic network a delivery confirmation that the prescription drug was delivered by the courier from the user computing device.

The computer-implemented system can include one or more of the following features in any combination: (a) wherein the computing system comprises one or more computing systems; (b) generating, by the computing system, an alert notification for the proctor when the pick-up confirmation is not received by the computing system within a pick-up threshold period; (c) wherein the pick-up threshold period is in part determined by a time period calculated based on a distance between a location of the pharmacy and a current location of the courier; (d) wherein the threshold period is in part further determined by a pick-up time; (e) wherein the current location of the courier is determined by a GPS unit in the courier computing device; (f) generating, by the computing system, an alert notification for the proctor when the delivery confirmation is not received by the computing system within a delivery threshold period; (g) wherein the threshold period is in part determined by a time period calculated based on a distance between a location of the user and a current location of the courier; (h) wherein the current location of the courier is determined by a GPS unit in the courier computing device; (i) wherein the threshold period is in part further determined by a delivery time; (j) wherein the prescription release code is a QR code; and/or other features as described herein.

In another aspect, a computer-implemented method for a proctored examination platform for a medical diagnostic test, the computer-implemented method can include: receiving, by the computing system, through an electronic network from a user computing device a user request for a user for a proctored examination, the user request received from the user computing device; generating, by the computing system, display data for displaying a graphical user interface (GUI) on a display of a proctor device, the display data configured to display to a proctor a video conference session for the medical diagnostic test, the video conference session establishing an electronic video conference connection between the user computing device and the proctor device; transmitting, by the computing system, through the electronic network the display data to the proctor device; receiving, by the computing system, through the electronic network a positive medical diagnostic indicator from the proctor device; generating, by the computing system, user display data for displaying a graphical user interface (GUI) on the display of the user computing device, the user display data configured display medical content data about a positive result for the medical diagnostic test and a user prompt for determining whether the user desires to order prescription drugs for treatment responsive to the positive result for the medical diagnostic test; transmitting, by the computing system, through the electronic network the user display data to the user computing device; receiving, by the computing system, through the electronic network a request to order the prescription drugs from the user computing device; generating, by the computing system, physician display data for displaying a graphical user interface (GUI) on the display of a physician device, the physician display data configured display medical diagnostic data about the positive result for the medical diagnostic test and a physician prompt for generating a prescription for ordering the prescription drugs for treatment responsive to the positive result for the medical diagnostic test; transmitting, by the computing system, through the electronic network the physician display data to the physician device; receiving, by the computing system, through the electronic network a request for generating the prescription for the prescription drugs from the physician device; transmitting, by the computing system, through the electronic network the prescription for the prescription drugs to a pharmacy device; generating, by the computing system, courier data for displaying a graphical user interface (GUI) on the display of a courier computing device, the courier display data configured to cause to display directions to a pharmacy fulfilling the prescription drug; transmitting, by the computing system, through the electronic network the courier data to the courier computing device; receiving, by the computing system, through the electronic network a pick-up confirmation that the prescription drug was picked up by the courier from the pharmacy device; generating, by the computing system, based on the pick-up confirmation supplemental courier data for displaying the graphical user interface (GUI) on the display of the courier computing device, the supplemental courier display data configured to cause to display directions to the user; and receiving, by the computing system, through the electronic network a delivery confirmation that the prescription drug was delivered by the courier from the user computing device, wherein the computing system comprises one or more processors and an electronic memory.

The computer-implemented system can include one or more of the following features in any combination: (a) generating, by the computing system, an alert notification for the proctor when the pick-up confirmation is not received by the computing system within a pick-up threshold period; (b) wherein the pick-up threshold period is in part determined by a time period calculated based on a distance between a location of the pharmacy and a current location of the courier; (c) wherein the threshold period is in part further determined by a pick-up time; (d) wherein the current location of the courier is determined by a GPS unit in the courier computing device; (e) generating, by the computing system, an alert notification for the proctor when the delivery confirmation is not received by the computing system within a delivery threshold period; (f) wherein the threshold period is in part determined by a time period calculated based on a distance between a location of the user and a current location of the courier; (g) wherein the current location of the courier is determined by a GPS unit in the courier computing device; (h) wherein the courier data further comprises a prescription release code, the prescription release code comprises one or more of a code, a barcode, and a QR code; and/or other features as described herein.

BRIEF DESCRIPTION OF THE DRAWINGS

The drawings are provided to illustrate example embodiments and are not intended to limit the scope of the disclosure. A better understanding of the systems and methods described herein will be appreciated upon reference to the following description in conjunction with the accompanying drawings, wherein:

FIGS. 10A-10H illustrate a series of example screen displays that can be displayed to a user to guide the user through the steps of administering an at-home urinary tract infection test according to some embodiments described herein.

FIGS. 13 and 14 are examples of graphic labels or inserts that may be provided on or inside the medical diagnostic test kit container or package of FIG. 1 according to some embodiments described herein.

DETAILED DESCRIPTION

Figure 1:
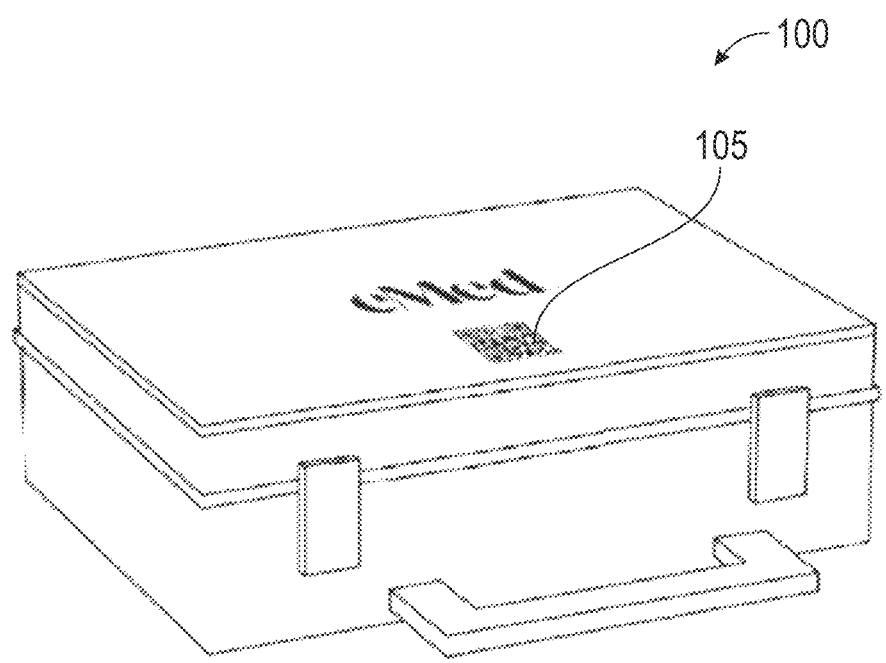
FIG. 1 illustrates an example of an at-home medical diagnostic test kit container or package having a machine-readable code that can be scanned to initiate an augmented reality experience according to some embodiments described herein.

Although certain preferred embodiments and examples are disclosed below, inventive subject matter extends beyond the specifically disclosed embodiments to other alternative embodiments and/or uses and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present technology. The section headings used herein are merely provided to enhance readability and are not intended to limit the scope of the embodiments disclosed in a particular section to the features or elements disclosed in that section.

Some embodiments herein are directed to a medical diagnostic test kit container or package that functions similar to a first aid kit but includes several at-home medical diagnostic test kits of different types that a household (e.g., an individual or family), care facility or assisted living center, or other group or individual, could use to complete at-home medical testing. The diagnostic test kit container or package may be purchased from an e-commerce provider or a retail store without requiring a prescription and stored and used on demand as needs arise for diagnostic or medical testing. For example, if an individual is feeling sick or experiencing symptoms of a medical condition (such as COVID-19, influenza, or urinary tract infection), the individual may open the medical diagnostic test kit container and select an appropriate at-home diagnostic test and complete the at-home medical diagnostic test. The at-home medical diagnostic tests may be self-administered, administered by another individual in the household or care facility, or a health care provider.

Of course, the medical diagnostic test kits may also be used even in instances where no symptoms are being experienced, as desired. In addition, if a negative screening test is required prior to travel or employment (such as a negative COVID-19 test or a negative drug test), the medical diagnostic test kit container may include screening tests that are certified and accepted as proof by government agencies, travel companies and institutions (such as airlines, cruise ship companies), restaurants, gyms, fitness centers, hospitals, other retail establishments, and employers that may require proof of negative diagnostic tests.

Different medical diagnostic test kit containers or packages may include various types and numbers of tests designed for different individuals, households, care facilities, etc. A label on the diagnostic test kit container may indicate the types and numbers of medical diagnostic tests in the particular container or package. In addition, supplemental medical diagnostic test kits may be ordered (e.g., via an e-commerce website or platform) when needed to restock supply. Certain medical diagnostic test kits may require a prescription or approval from a health care provider prior to ordering. Other medical diagnostic test kits may be purchased without any prescription or approval at the time of purchase.

The medical diagnostic test kit container or package may include a machine-readable code located on an external surface of the box that can be scanned by a camera of a user device (such as a personal computer, a cellular phone, a smartphone, a laptop, a tablet computer, smart glasses, an e-reader device, an audio player, or another device capable of connecting to and communicating over a network, whether wired or wireless) to initiate an augmented reality interactive experience for user computing devices that have augmented reality capability (e.g., AR-compatible smartphone, tablet, or smart glasses). The augmented reality experience can include, for example, interactive displays that show the types of medical diagnostic test kits included in the medical diagnostic test kit container or package, an overview of the steps required for each of the medical diagnostic tests, the materials (e.g., test equipment) included in the medical diagnostic test kits, and a guided step-by-step process to facilitate completion of each of the medical diagnostic tests. The augmented reality experience may help users visualize and complete the steps of an at-home test more easily and provide an enhanced user experience.

A remote health testing and diagnostic platform (e.g., a digital point-of-care platform operated by a commercial entity, such as eMed based in Florida) may also be used to facilitate coordination with proctors to enable certification of certain of the diagnostic tests, to facilitate ordering and delivery of prescription medicine that may be helpful to treat a medical condition identified by a medical diagnostic test in the medical diagnostic test kit package, to facilitate generation of a certification or pass that can be displayed as proof of a negative screening test (such as a negative COVID-19 test), to facilitate re-ordering or supplemental ordering of medical diagnostic test kits when inventory of a particular medical diagnostic test kit type in the medical diagnostic test kit container or package is low or out of stock, and/or to generate pre-screening surveys to determine whether or not it makes sense for the user to actually complete a particular medical diagnostic test.

At-home medical testing provides both safety and convenience to patients and medical providers. In-person visits by individuals with infectious diseases endangers both medical professionals, as well as anyone who encounters the individuals on their way to the in-person visit or in the waiting room. At-home testing does not involve personal contact between the patient and any other individuals who may otherwise be at risk. Furthermore, at-home testing is simply more convenient, as neither medical providers nor patients need to leave the safety or comfort of their home in order to administer a test using remote testing platforms.

Additionally, because of advancements in medical and logistics technology, especially as described herein, at-home testing can now be extremely fast. In some cases, medical diagnostic tests can be administered and read within seconds. Other tests may require a cure time before being read or may require delivery to a laboratory to receive results, but results can still be received within days in most cases.

Applications for at-home medical testing are abundant. For example, at-home testing can be used by travelers in any location to ensure that the traveler is healthy before and/or after arriving at a destination, without having to locate medical care in an unfamiliar locale. Furthermore, at-home testing may prevent the spread of infectious diseases by providing travelers knowledge of when to quarantine or avoid traveling altogether, and to avoid bringing home an infectious disease. At-home testing may also be useful for sensitive individuals such as the elderly and children. At-home testing may provide a better experience for such sensitive individuals, especially in cases in which the testing procedure is uncomfortable or invasive. At-home testing can mean that the test is done in a safe, comfortable, and familiar environment, so sensitive individuals may feel less stressed and worried during their test, allowing testing to proceed more smoothly. In some instances, at-home testing can be performed in a user's home, although this need not be the case in all instances. For example, as used herein, at-home testing can refer to testing performed in other locations outside the home, such as in hotel rooms, airports, or other remote locations where access to an in-person healthcare provider is not available or desirable. Another consideration for at-home testing is privacy. At-home testing can be private and discreet, which is ideal for high-profile individuals or sensitive individuals who want to get tested without leaving their homes. Also, accessibility considerations favor at-home testing. At-home testing is ideal for anyone who has transportation issues or mobility/accessibility considerations.

In some embodiments, the remote health testing and diagnostic platform may facilitate administration of a medical diagnostic test to a patient with the guidance of a proctor. In some embodiments, the proctor may comprise uncertified personnel, certified medical personnel, and/or a proctor for monitoring an algorithm such as computer software, which may administer a medical diagnostic test. In some embodiments, the computer software is not administering the medical diagnostic test but rather is monitoring the medical diagnostic test for abnormalities or deviations or inconsistencies in the administration or performance or procedure of the medical diagnostic test that is being administered by the uncertified personnel and/or certified medical personnel and/or medical personnel and/or the like. In some embodiments, the patient may be provided with step-by-step instructions for test administration by the proctor within a testing environment. The platform may display unique, dynamic testing interfaces to the patient and proctor to ensure proper testing protocols and/or accurate test result verification. The displays may be enhanced with augmented reality content overlaid on images obtained by cameras of a user device, such as a smartphone or tablet, to enhance the user experience and reduce user compliance errors.

In some embodiments, the platform may provide a testing environment comprising a private communication channel (such as over the internet) between a proctor and a patient. In some embodiments, the testing environment may comprise one or more unique user interfaces that may facilitate seamless testing, submission and verification. In some embodiments, the platform may provide for automatic transmission of verified test results to users, relevant authorities, and third parties. In some embodiments, the platform may generate a unique health card or passport, which may provide an easily accessible and understandable testing summary for a patient and/or third parties.

In some embodiments, the platform may also be configured to provide urgent care to patients in need by collecting symptom and medical data from patients and providing such data to relevant medical professionals and pharmacies. In some embodiments, the platform may facilitate diagnosis of a patient by a third-party medical provider and fulfillment and even delivery of a drug prescription by a third-party pharmacy and a third-party courier service, without any of the parties having direct (e.g., physical or in person) contact.

At-Home Medical Diagnostic Test Kit Container

Figure 19:
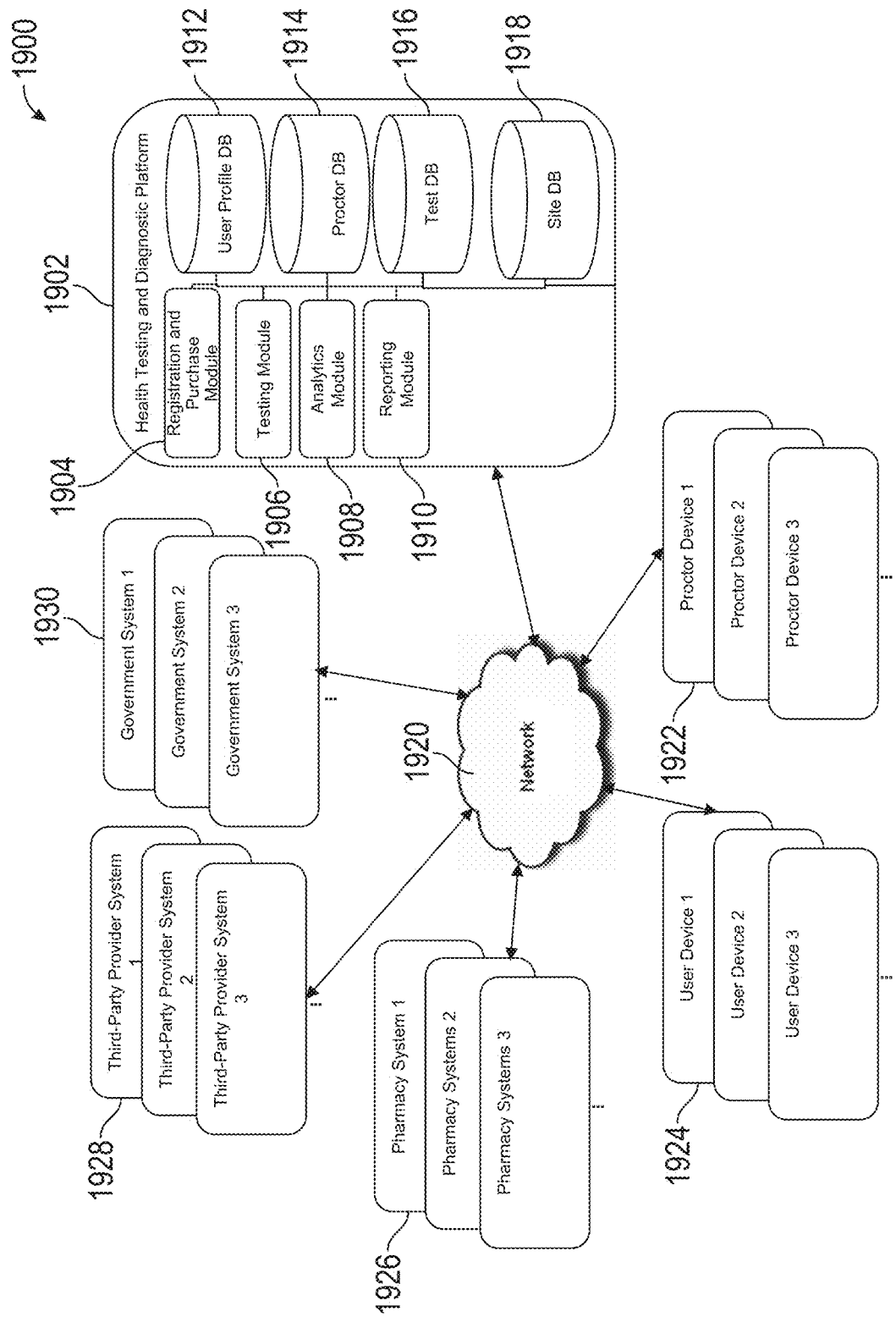
FIG. 19 is a block diagram illustrating an example embodiment of a computer system configured to run software for implementing one or more embodiments of the systems, methods, and devices disclosed herein.

FIG. 1 illustrates an example of an at-home medical diagnostic test kit container or package 100 that may be utilized in conjunction with a remote health testing and diagnostic platform (e.g., platform 1902 shown in FIG. 19). The medical diagnostic test kit container or package 100 may function similar to a first aid kit but, instead of including bandages, gauze pads, wraps, ointments, or other typical first aid kit supplies, includes a plurality of medical diagnostic test kits of various types that can be used to perform at-home or self-administered medical diagnostic tests. The diagnostic test kit container 100 may comprise a box, package, canister, or other container adapted to hold and store contents. The diagnostic test kit container 100 may be made of plastic, cardboard, metal, polymeric, or other material.

The medical diagnostic test kit container 100 may include one or more graphics (e.g., images and/or alphanumeric text). The graphics may be printed on an exterior surface of the medical diagnostic test kit container 100 or may be printed on an adhesive label or sticker that is adhered to the exterior surface of the medical diagnostic test kit container 100. The graphics may include, among other things, a machine-readable code 105 (e.g., QR code, AR code, bar code, datamatrix code, PDF417 code, Aztec code) that, when scanned or imaged by a user device, such as a mobile computing device having one or more built-in cameras, causes the user device to provide information about the collection of medical diagnostic test kits within the medical diagnostic test kit container 100 as a whole, about the individual medical diagnostic test kits, and/or about the medical diagnostic tests themselves. In one implementation, the machine readable code 105 is an AR code configured to facilitate display of augmented reality content. In some embodiments, the machine readable code 105 may correspond to a graphic (e.g., an image, logo, etc.) that an application or web app may recognize using one or more computer vision techniques to provide one or more pieces of the aforementioned information.

Although the machine-readable code 105 is shown located on a top external surface of the medical diagnostic test kit container 100 in a central location, it should be appreciated that other locations for the machine-readable code 105 are also contemplated (e.g., other locations on the top external surface, locations on a different external surface, internal locations). In addition, there may be multiple instances of the machine-readable code 105 at various locations on the medical diagnostic test kit container 100.

In accordance with various embodiments, the medical diagnostic test kits that may be included in the medical diagnostic test kit container 100 include, but are not limited to, the following:

| Test Name | Condition(s) | Test Mechanism | Sample Type |
|---|---|---|---|
| COVID-19 Rapid Test Kit | SARS-CoV-2 | Antigen | Nasal Swab (Anterior) |
| UTI Emergency Kit | UTI | Analyte | Urine |
| Drug Test | Drug | Antigen | Saliva |
| Syphilis Rapid Test Kit | STD/STI | Analyte | Finger Prick |
| COVID-19 All-In-One Test Kit | SARS-CoV-2 | PCR (molecular) | Nasal Swab (Anterior) |
| Strep | Strep A | Immunolateral Flow Cell | Throat Swab |
| Flu | Influenza AZB | Immunolateral Flow Cell | Nasal Swab (Anterior) |
| UTI Test Strips | UTI | Analyte | Urine |
| STD Multitest | STD/STI | LAMP | Urine |
| Sexual Health Multi-Test Pack | STD/STI | Lateral immunoflow | Multiple - blood or fluid sample |
| IGM & IGG COMBO COVID-19 ANTIBODY | SARS-CoV-2 | Antibody | Finger Prick |
| Gonorrhea Rapid Test Kit | STD/STI | Analyte | Genital Swab |
| Hepatitis B Rapid Test Kit | STD/STI | Analyte | Finger Prick |
| Chlamydia Rapid Test Kit | STD/STI | Analyte | Genital Swab |

The medical diagnostic test kits may include test kits configured for diagnosing or testing various medical conditions (which may be symptomatic conditions or asymptomatic conditions) and may involve various different test mechanisms (e.g., analyte tests, antibody tests, polymerase chain reaction (PCR) tests, lateral flow immunoassay tests, loop mediated isothermal amplification (LAMP) assay tests, etc.), and means of obtaining diagnostic samples (e.g., urine, finger prick, saliva, nasal swab, genital swab, throat swab, etc.).

Some of the medical diagnostic test kits may be administered when an individual is not feeling well or is experiencing symptoms of a suspected medical condition. Some of the medical diagnostic test kits, such as COVID-19 test kits or drug test kits, may be administered on-demand when an individual is required to show proof of a negative diagnostic test (e.g., prior to travel or entry into a public event or retail or commercial building, prior to employment or periodically during employment for verification, prior to attending school or college, etc.).

In several implementations, the machine-readable code 105, when scanned by a camera of the user device (e.g., using a camera application or a QR code scanner application of the user device), can direct the user (e.g., via a Web browser application stored on the user device) to a proprietary platform website or Web application running on one or more servers, or a software application stored on the user device, that can provide the user with an option to initiate an augmented reality experience to explore the contents of the medical diagnostic test kit container 100 using the user device without even opening the medical diagnostic test kit container 100.

Figure 2A:
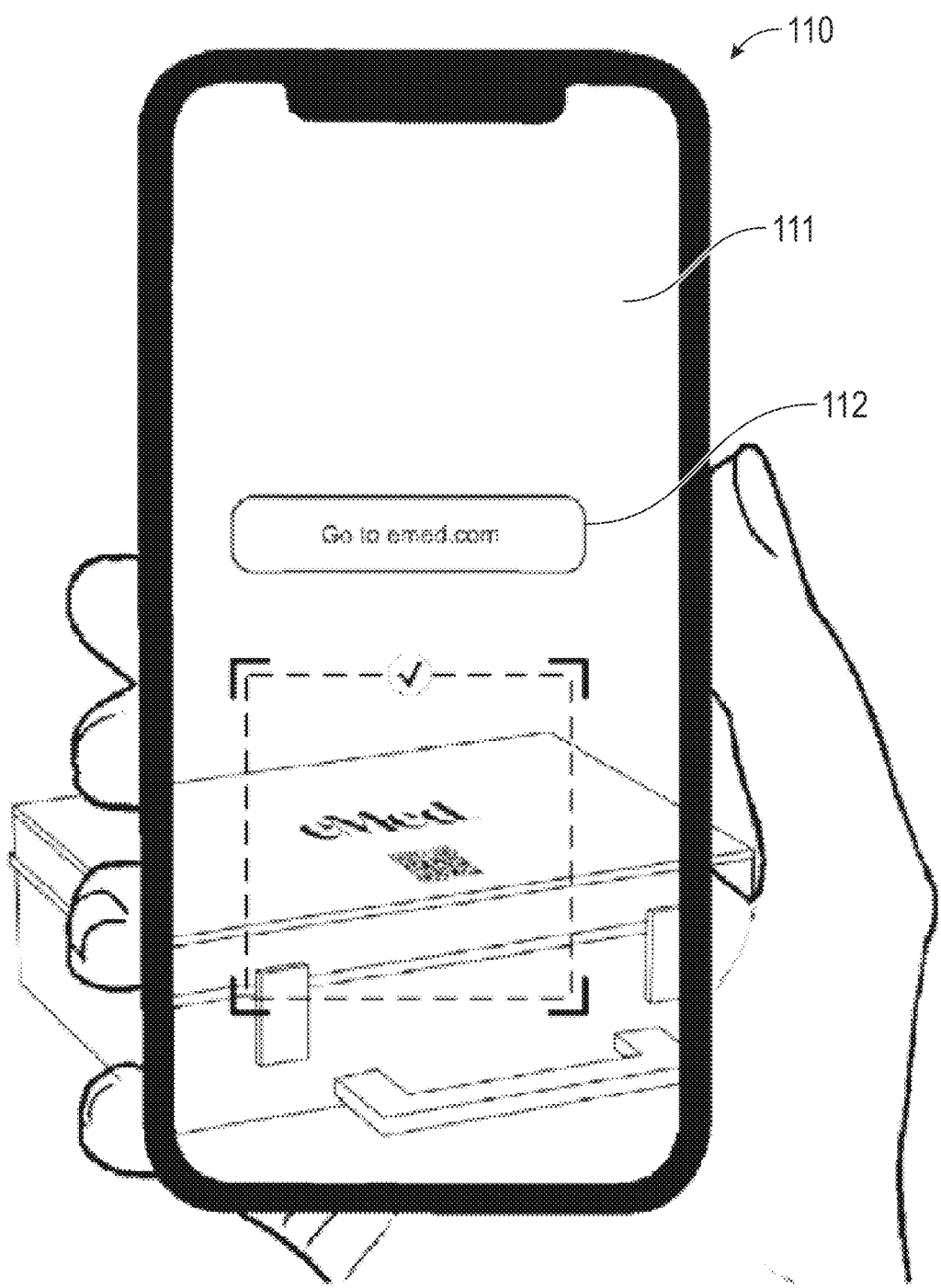
FIG. 2A illustrates an example of a user scanning the machine-readable code on the medical diagnostic test kit container of FIG. 1 using a camera of a user device (such as a mobile phone), as well as an example graphical user interface shown on a display of the user device after the machine-readable code has been scanned, according to some embodiments described herein.

FIG. 2A illustrates an example of an individual scanning the machine-readable code 105 on the medical diagnostic test kit container 100 using a built-in camera (e.g., rear-facing camera) of a user device 110 (such as a mobile phone, smartphone, tablet, laptop, e-Reader device, smartwatch, smart glasses). The real-time video images obtained by the camera(s) of the user device 110 can be displayed on a display screen 111 of the user device 110. As shown, a graphical user interface may be presented on the display screen 111 that allows the user to choose (by interacting with an image and/or text hyperlink or button 112 on the display screen 111) to navigate to a proprietary platform website using a Web browser application stored on the user device 110 capable of accessing the Internet.

Figure 2B:
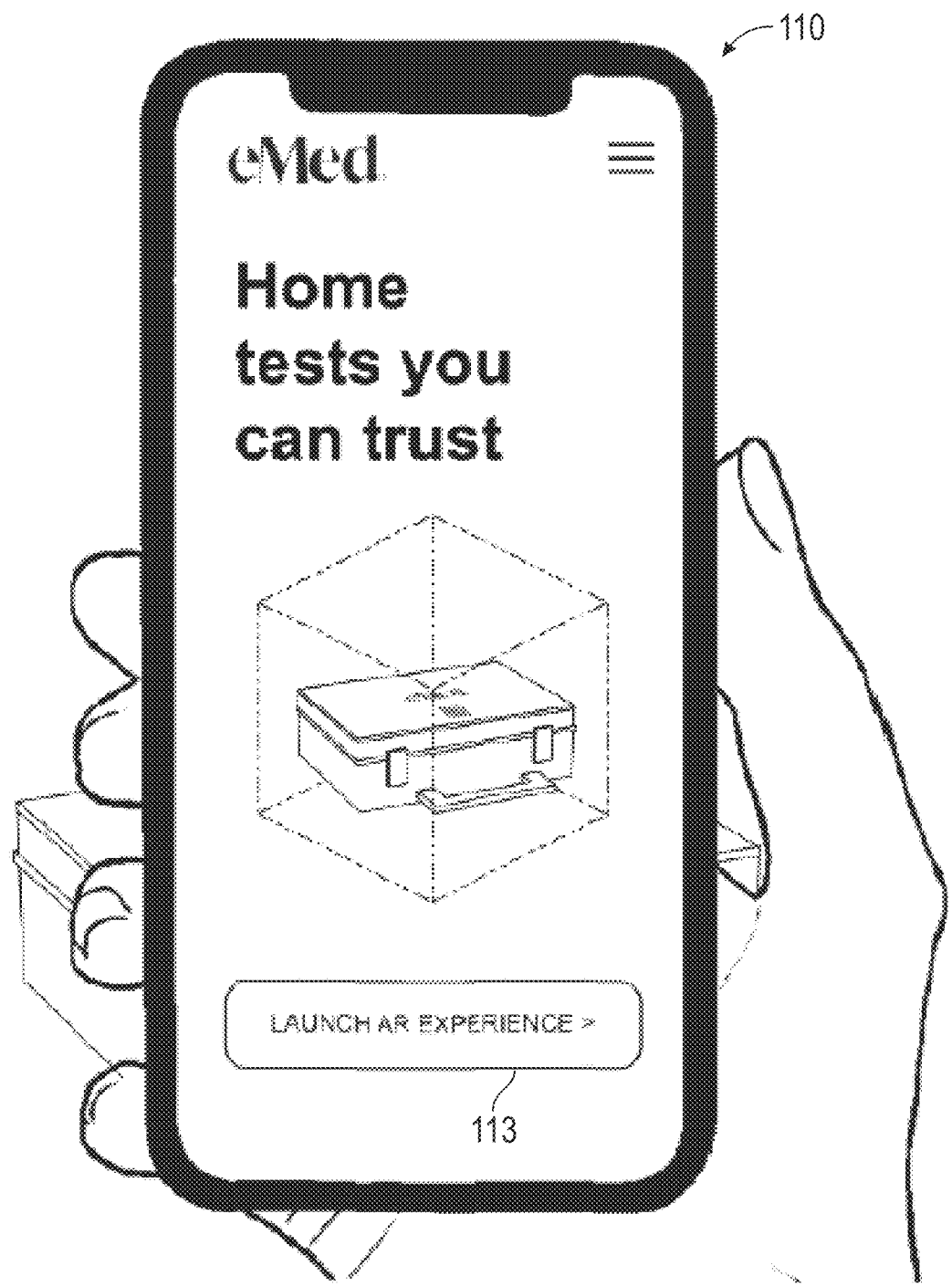
FIG. 2B illustrates an example screen display on the user device that can facilitate user initiation of an augmented reality experience associated with the medical diagnostic test kit container of FIG. 1 for devices configured for augmented reality displays, according to some embodiments described herein.

Clicking or tapping on the image and/or text hyperlink or button 112 can cause a Web browser to launch and navigate the user to a proprietary platform or provider website (e.g., a website controlled and monitored by the provider of the medical diagnostic test kit 100 or operator of a remote health testing and diagnostic platform). FIG. 2B illustrates an example screen display on the user device 110 that can facilitate user initiation of an augmented reality experience associated with the medical diagnostic test kit container 100. The provider or platform website may include a user-selectable option (e.g., a graphical user interface button 113) to launch an augmented reality experience that is implemented by a Web application or software application. The Web application or software application, or portions thereof may be stored on a provider or platform server, a cloud server, and/or local storage of the user device 110.

Augmented Reality Experience Associated with Medical Diagnostic Test Kit Container If the user device 110 is capable of implementing an augmented reality experience, the Web application or software application can be configured to present the user with augmented reality content including graphics and/or alpha-numeric text conveying various information to the user while providing an aesthetically-pleasing enhanced user interaction experience. The information can include, for example:

Information about the contents within the medical diagnostic test kit container 100 (e.g., an overview of the collection of medical diagnostic test kits)

Information about each individual medical diagnostic test in the collection (e.g., condition(s) tested, time to result, test accuracy, whether certified proctors are required, testing materials involved, etc.)

Information about how each individual medical diagnostic test is taken or how it works (e.g., an overview of how the test is to be taken with infographics and/or text demonstrating various steps in the testing process and/or the testing materials involved).

Figure 3A:
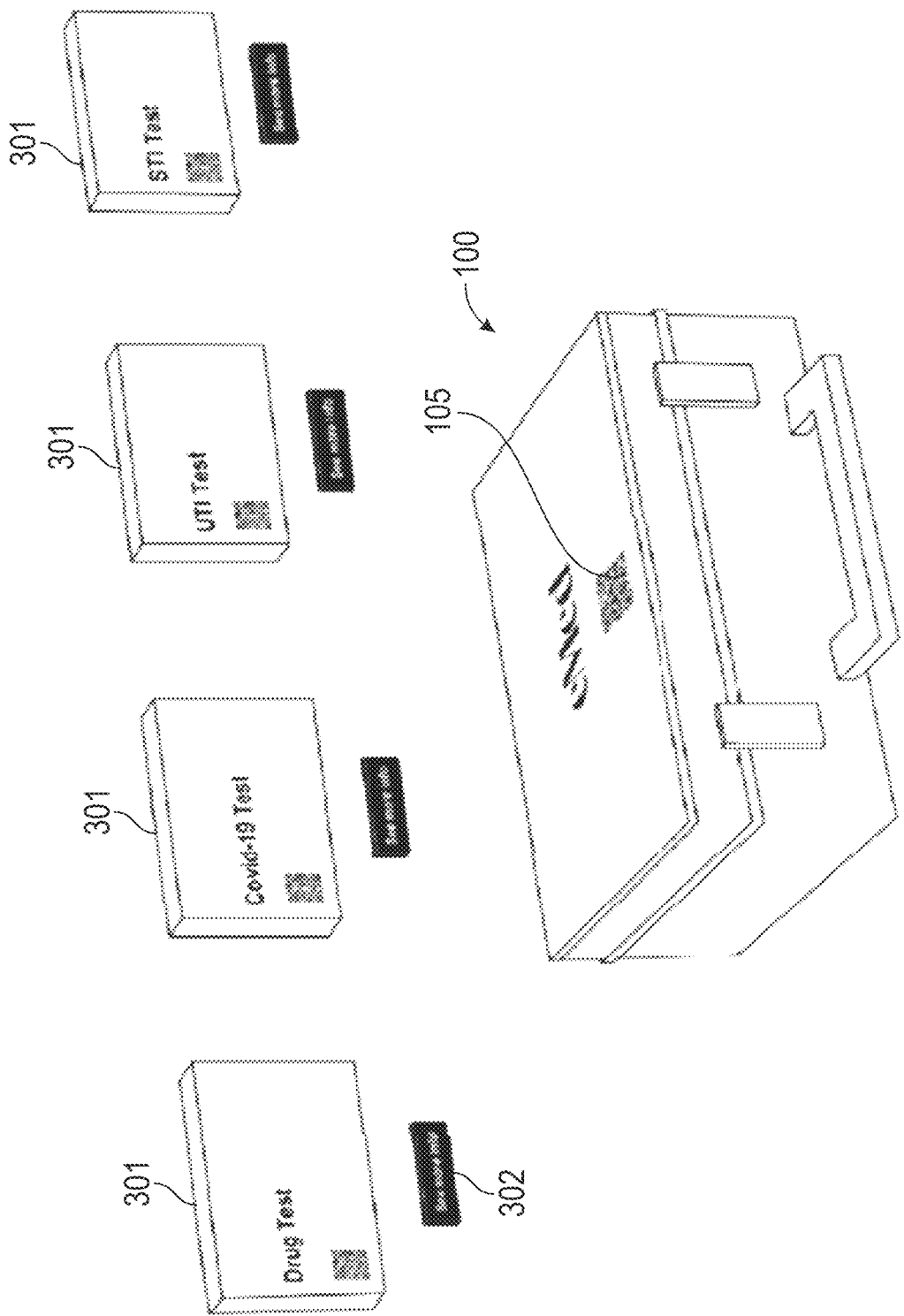
FIG. 3A illustrates an example augmented reality display and graphical user interface according to some embodiments described herein that shows virtual images of the medical diagnostic test kits located within the medical diagnostic test kit container of FIG. 1.
Figure 3B:
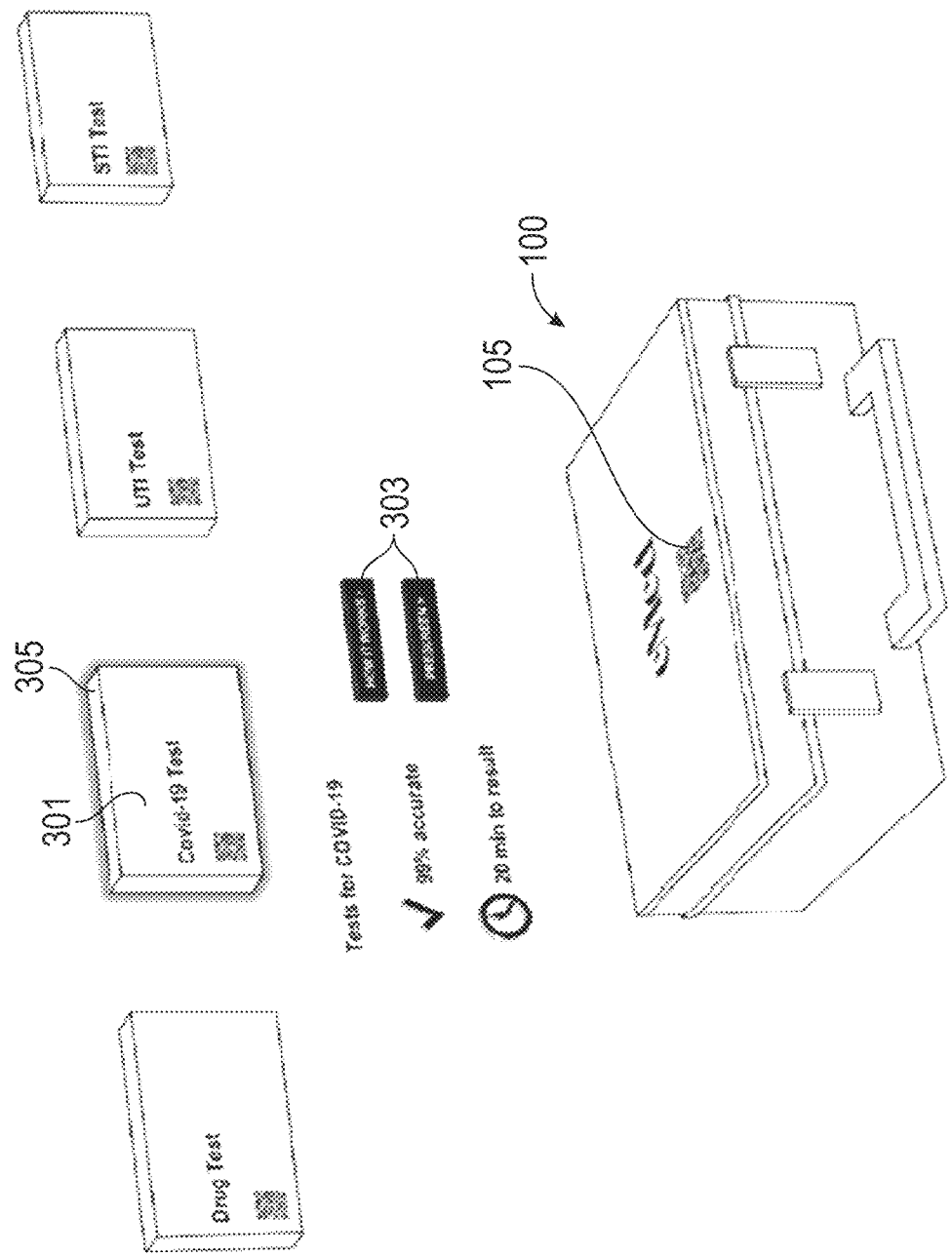
FIG. 3B illustrates an example of a further augmented reality display and graphical user interface following user selection of a particular medical diagnostic test kit in the augmented reality display experience according to some embodiments described herein.

FIGS. 3A-3D illustrate various examples of augmented reality content related to the medical diagnostic test kit container 100 that can be generated and displayed using the camera(s) and display screen 111 of the user device 110. Each of FIGS. 3A-3D may represent a scene as captured using the cameras of user device 110 and overlaid with augmented reality content. For example, the medical diagnostic test kit container 100 as shown in FIGS. 3A-3B may correspond to an image of a real world object. The machine-readable code 105 may serve as a fiducial or anchor point from which a coordinate frame, or registration calibration, for the augmented reality display or presentation can be established. In some implementations, graphics other than the machine-readable code 105 (e.g., a logo, a photo, etc.) on the medical diagnostic test kit container 100 may alternatively or additionally be leveraged to establish the coordinate frame or registration reference point for the augmented reality display or content presentation.

FIG. 3A illustrates an example of augmented reality content that displays the types of medical diagnostic test kits located within a particular medical diagnostic test kit container 100. The augmented reality content includes virtual images 301 of the various medical diagnostic test kits positioned to appear hovering over, or above, the medical diagnostic test container 100 and spaced apart from each other. For example, an augmented reality animation may play that "explodes" the virtual images 301 out of the medical diagnostic test kit container 100 as 3D icons floating in world space above the medical diagnostic test kit container 100. The virtual images 301 include text stating the name of the test, a machine-readable code (e.g., QR code), and one or more user-selectable buttons, images, and/or text icons 302 that, if selected by a user, provide further information about the particular selected medical diagnostic test kit and/or medical diagnostic test. Text on the buttons or icons 302 may include information to indicate that selection by the user will provide more details. The virtual images or icons 301 may also be selectable by the user to provide the user selection input data for further details. Although the buttons or icons 302 are shown in a position below the virtual image of the diagnostic test kit, other positions are contemplated as well. In addition, the virtual images 301 of the medical diagnostic test kits may be displayed in other arrangements or at other locations or positions.

FIG. 3B illustrates an example of a further augmented reality display and graphical user interface following user selection of a particular medical diagnostic test kit in the augmented reality display associated with FIG. 3A. As shown, the augmented reality content includes a shadow or highlighting feature 305 surrounding the virtual image 301 of the selected diagnostic test kit (in this illustration, the COVID-19 test kit). In addition, or as an alternative, the virtual image 301 of the selected medical diagnostic test kit may be enlarged or appear closer to the user than the virtual images of the unselected medical diagnostic test kits.

Further augmented reality content related to the selected medical diagnostic test kit may be displayed below the virtual image 301 of the selected medical diagnostic test kit. For example, the further augmented reality content may include further textual information about the selected medical diagnostic test kit, such as condition(s) tested, test accuracy, and time to result. The further augmented reality content may include a face sheet or card that animates out of the virtual image 301 and is displayed surrounding the virtual image 301 in world space (e.g., above, below, to the right or left). The further augmented reality content may also include additional user-selectable buttons, icons and/or text 303 that, when selected by a user in the augmented reality experience, provide the user with further information about how the selected medical diagnostic test works and/or to initiate a pre-screening survey or test related to the selected medical diagnostic test. Again, the locations and content of the further augmented reality content may vary as desired and/or required.

Figure 3C:
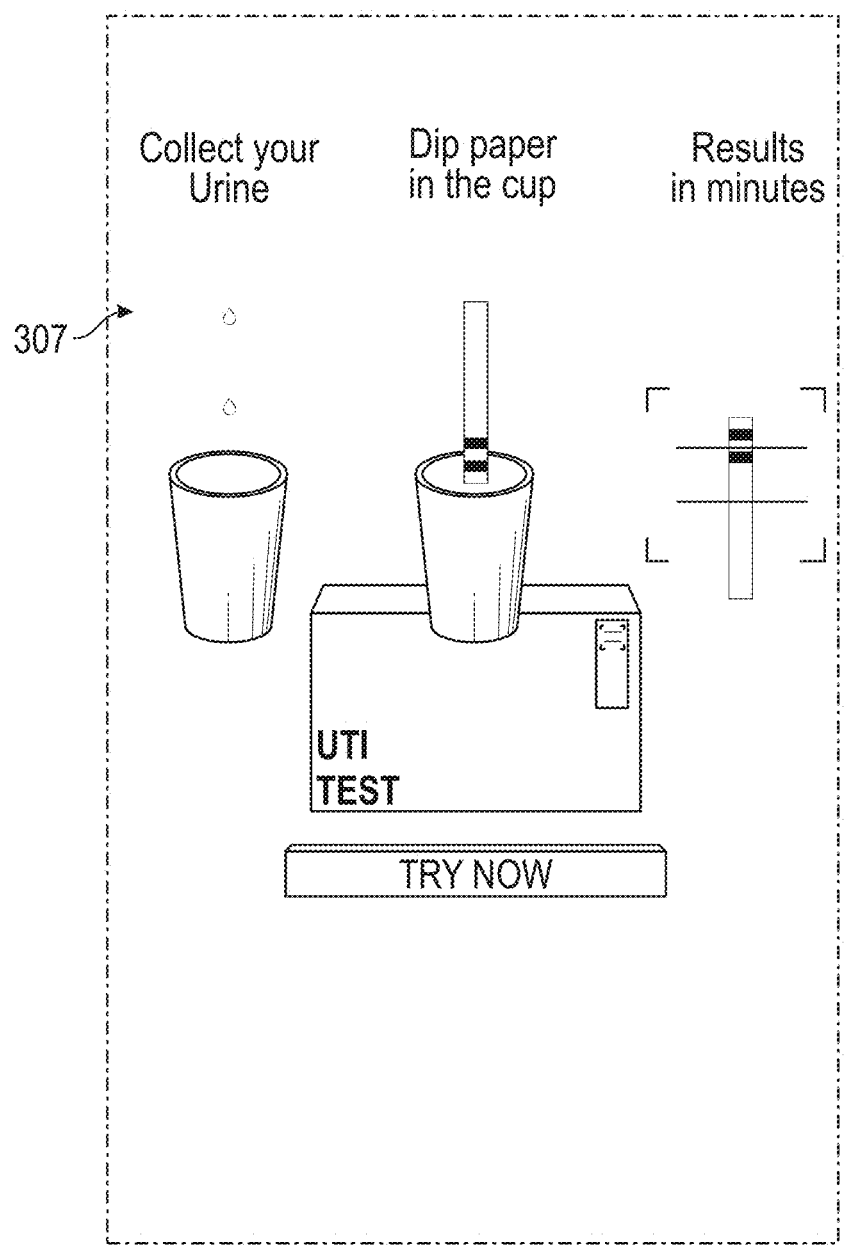
FIGS. 3C and 3D illustrate examples of augmented reality displays and graphical user interfaces showing an overview of steps of a urinary tract infection diagnostic test and a drug test, respectively, contained within the medical diagnostic test kit container, according to some embodiments described herein.
Figure 3D:
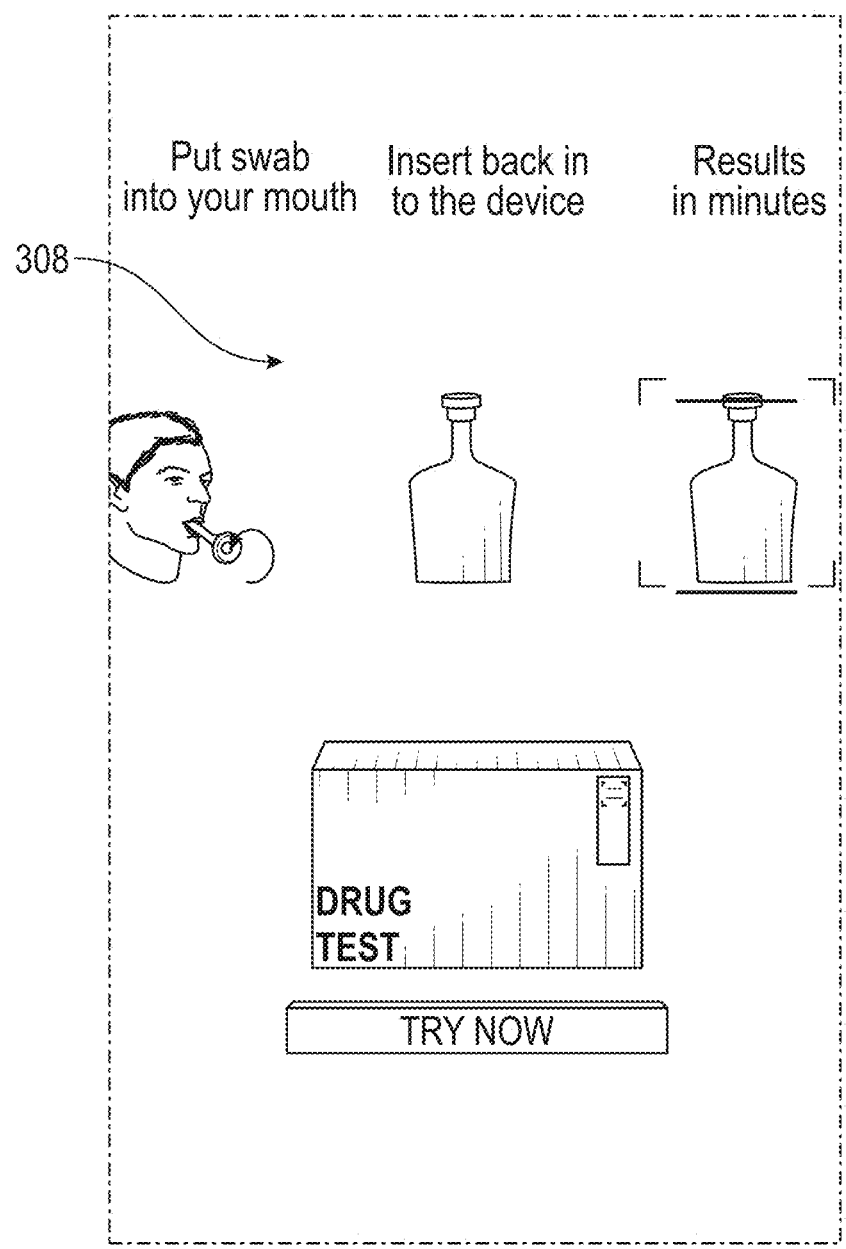

FIGS. 3C and 3D illustrate examples of augmented reality content that includes information about how a particular medical diagnostic test is taken or how it works. This further augmented reality content may be generated upon receipt of user input data indicating a request for further details or information. FIG. 3C illustrates example augmented reality infographics 307 showing an overview of the steps involved in a urinary tract infection (UTI) test and FIG. 3D illustrates example augmented reality infographics 308 showing an overview of the steps involved in a drug test. The overview of steps may be presented in an augmented reality video, animation, or still images. The infographics 307, 308 may be displayed at various positions or locations with respect to the medical diagnostic test kit container 100.

Figure 3E:
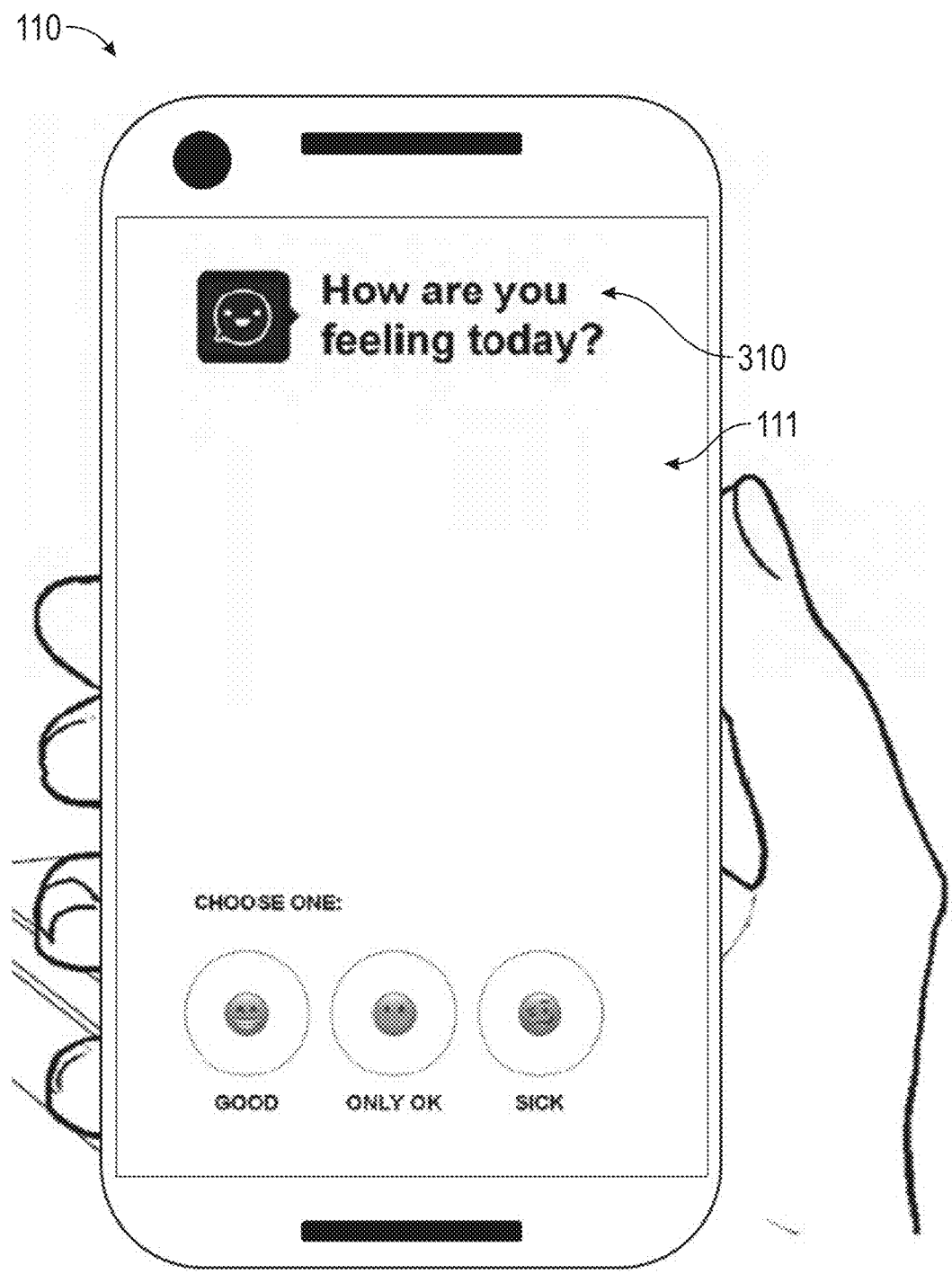
FIG. 3E illustrates an example of a 2-D display and graphical user interface that may be generated to facilitate a prescreening process to be completed via user interaction on a user device (e.g., mobile phone or tablet) prior to initiating a particular at-home medical diagnostic test according to some embodiments described herein.

FIG. 3E illustrates an example of a 2-D display and graphical user interface 310 that may be generated and presented on the display screen 111 of the user device 110 (e.g., personal computer, a cellular phone, a pair of smart glasses, a smartwatch, a smartphone, a laptop, a tablet computer, an e-reader device, an audio player, or another device capable of connecting to and communicating over a network, whether wired or wireless) if the user selects user-selectable content in the augmented reality experience to initiate a prescreening survey or chatbot. The illustrated display may be the first question of several questions that are completed via user interaction involving graphical user interfaces on a user device (e.g., mobile phone or tablet) prior to initiating a particular at-home medical diagnostic test.

The prescreening survey or test may help determine whether the user should take the selected medical diagnostic test. Although the user may obtain the medical diagnostic test kit container 100 without a prescription (and thus may take any of the medical diagnostic tests in the diagnostic test kit container 100 whenever he or she feels like it), it may not be a worthwhile use of a particular medical diagnostic test if the user is not exhibiting the corresponding symptoms. In some implementations, therefore, as a user experience enhancement, the prescreening surveys can be used to help users avoid wasting medical diagnostic test kits in situations where usage is deemed unnecessary.

In some implementations, the health testing and diagnostic platform (e.g., platform 1902 shown in FIG. 19) may receive user input of survey answers from the user device 110 and attempt to pre-qualify the user based on available guidelines, such as government stipulated testing requirements. In some implementations, information can be gathered about the user that may facilitate various functionality of the health testing and diagnostic platform. For example, the user's identity can be verified. Verification of the user's identity can occur in various ways as described further below. In some implementations, verification of the user's identity comprises checking the user's ID (e.g., driver's license or passport). In some implementations, the user's identity is verified using biometrics. Additionally, information about the user may be gathered at this stage which may facilitate matching the user to a proctor within the system in a manner that improves the efficiency of the system.

In addition to checking symptoms, the user patient may also be prompted by the platform to complete a medical questionnaire to provide additional information regarding the patient's condition, health history, and/or other relevant information. In some implementations, the information gathered can include information regarding the user patient's travel history and/or future travel plans. For example, the process can include presenting the user with questions regarding their travel plans (e.g., "Are you planning to travel into or out of the United States within the next 72 hours?").

Figure 4A:
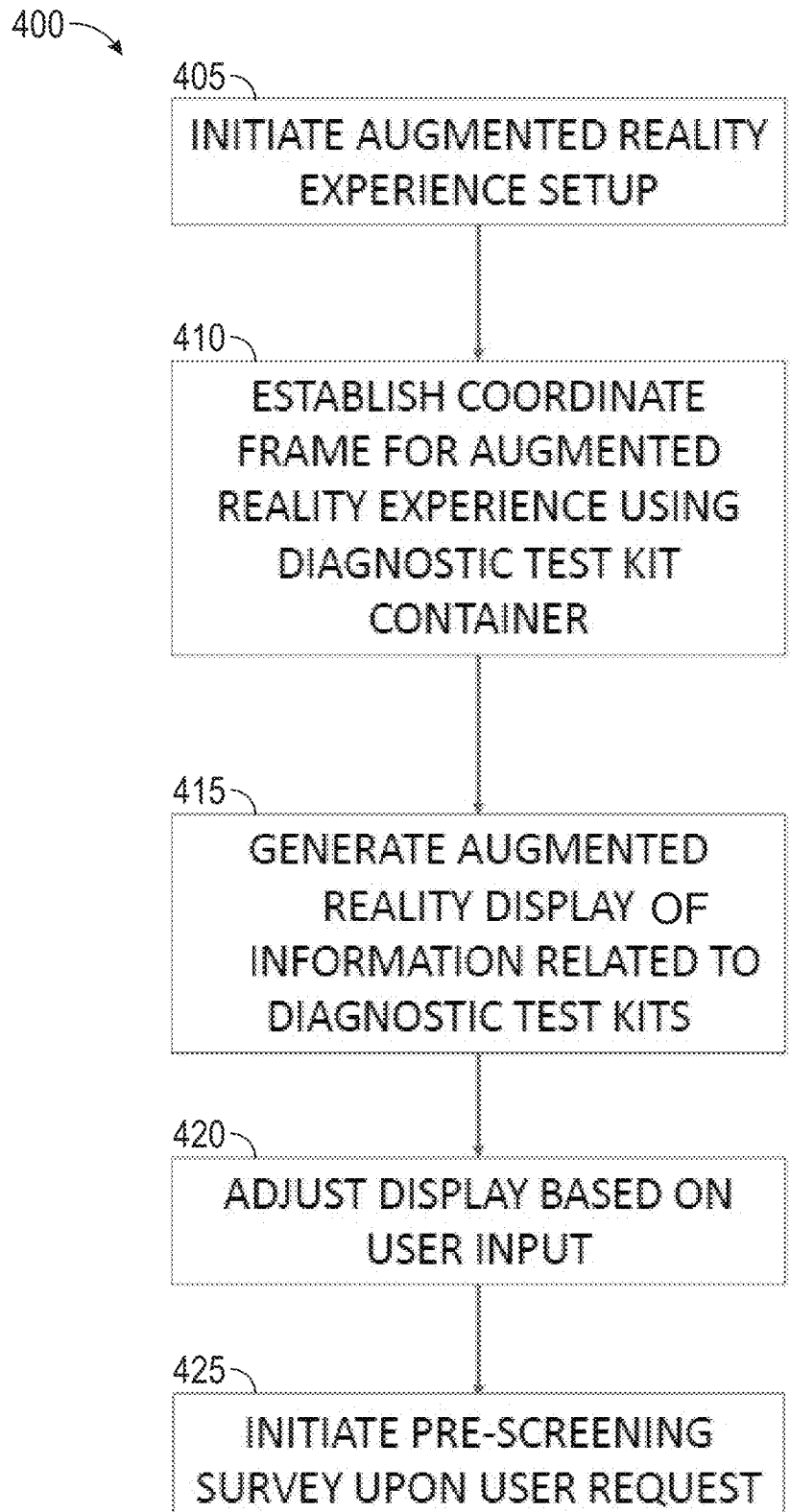
FIGS. 4A and 4B illustrate an example flowchart of a method of providing an augmented reality experience for a user interacting with the medical diagnostic test kit container of FIG. 1 according to some embodiments described herein.
Figure 4B:
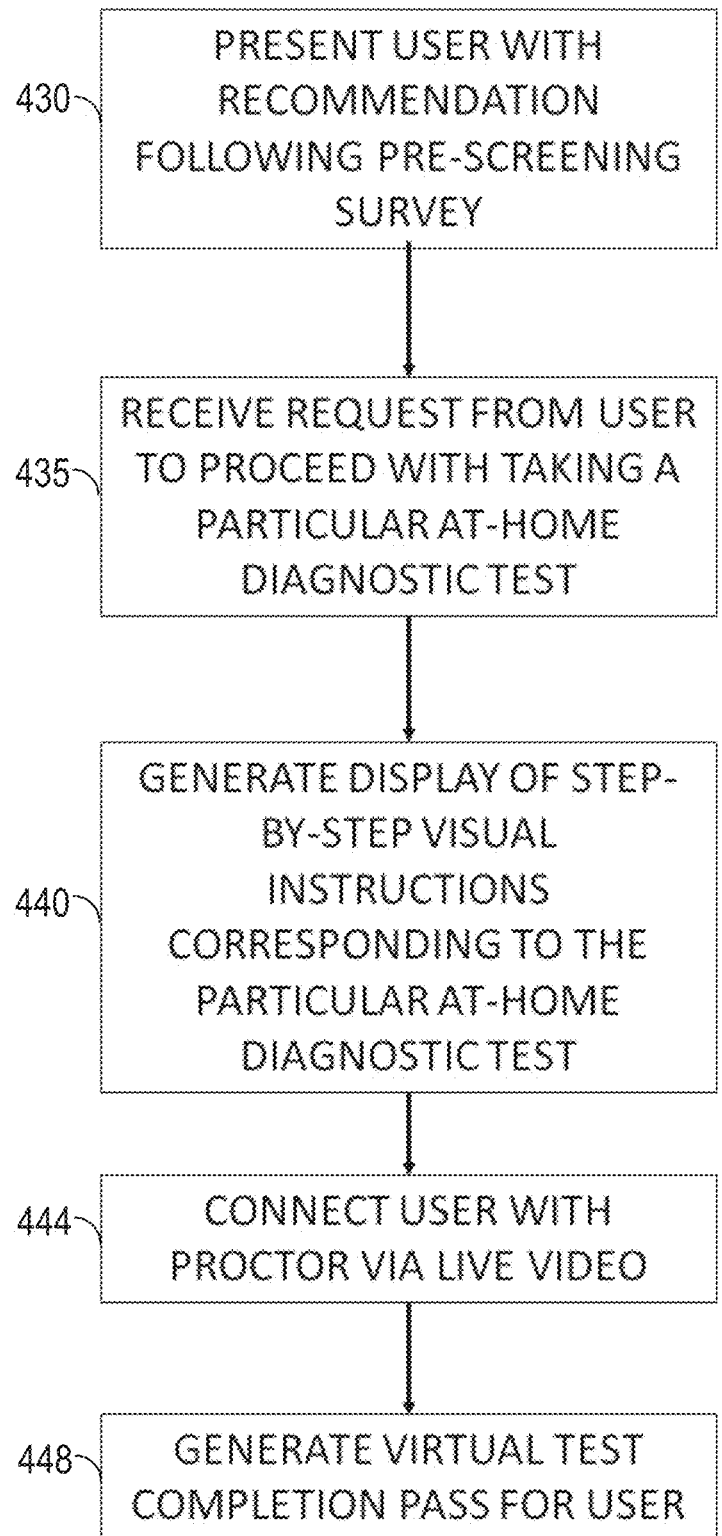

FIGS. 4A and 4B illustrate an example flowchart of a method 400 of providing an augmented reality experience for a user interacting with the medical diagnostic test kit container 100. At Block 405, a remote health testing and diagnostic platform (e.g., software application or Web application upon execution of program instructions stored on a computer-readable storage medium, such as platform 1902 shown in FIG. 19) initiates an augmented reality experience setup associated with the medical diagnostic test kit container 100. The initiation of the augmented reality experience setup at Block 405 may be triggered by receipt of user input data (e.g., the user selection of a selectable graphical user interface button or other content on a platform webpage or Web application) that indicates a desire to launch an AR experience associated with the medical diagnostic test kit container 100.

For example, to get to this point, a user may scan the machine-readable code 105 (e.g., QR code) on the exterior of the medical diagnostic test kit container 100 using a camera of the user device 110 (e.g., smartphone or tablet), as shown in FIG. 2A. Then, in response to the user scanning the machine-readable code 105, the user device 110 provides the user with an opportunity to proceed to a URL (webpage) that is associated with the machine-readable code 105. Receiving user input data indicating that the user would like to proceed to the URL (webpage) can trigger the user device 110 to proceed to the URL (webpage), which in turn provides the user with the opportunity to launch the AR experience, as shown in FIG. 2B.

At Block 410, the remote health testing and diagnostic platform (e.g., software application or Web application) establishes a coordinate frame for the augmented reality experience associated with the medical diagnostic test kit container 100. The platform may use the machine-readable code 105 and/or other graphics or portions of the medical diagnostic test kit container 100 to establish the coordinate frame, or registration.

At Block 415, augmented reality content associated with the medical diagnostic test kits contained within the medical diagnostic test kit container 100 is displayed or overlaid on real-time, real-world images obtained by the camera(s) of the user device 110, as shown for example in FIG. 3A. At Block 420, the augmented reality content and display is adjusted based on receipt of user input data. For example, the augmented reality content is adjusted to indicate or highlight a selected diagnostic test kit and/or to display additional information related to a particular diagnostic test kit, as shown in FIGS. 3B-3D. At Block 425, a prescreening survey or questionnaire is optionally initiated upon user request (e.g., upon the user clicking on, tapping, or touching via touchscreen interface a "Prescreening" virtual button 302 in the augmented reality display of FIG. 3B).

The method 400 may continue following the prescreening survey. Turning to FIG. 4B, the method 400 may proceed with facilitating completion of one of the at-home medical diagnostic tests using a medical diagnostic test kit within the medical diagnostic test kit container 100. At Block 430, in some implementations, upon completing the prescreening survey, a recommendation may be generated by the health testing and diagnostic platform and presented to the user concerning whether the user should take the particular medical diagnostic test. The user may also be presented with an opportunity to indicate that he or she would like to proceed with taking the particular medical diagnostic test, regardless of the recommendation. At Block 435, a request is received by the health testing and diagnostic platform to proceed with taking a particular at-home medical diagnostic test (e.g., a virtual graphical user interface button or other user-selectable image, icon, and/or text link presented on a display screen 111 of the user device 110).

At Block 440, augmented reality content may be generated and displayed on the user device 110 that includes step-by-step visual instructions and/or infographics corresponding to the particular at-home medical diagnostic test. Example augmented reality content that may be overlaid on real-time, real-world images of the user and/or diagnostic test kit obtained from front-facing and/or rear-facing cameras of the user device 110 is shown, for example, in FIGS. 8A-8J, 9A-9F, and 10A-10H. In some implementations, the step-by-step visual instructions and/or infographics may be presented in a 2D format and not as AR content.

At Block 444, the remote health testing and diagnostic platform may facilitate connection of the user with a proctor via live video (e.g., over the Internet or cellular telecommunications network) using the user device if the particular medical diagnostic test requires a proctor to observe at least a portion of the test administration for certification purposes. In some embodiments, the user may be connected with a proctor or other personnel while performing the testing procedure at block 440 at the user's request (e.g., to receive assistance with performing a specific step, etc.). In some embodiments, at block 444 a proctor or other personnel may observe at least a portion of the test administration for certification purposes without engaging in a live video connection with the user. At Block 448, the remote health testing and diagnostic platform may optionally generate a virtual, or digital, test completion pass for the user, as will be described further below. In some implementations, block 448 may additionally or alternatively include one or more steps for procuring prescription medicine or otherwise receiving treatment, such as one or more of the steps described below with reference to FIGS. 15-17B.

Medical Diagnostic Test Kit Container Inventory Tracking

Figure 4C:
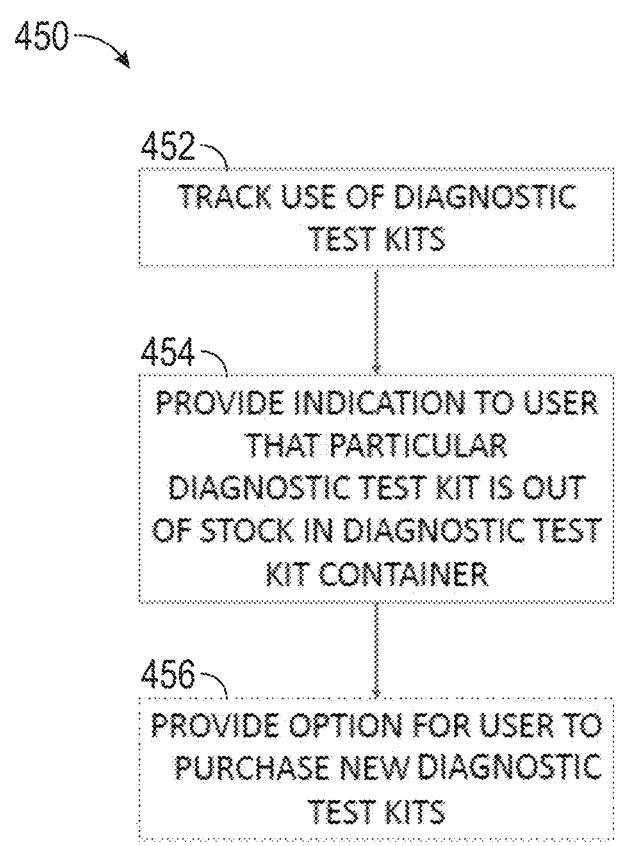
FIG. 4C illustrates an example flowchart of a method of tracking inventory of medical diagnostic test kits within the medical diagnostic test kit container and providing notifications to a user when inventory is low according to some embodiments described herein.

FIG. 4C illustrates an example flowchart of a method 450 of tracking inventory of medical diagnostic test kits within the medical diagnostic test kit container 100 and providing notifications to a user when inventory is low. At Block 452, the remote health testing and diagnostic platform (e.g., platform 1902 shown in FIG. 19) tracks use of medical diagnostic test kits in the medical diagnostic test kit container 100. The remote health testing and diagnostic platform may be pre-programmed with the initial start count or tally of each type of medical diagnostic test kit in the medical diagnostic test kit container 100 or the user may indicate or provide the initial start count or tally. The remote health testing platform may track inventory, for example, by decreasing a count or tally upon user indication of initiation of a particular medical diagnostic test. Of course, the count or tally may be decreased at other stages of the test taking process as well. For example, the user may be requested to scan a machine-readable code located on packaging of a particular medical diagnostic test kit once the diagnostic test is completed using that kit and the scanning of the machine-readable code may cause the remote health testing platform tracking program to decrease the count or tally for that type or category of medical diagnostic test kit. In some embodiments, this information may be stored and managed in association with the user's account.

At Block 454, the remote health testing and diagnostic platform may provide an indication to a user (via an alert notification, text message, email message or other notification means) that a particular category or type of medical diagnostic test kit(s) is running low or has been completely depleted and is in need of a resupply. In some implementations, the remote health testing platform may provide the indication by presenting a modified representation of the virtual medical diagnostic test kit image in the augmented reality display. For example, an out-of-stock medical diagnostic test kit may be presented in gray or other different color, as an outline, with highlighting, and/or with one or more graphics (e.g., strikethrough symbol, letter X, or circle with a diagonal line through it) indicating that the medical diagnostic test kit container 100 no longer includes any of the particular medical diagnostic test kit. The method 450 may optionally include (at Block 456) providing an option for a user to purchase additional medical diagnostic test kits upon receipt of the indication (e.g., alert or other notification). The option may be provided via a hyperlink or user-selectable graphical icon, button, or image to direct the user to a URL or Webpage or e-commerce portal to facilitate purchasing of additional medical diagnostic test kits. In some implementations, the option may be presented using an inline HTML iframe element.

At-Home Medical Diagnostic Test Kits

Figure 5:
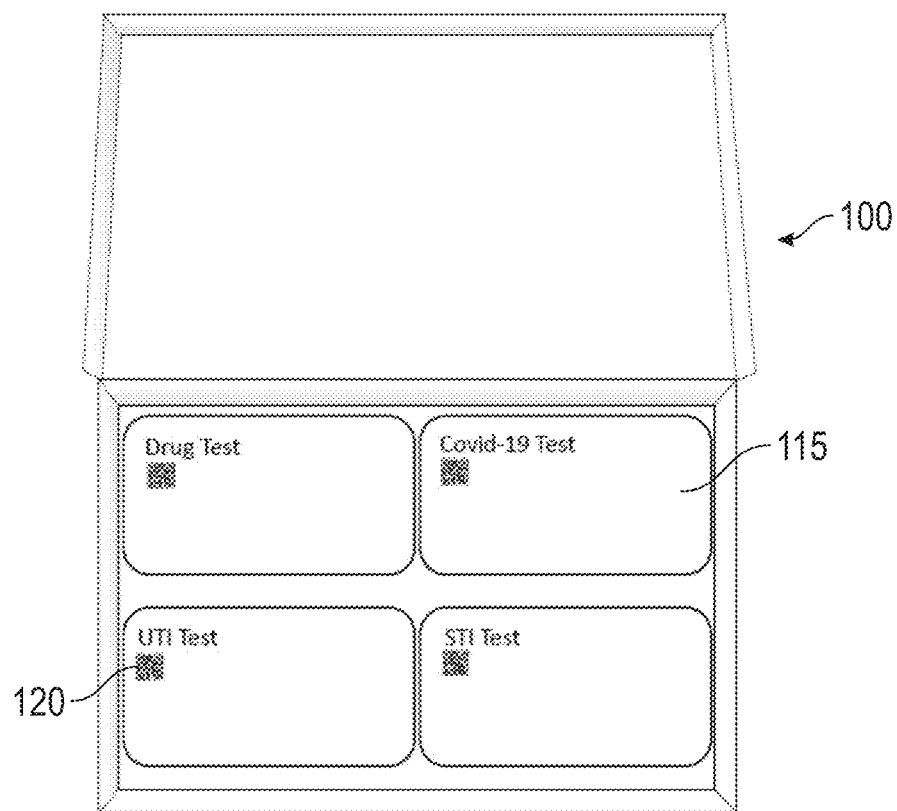
FIG. 5 illustrates examples of items (e.g., at-home medical diagnostic test kits) that may be included in the medical diagnostic test kit container or package of FIG. 1 according to some embodiments described herein.

FIG. 5 illustrates examples of items (e.g., at-home medical diagnostic test kits 115) that may be included in the medical diagnostic test kit container or package 100. As shown, the particular medical diagnostic test kit container 100 includes one or more drug test kits, one or more COVID-19 test kits, one or more UTI test kits, and one or more sexually transmitted infection (STI) test kits. Different diagnostic test kit containers 100 may include different types and amounts of test kits 115 geared toward particular households, individuals, or other groups or facilities, depending on needs, lifestyles, or circumstances. The number of total test kits 115 may vary (e.g., 2 test kits, 3 test kits, 4 test kits, 5 test kits, 6 test kits, 7 test kits, 8 test kits, 9 test kits, 10 test kits, more than 10 test kits).

As shown in FIG. 5, in some implementations, each of the medical diagnostic test kits 115 inside the medical diagnostic test kit container 100 may bear its own machine-readable code 120 (e.g., QR code, AR code, PDF417 code, bar code, datamatrix code, Aztec code). The machine-readable codes 120 on the individual medical diagnostic test kits 115 may be positioned on an external surface of packaging of the diagnostic test kit 115 but may alternatively be positioned in locations other than the location illustrated in FIG. 5. In some implementations, the machine-readable code 120 that is scanned may be printed on one or more of the diagnostic test kit materials (rather than the box or other packaging). In some implementations, other types of machine-readable codes (e.g., bar codes, etc.) can be used in addition to or in place of the illustrated QR codes.

The external surface of the packaging of the medical diagnostic test kit 115 may also include graphics, logos, photos, or textual content in addition to the machine-readable codes 120. Multiple machine-readable codes 120 may be positioned at different locations on each medical diagnostic test kit packaging in some implementations. In some implementations, one or more computer vision techniques may be leveraged to identify test kit materials and packaging instead of or in addition to the QR code scanning techniques.

In accordance with several implementations, scanning of a machine-readable code 120 on a particular medical diagnostic test kit 115 may cause the user device 110 to automatically initiate an augmented reality experience associated with the particular medical diagnostic test kit 115. Again, the machine-readable code 120, alone or in combination with other graphics or portions of the medical diagnostic test kit 115 may serve as a fiducial reference or registration point for establishing a coordinate frame for the augmented reality content presentation in some implementations. In some implementations, simultaneous localization and mapping (SLAM) or other autonomous control methods or techniques may be used to calculate a spatial relationship between the user device 110 and multiple keypoints.

Figure 6:
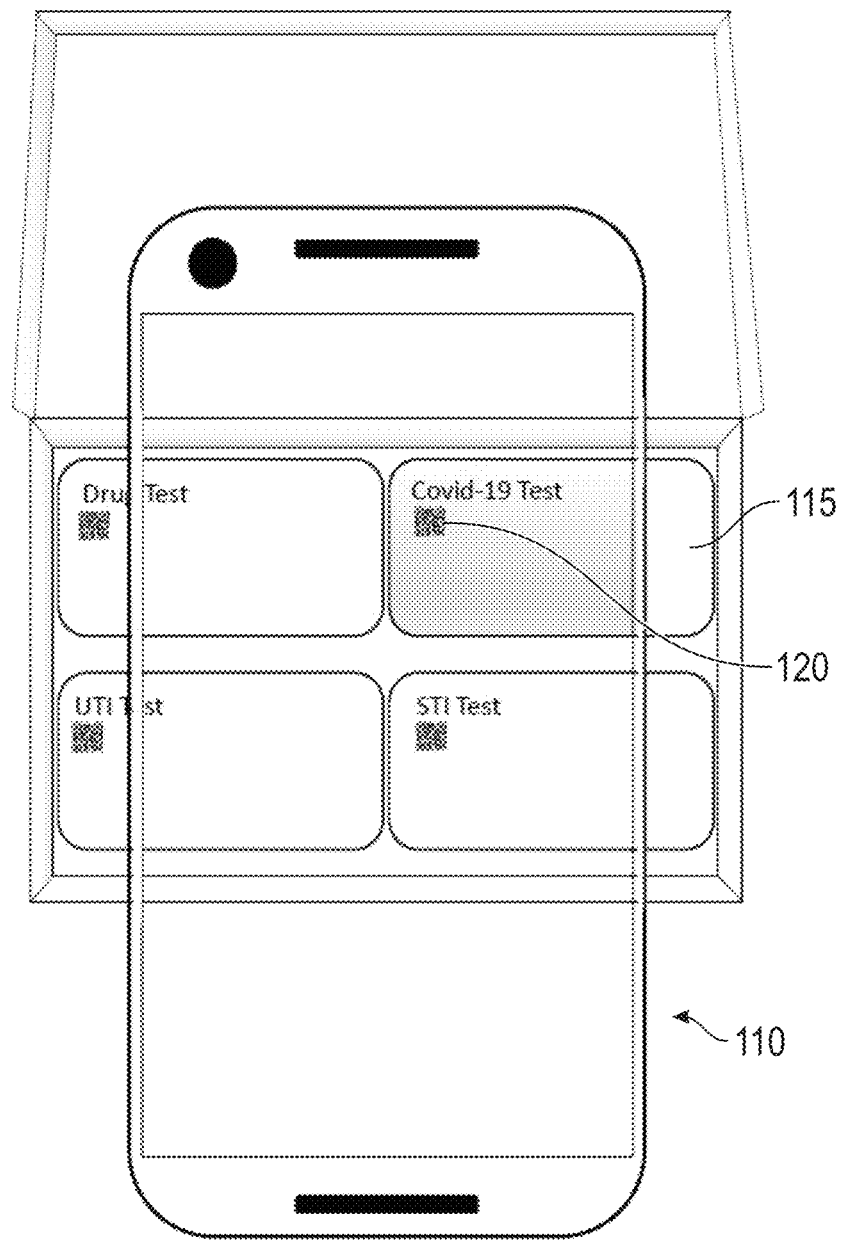
FIG. 6 illustrates an example of a user scanning a machine-readable code located on a particular medical diagnostic test kit using a mobile phone having a built-in camera according to some embodiments described herein.

FIG. 6 illustrates an example of a user scanning a machine-readable code 120 located on a particular medical diagnostic test kit 115 (in this instance, a COVID-19 test kit) using a user device 110 (e.g., mobile phone) having one or more built-in cameras. The machine-readable codes 120 (e.g., QR codes, AR codes) may be scanned while a particular medical diagnostic test kit 115 remains within the medical diagnostic test kit container 100 or after removal of the particular medical diagnostic test kit 115.

Figure 7:
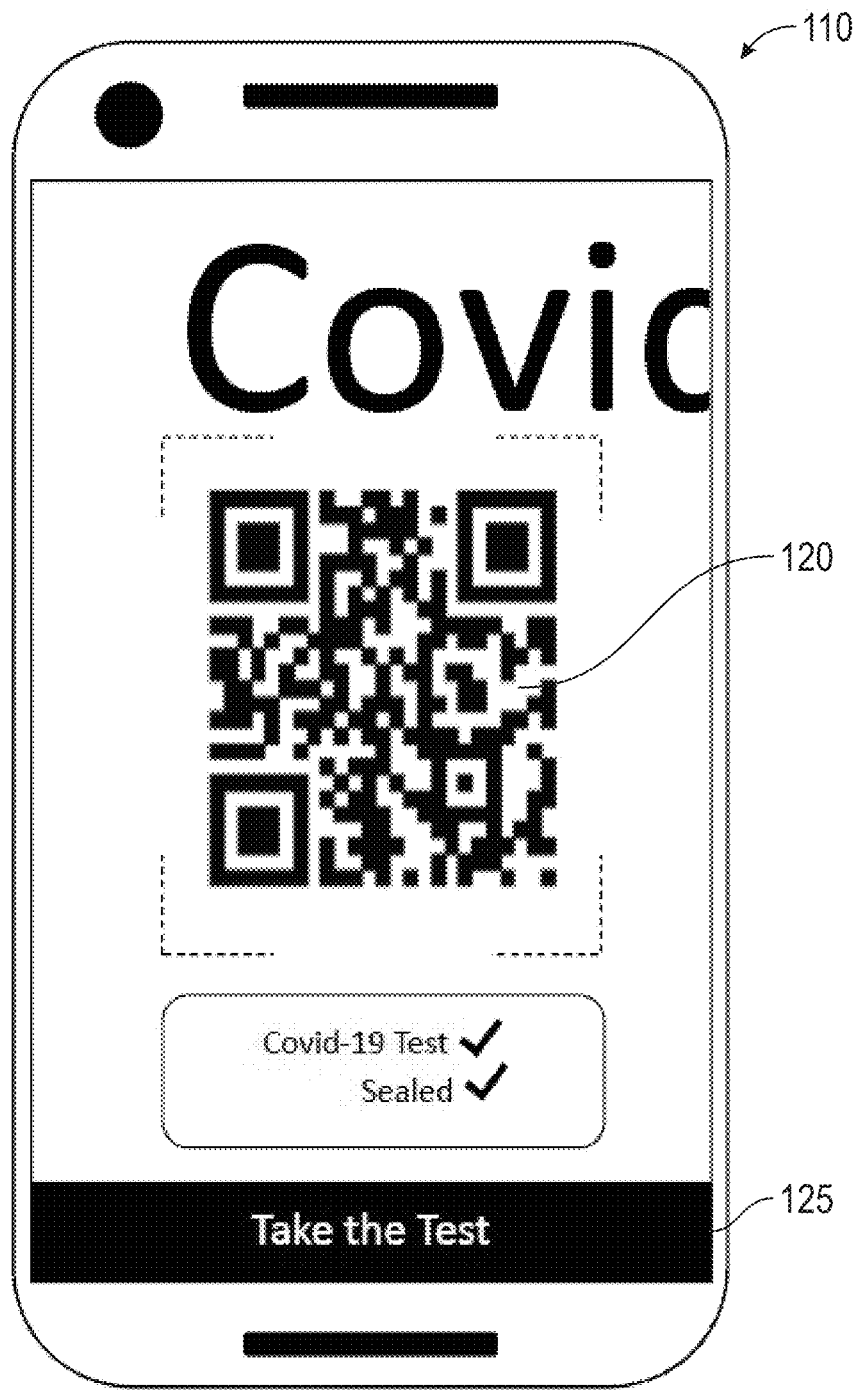
FIG. 7 illustrates an example of a graphical user interface screen that may be displayed on a portable user device upon scanning of a machine-readable code of a particular medical diagnostic test kit according to some embodiments described herein.

FIG. 7 illustrates an example of a graphical user interface screen that may be displayed on a user device 110 (e.g., mobile phone, smartphone, or tablet) upon scanning of the machine-readable code 120 of a particular medical diagnostic test kit 115. As shown, the graphical user interface may include a user-selectable button 125 or other graphic or textual link that provides the user with an option to initiate taking the test associated with the particular medical diagnostic test kit 115 for which the machine-readable code 120 has been scanned. Upon receipt of a user indication or user input data (e.g., pressing of the user-selectable button 125 on the graphical user interface), the augmented reality content may transition to the step-by-step guide to completion of the medical diagnostic test using the medical diagnostic test kit 115.

Augmented Reality (AR) Based Testing Guidance for At-Home Medical Diagnostic Test Kits In some implementations, the remote health testing and diagnostic platform (e.g., platform 1902 shown in FIG. 19) may provide augmented reality (AR) based testing guidance to users and/or proctors. Because users and proctors generally interact with the platform using devices that include displays, AR-based testing guidance can be overlaid onto the displays to facilitate testing and/or proctoring. For example, graphics can be overlaid onto a live video feed of the medical diagnostic test kit (as provided by one or more cameras of the user device 110) to help the user properly open, set up, utilize, and/or dispose of the test kit 115. As a more specific example, in some tests, the user may be required to deposit drops of a solution onto a certain portion of a test card (see, for example, FIG. 8D, described below). The user can be instructed to position the test kit 115 such that it is within the view of the camera and can be viewed on the user's screen. Augmented reality guidance (infographics, images and/or text) indicating where to deposit the drops can be overlaid onto the user's screen to indicate where the user should place the drops of solution. As another example, when the user needs to access a swab within the test kit 115, the location of the swab can be highlighted using AR on the user's screen.

AR-based guidance can be implemented in a variety of different ways. In the illustrated examples herein, a user accesses the remote health testing and diagnostic platform using a user device 110 (e.g., smartphone or tablet). In this example, the user device 110 includes both forward facing and rearward facing cameras. One or both of these cameras can be used during a testing procedure to capture images of, for example, the user and/or a test kit 115 used during the testing procedure. Further, the images captured by the forward and/or rearward facing cameras can be displayed to the user on a display 111 of the user device 110. Moreover, AR-based guidance can be added to the images displayed to the user to facilitate and improve the testing experience. Examples of AR-based guidance that can be displayed to the user are shown in FIGS. 8A-H, described below.

Figure 8A:
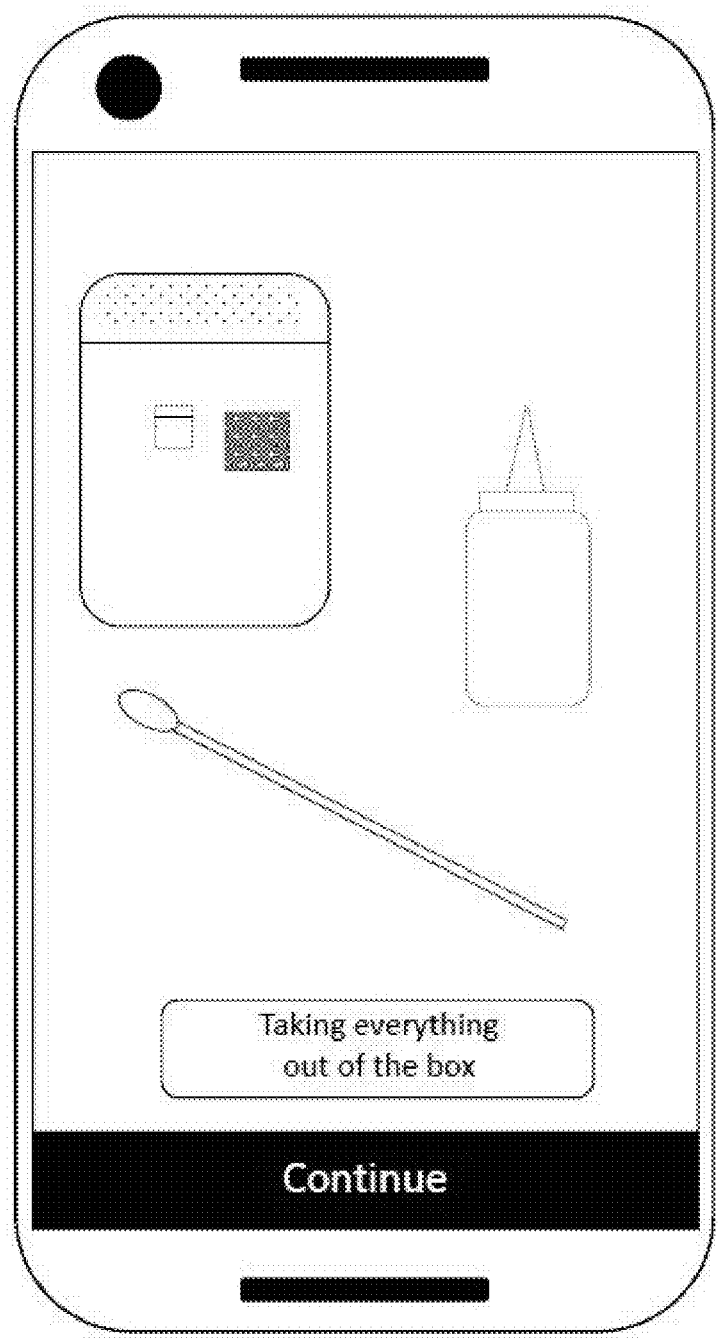
FIGS. 8A-8J illustrate a series of example screen displays that can be displayed to a user to guide the user through the steps of administering an at-home COVID-19 diagnostic test according to some embodiments described herein.
Figure 8B:
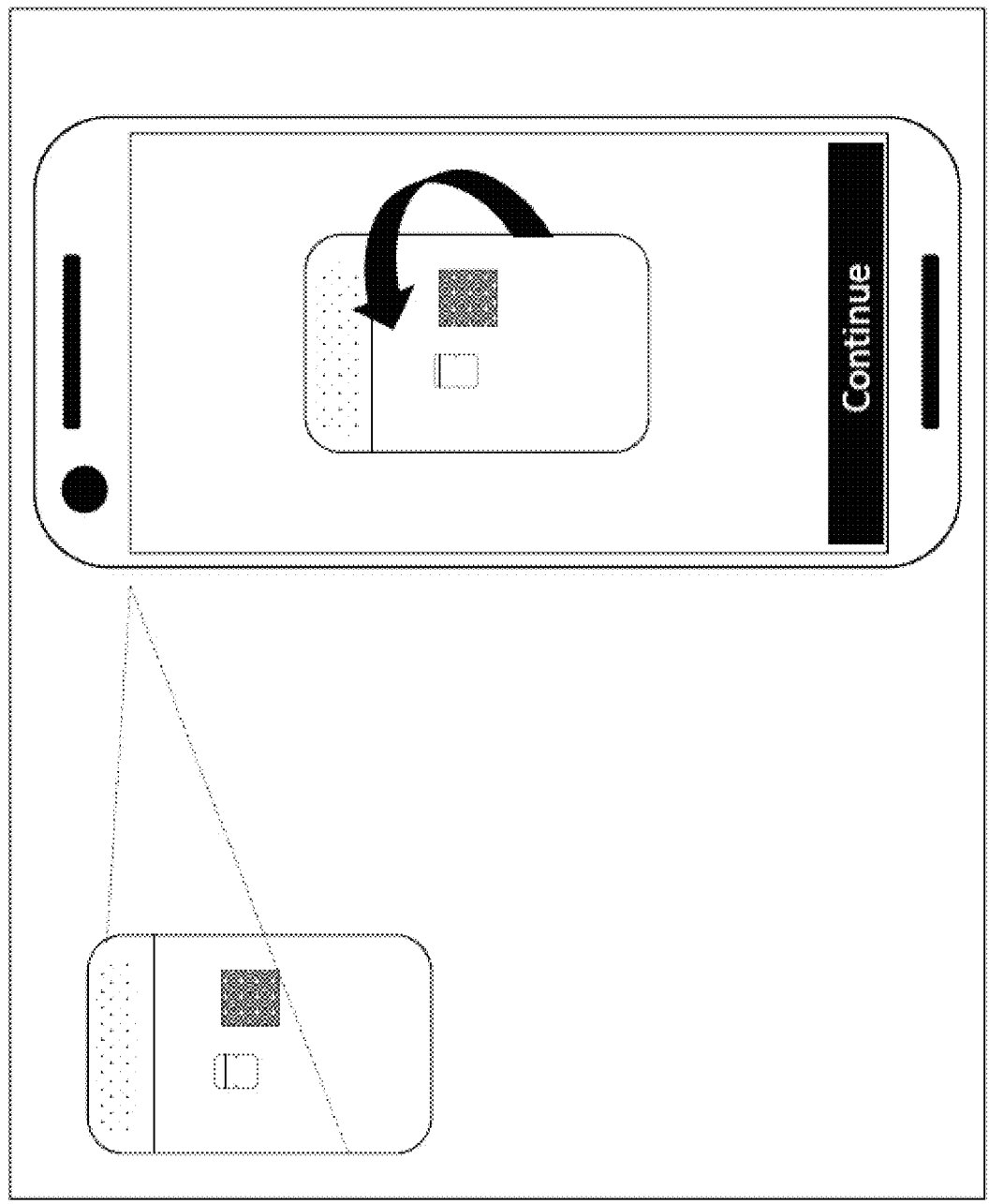
Figure 8C:
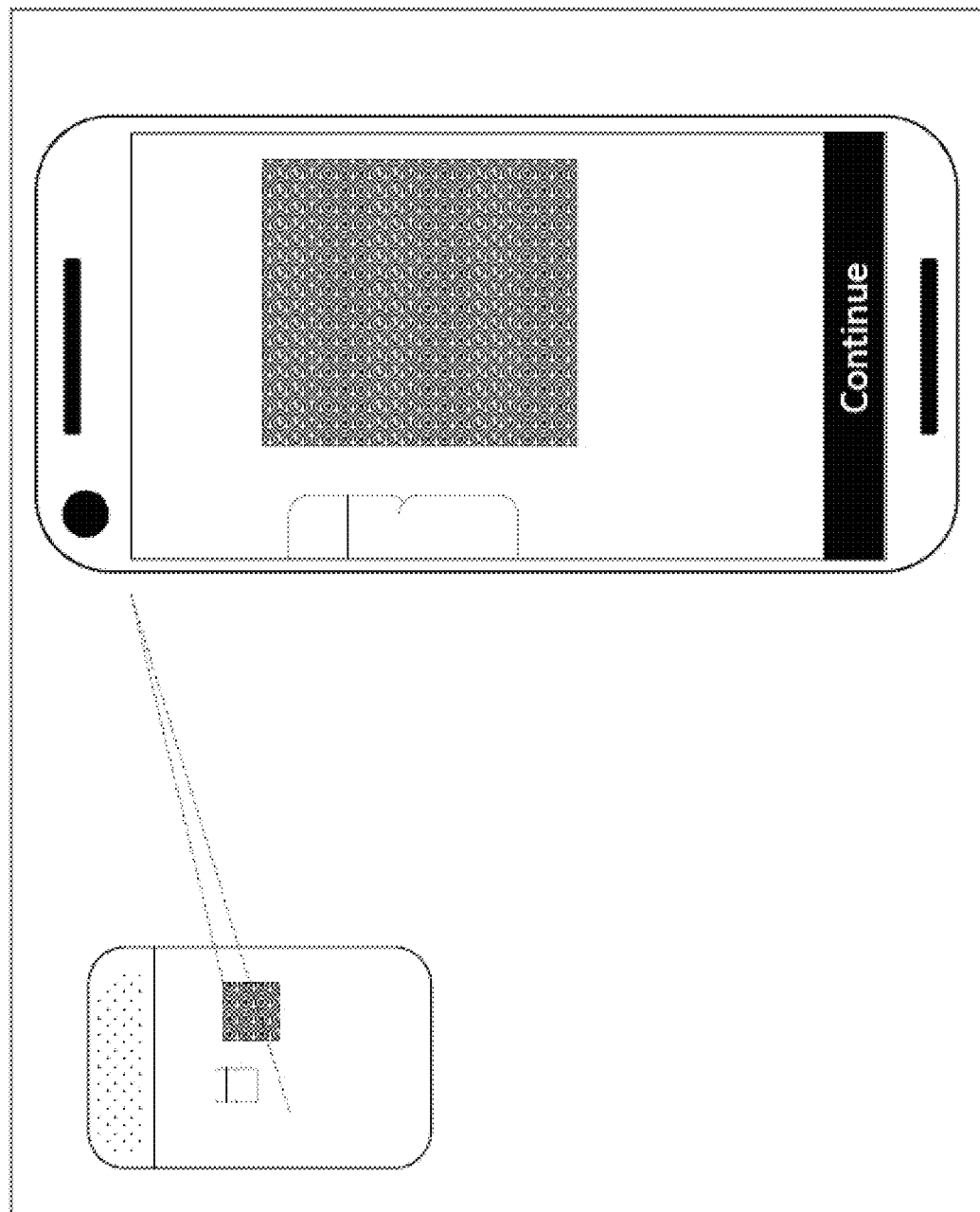

FIGS. 8A-8J illustrate a series of example screen displays that can be displayed to a user to guide the user through the steps of completing an at-home COVID-19 diagnostic test according to some embodiments described herein. The screen displays may include augmented reality display content that is overlaid on real-time, real-world camera images of components or portions of the medical diagnostic test kit 115 and/or the user. As shown, the screen displays may also include infographics, text instructions, and user-selectable content (e.g., buttons) to facilitate receipt of user indication of completion of each step of the testing process in order to continue on to the next step. FIG. 8A includes a display that instructs the user to take the contents out of the COVID-19 test kit. FIG. 8B includes a display that instructs the user to flip over the COVID-19 test kit. The augmented reality content may include a virtual arrow image overlaid on the real-world image of the test kit. FIG. 8C includes a display that is zoomed in on a certain portion of the test kit, potentially for verification that the test kit is sealed and has not been used or tampered with prior to administration of the test or to scan a machine-readable code on the test kit.

Figure 8D:
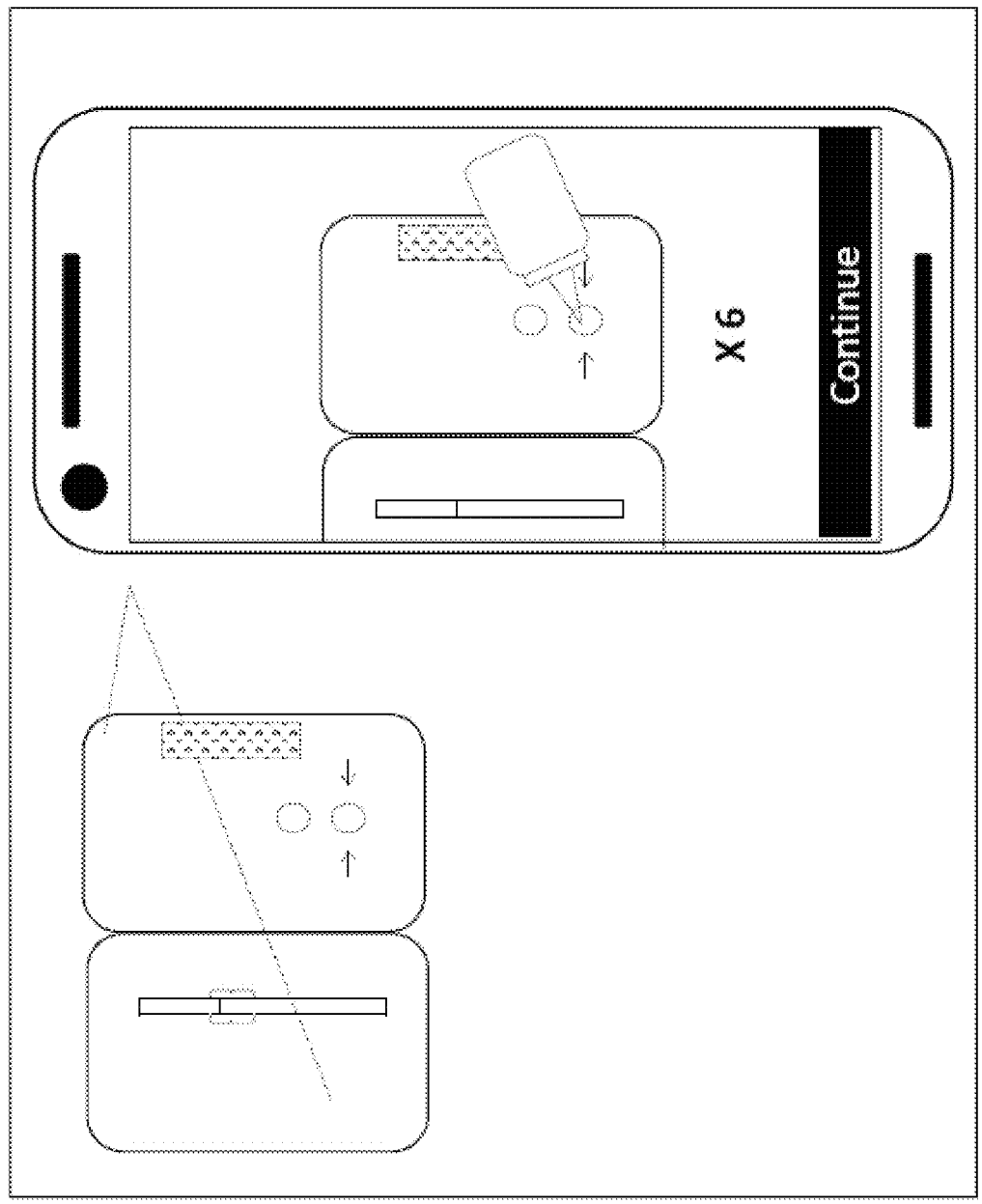
Figure 8E:
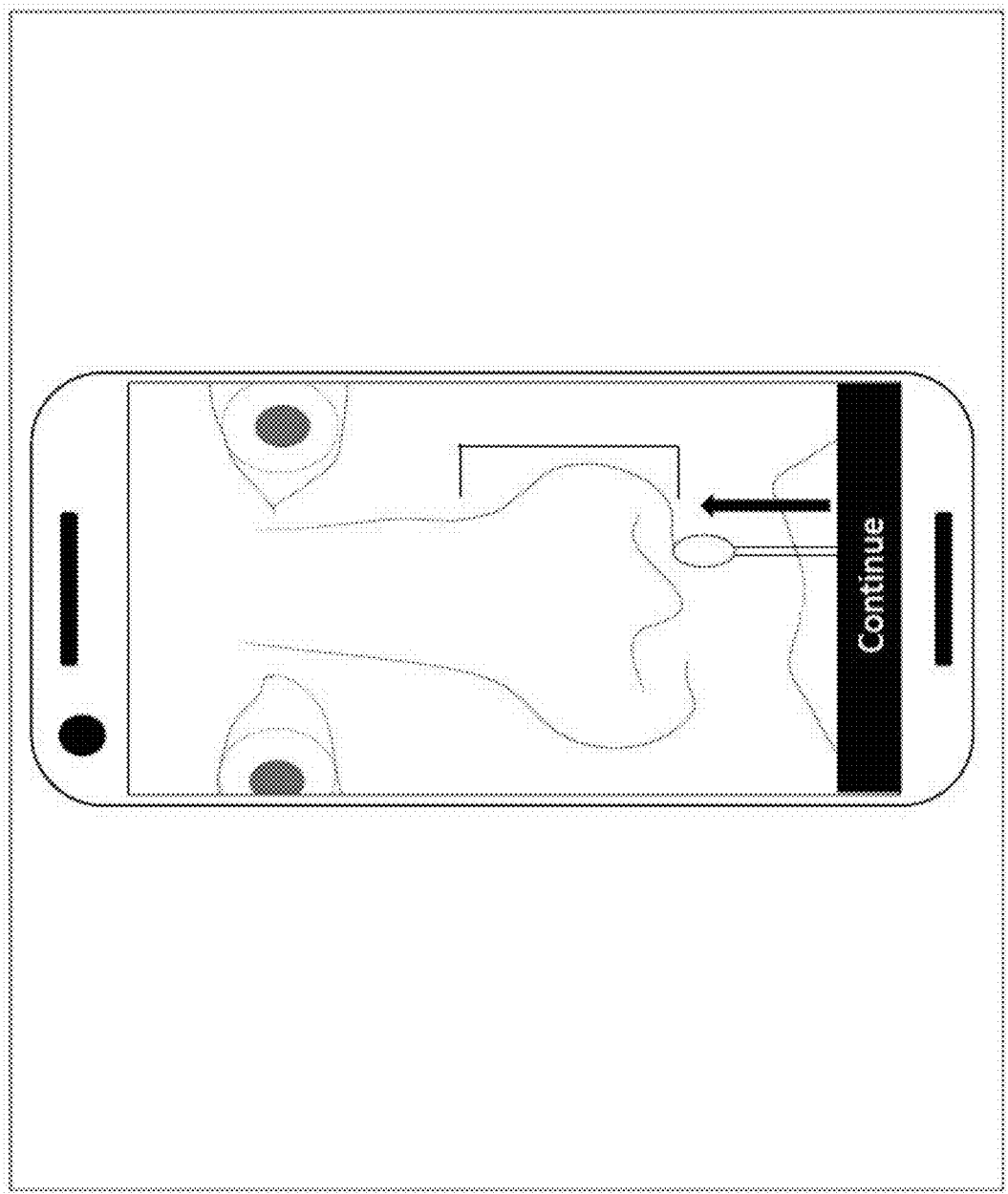
Figure 8F:
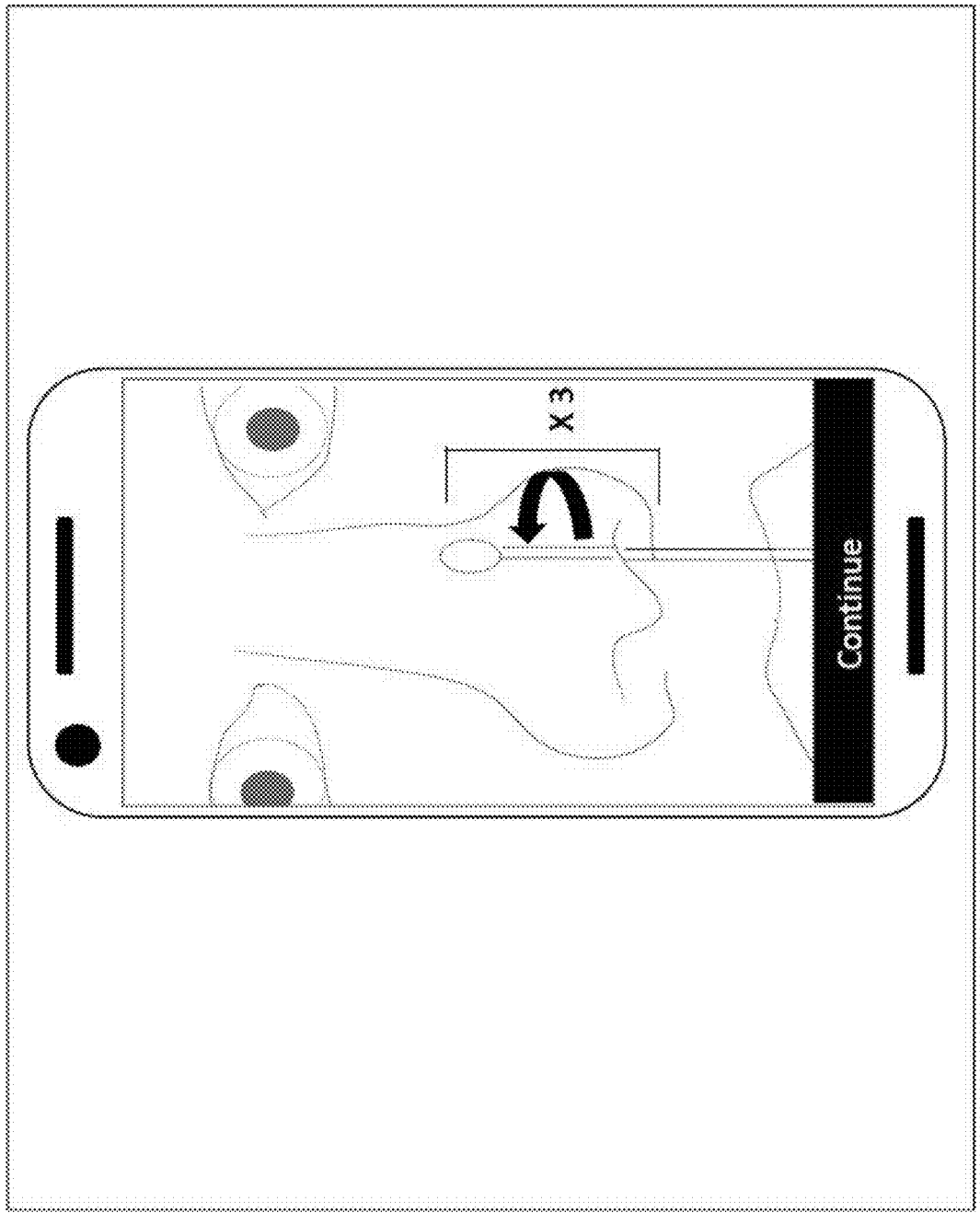

FIG. 8D includes a virtual image or animation of a bottle dropper (which may be one of the real-world items within the COVID-19 test kit) and a textual display of "X 6" indicating to the user to insert 6 drops of the fluid from the bottle dropper into the indicated hole or window on the COVID-19 test kit. FIG. 8E includes a virtual image or animation of a cotton swab stick (which may be another real-world item within the COVID-19 test kit) being inserted within a nostril, thus guiding the user to perform this step of the COVID-19 diagnostic test. FIG. 8F includes a virtual image or animation that includes a curved arrow and that may show the cotton swab stick rotating, as well as a textual display of "X 3", to indicate to the user to rotate the cotton swab three times within the nostril.

Figure 8G:
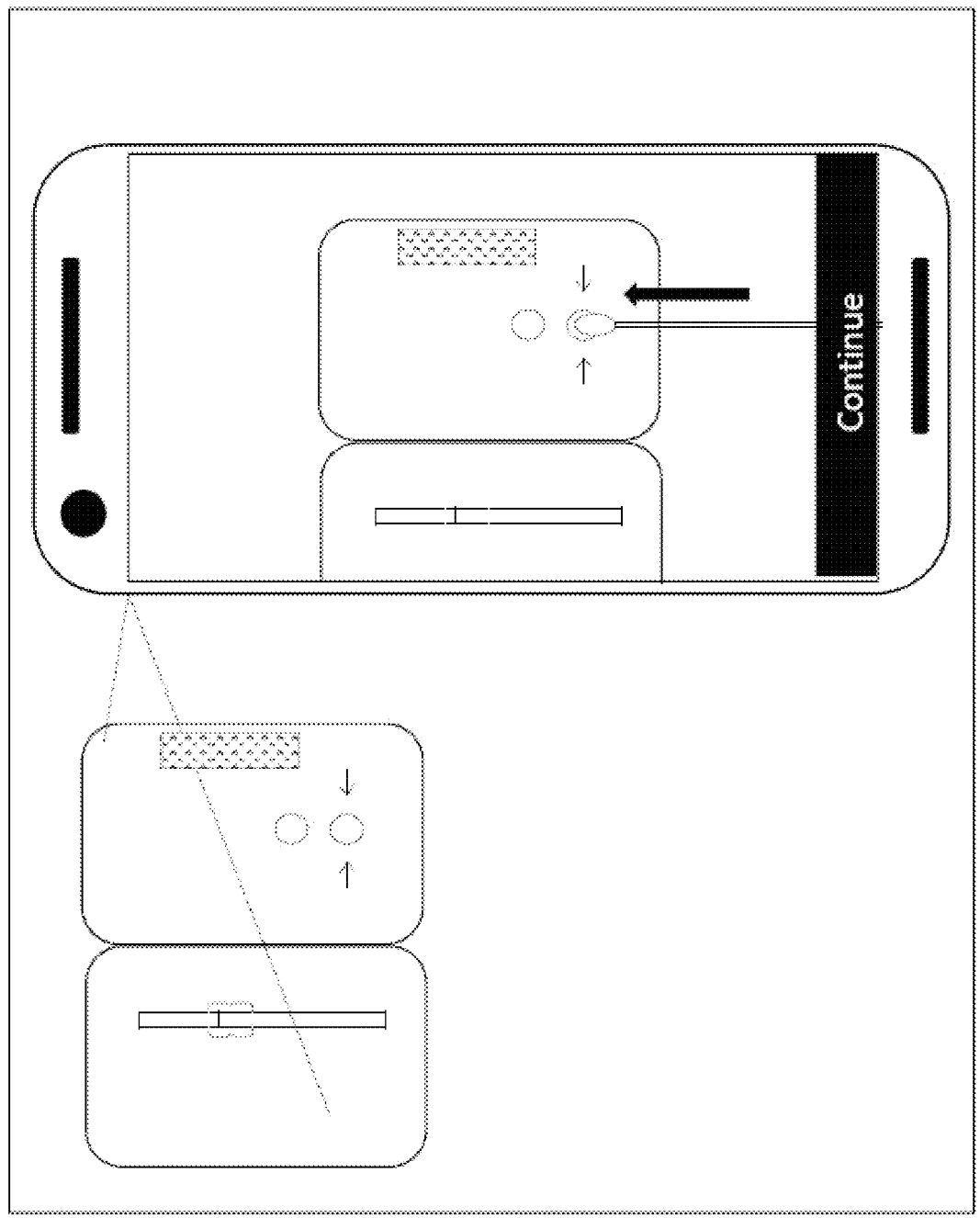
Figure 8H:
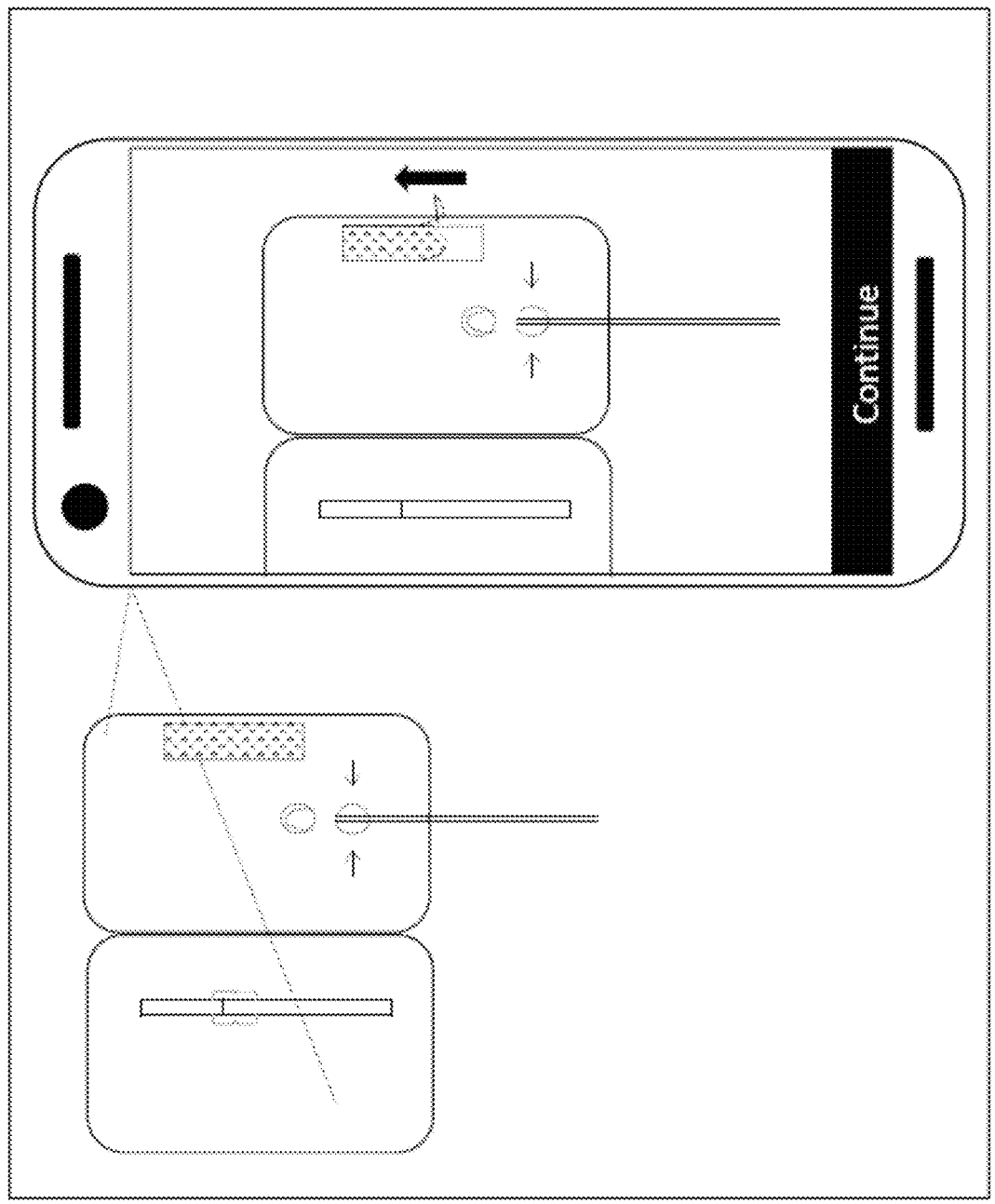
Figure 8I:
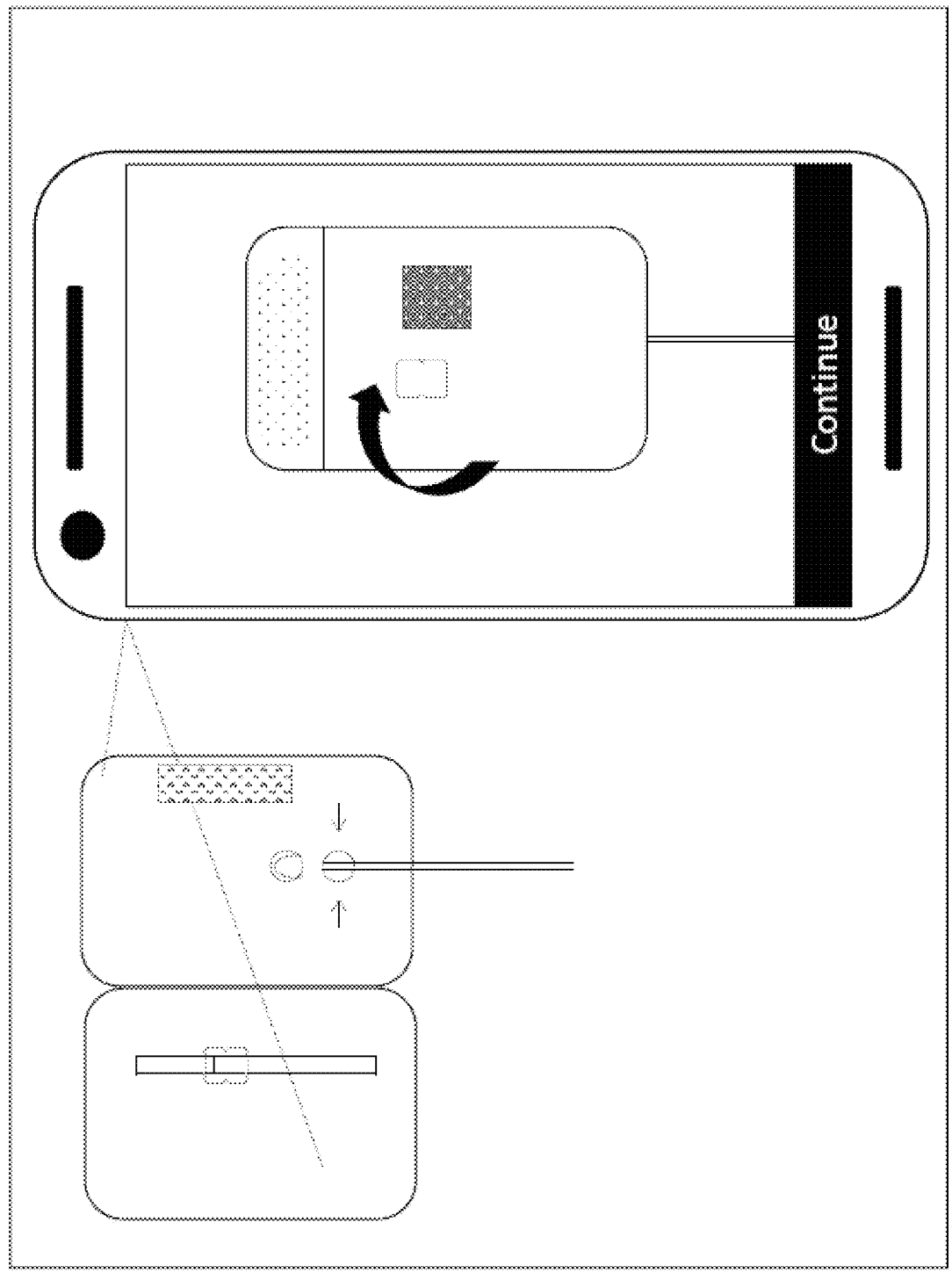
Figure 8J:
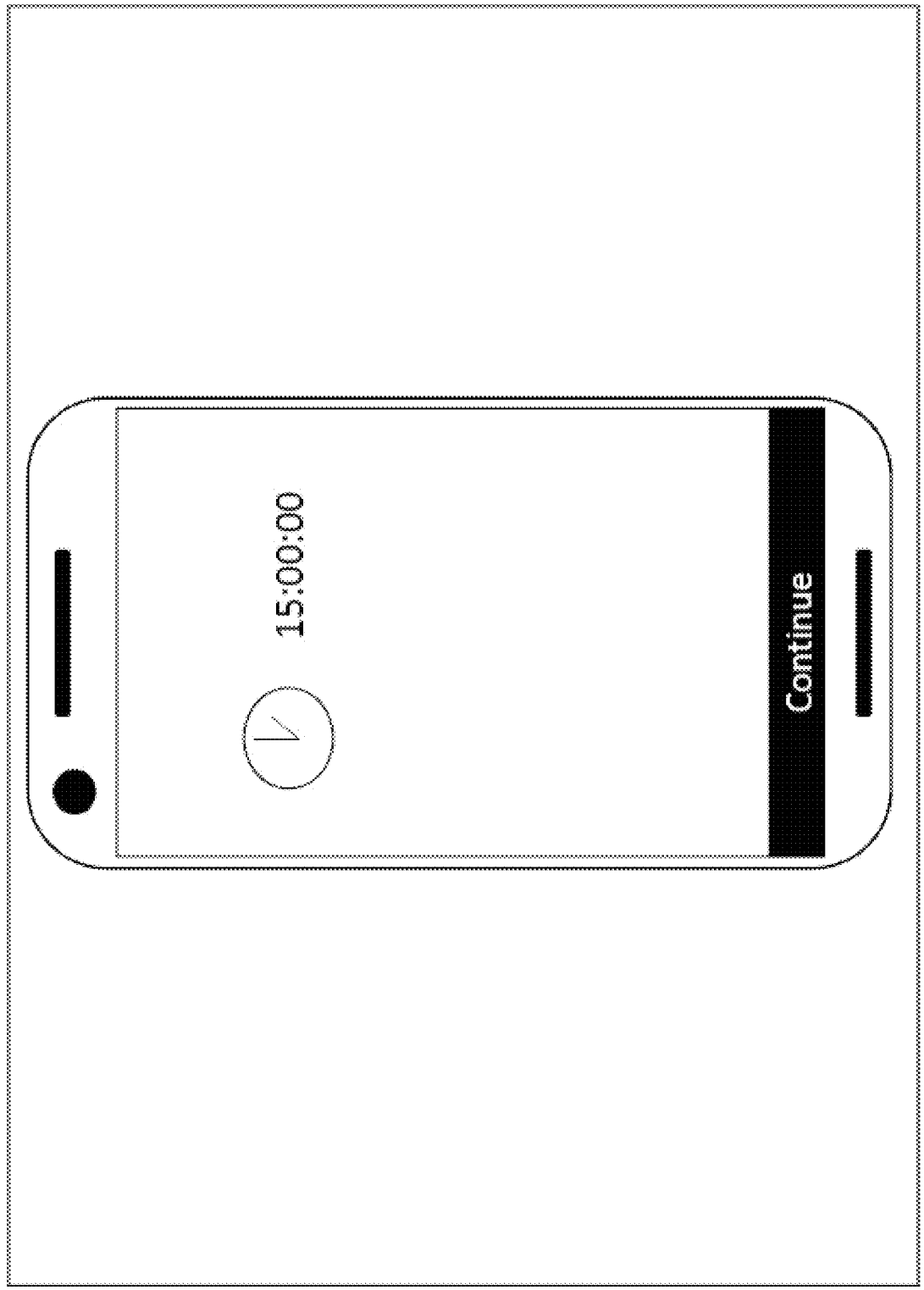

FIG. 8G includes a virtual image or animation of an arrow and a cotton swab stick guiding the user to insert the tip of the cotton swab stick that was inserted and rotated within the nostril into the indicated lower hole on the COVID-19 test kit. FIG. 8H includes a virtual image or animation of an upward-directed arrow and the cotton swab stick guiding the user to advance the cotton swab stick upward until the cotton tip of the cotton swab tip is visible within the upper window or hole of the COVID-19 test kit. The upward arrow may also indicate to the user that a covering of an adhesive strip on the exterior of the COVID-19 test kit should be removed. FIG. 8I again includes a curved arrow virtual image or animation to guide the user to fold the two portions of the COVID-19 test kit together to seal the portions together to facilitate testing of the sample. FIG. 8J shows a screen display including a timer to guide the user as to how long to wait until the results can be viewed for accuracy.

Figure 9B:
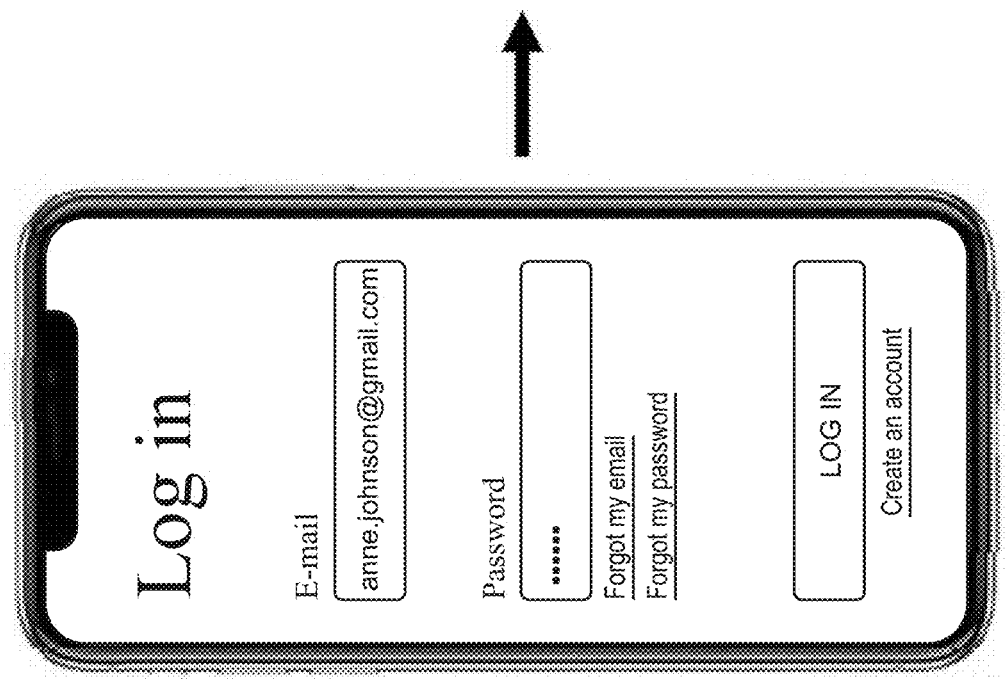
FIGS. 9A-9F illustrate a series of example screen displays that can be displayed to a user to guide the user through the steps of administering an at-home drug test according to some embodiments described herein.
Figure 9A:
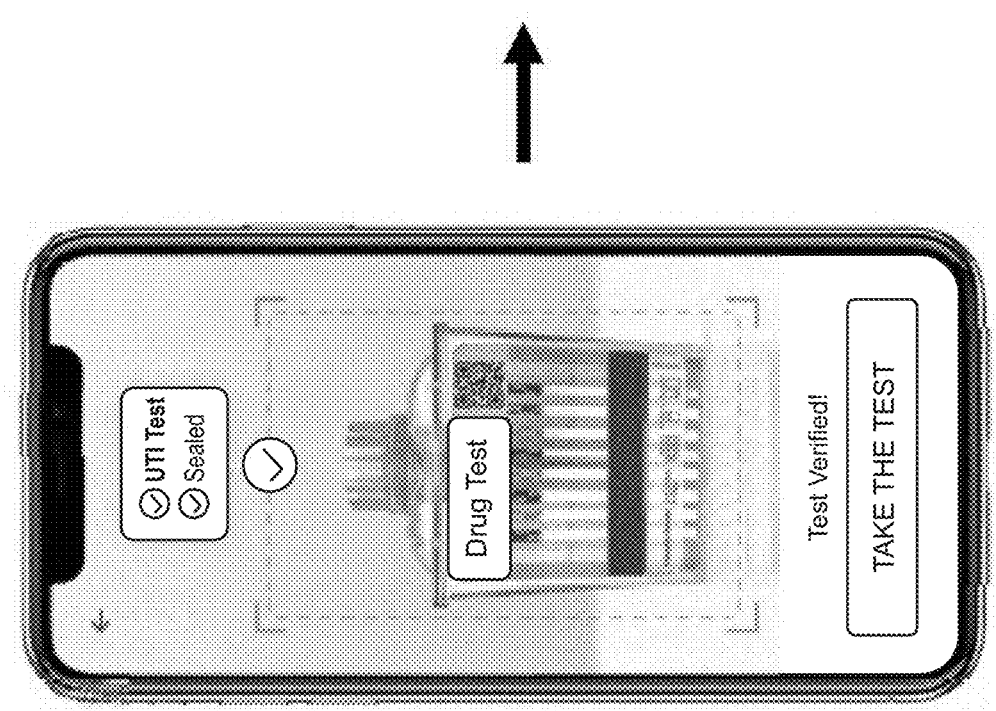

FIGS. 9A-9F illustrate a series of example screen displays that can be displayed to a user to guide the user through the steps of completing an at-home drug test according to some embodiments described herein. Again, the screen displays may include augmented reality display content that is overlaid on real-time, real-world camera images of components or portions of the medical diagnostic test kit 115 and/or the user. FIG. 9A shows a screen that may be displayed after scanning of the machine-readable code 120 on a drug test kit and provides a user-selectable option on the graphical user interface (e.g., a user-selectable button) to facilitate receipt of user input data to proceed with administration of the medical diagnostic test.

In some implementations, as shown in FIG. 9B, the user must log in to the health testing platform or Web application prior to proceeding with the diagnostic test (e.g., drug test) in order to authenticate the user and to facilitate tracking and processing of test results and/or generation of a virtual pass upon completion of the testing process. FIG. 9C shows a screen display in which textual instructions are provided to the user guiding the user as to what to do. A visual image is also displayed to visually show the user the step to complete. A box is overlaid on the image so that the user can fix his or her face within the box while performing the testing step of swabbing his or her mouth with a swab located in the drug test kit. The display further includes a countdown timer.

Figure 9D:
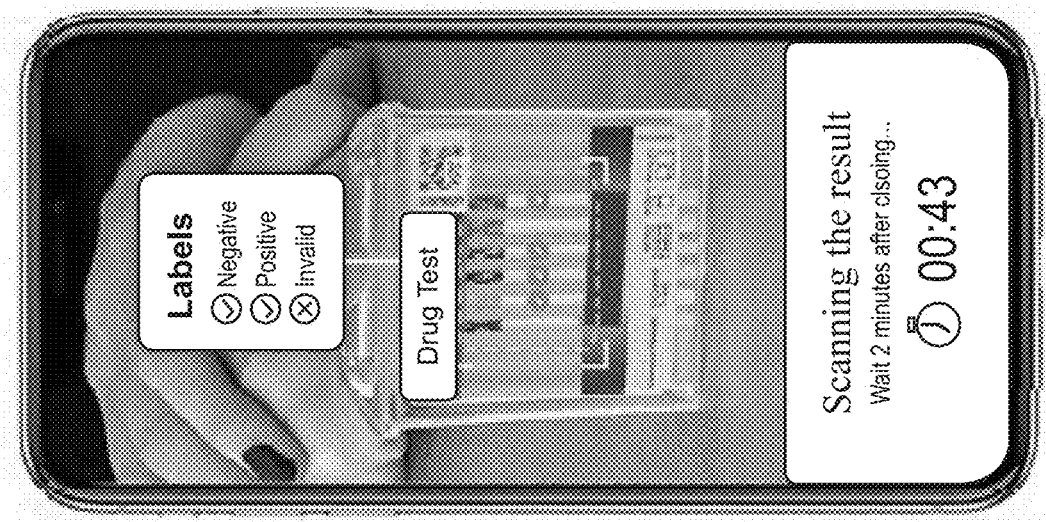
Figure 9C:
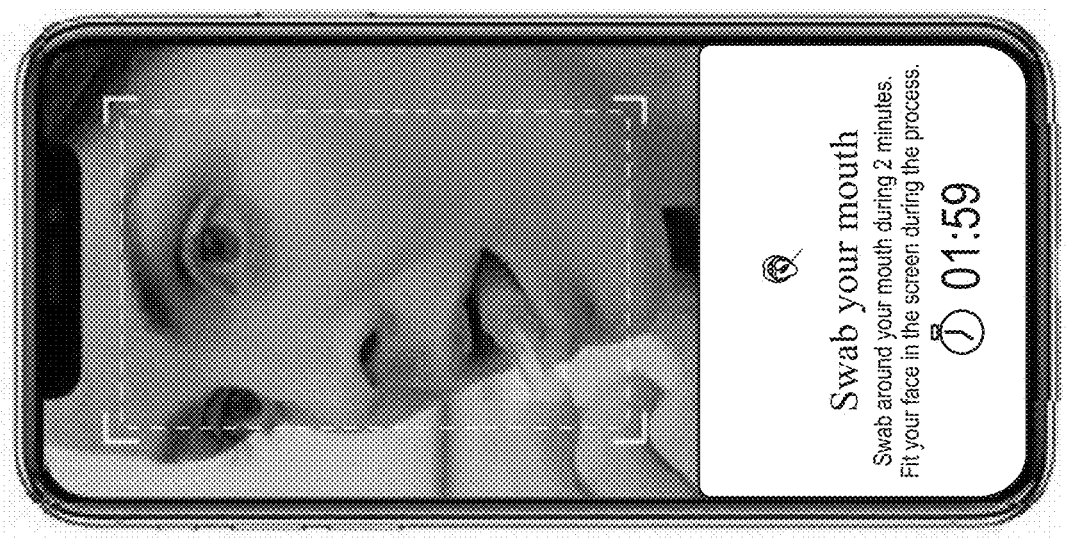
Figure 9F:
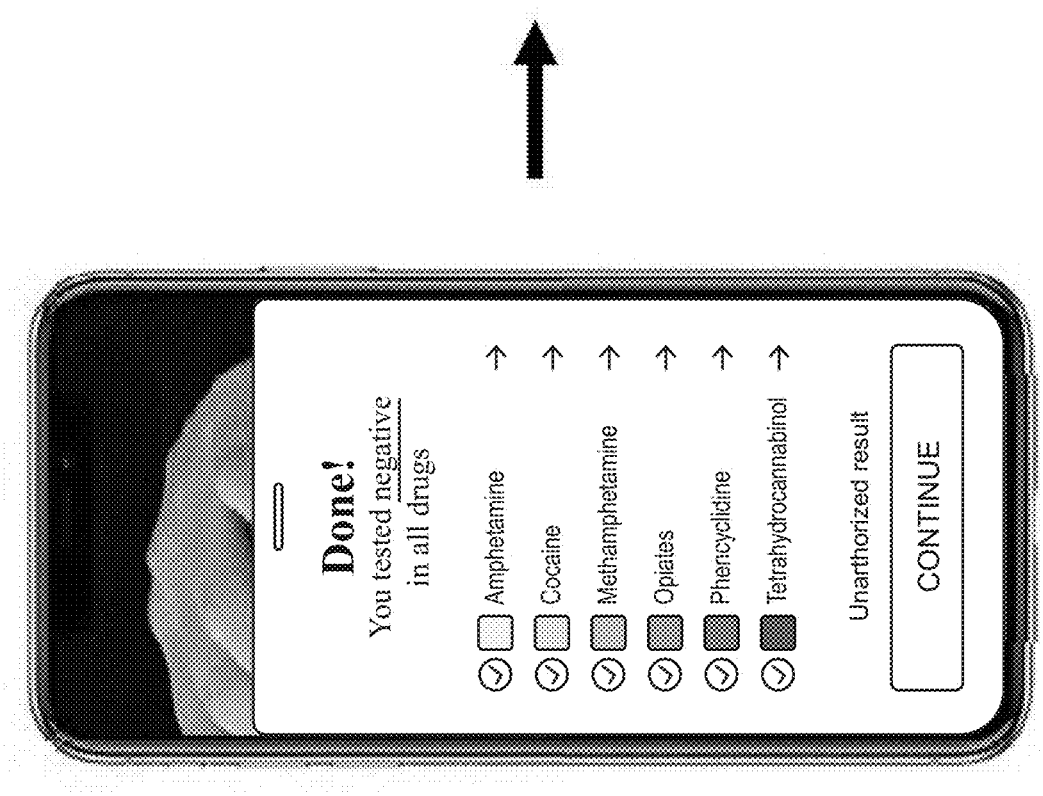
Figure 9E:
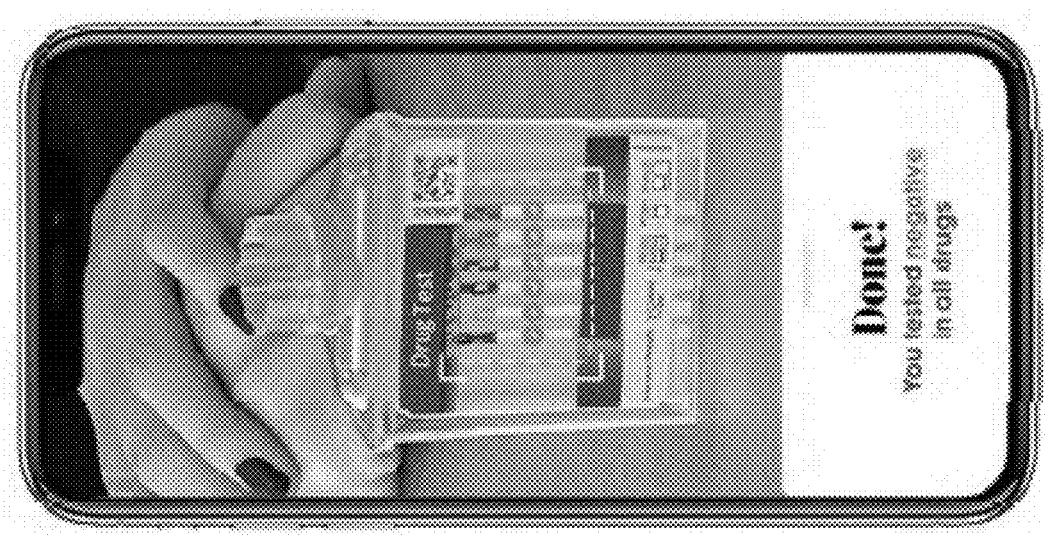

FIG. 9D includes instructions and a countdown timer guiding the user to wait to scan or take an image capture of the results until after a certain amount of time. The display may also include overlaid information as to how to interpret the test results. FIG. 9E indicates the test results to the user. The display may also include overlaid virtual content showing a box to guide the user as to what portion of the test kit to capture with a camera of the user device in order to capture the drug test results in the image. FIG. 9F displays more detailed test results and provides an option for the user to obtain more information regarding the test results. In some embodiments, the systems disclosed herein are configured to determine test results based at least in part on images captured of a medical diagnostic test, such as a UTI or drug test, and overlay subsequent images of the diagnostic test as displayed on a user device with graphics indicative of the determined test results. In some examples, these graphics may highlight or point out specific regions, markers, or features on testing materials that are indicative of results, along with graphics indicating what those results are determined to be. For instance, test results may be determined by way of computer vision techniques and/or human observation and interpretation of images of the medical diagnostic test. Such human observation and interpretation may be provided by a guide, medical professional, or other person with which the user is connected during the testing session. In some examples, such as those in which a drug test or COVID-19 test is administered, the user may be connected with one or more persons who serve to proctor one or more portions of the testing session. This may enable testing results to be verified and optionally reflected in a pass that is provided to the user after the test has concluded.

Figure 9G:
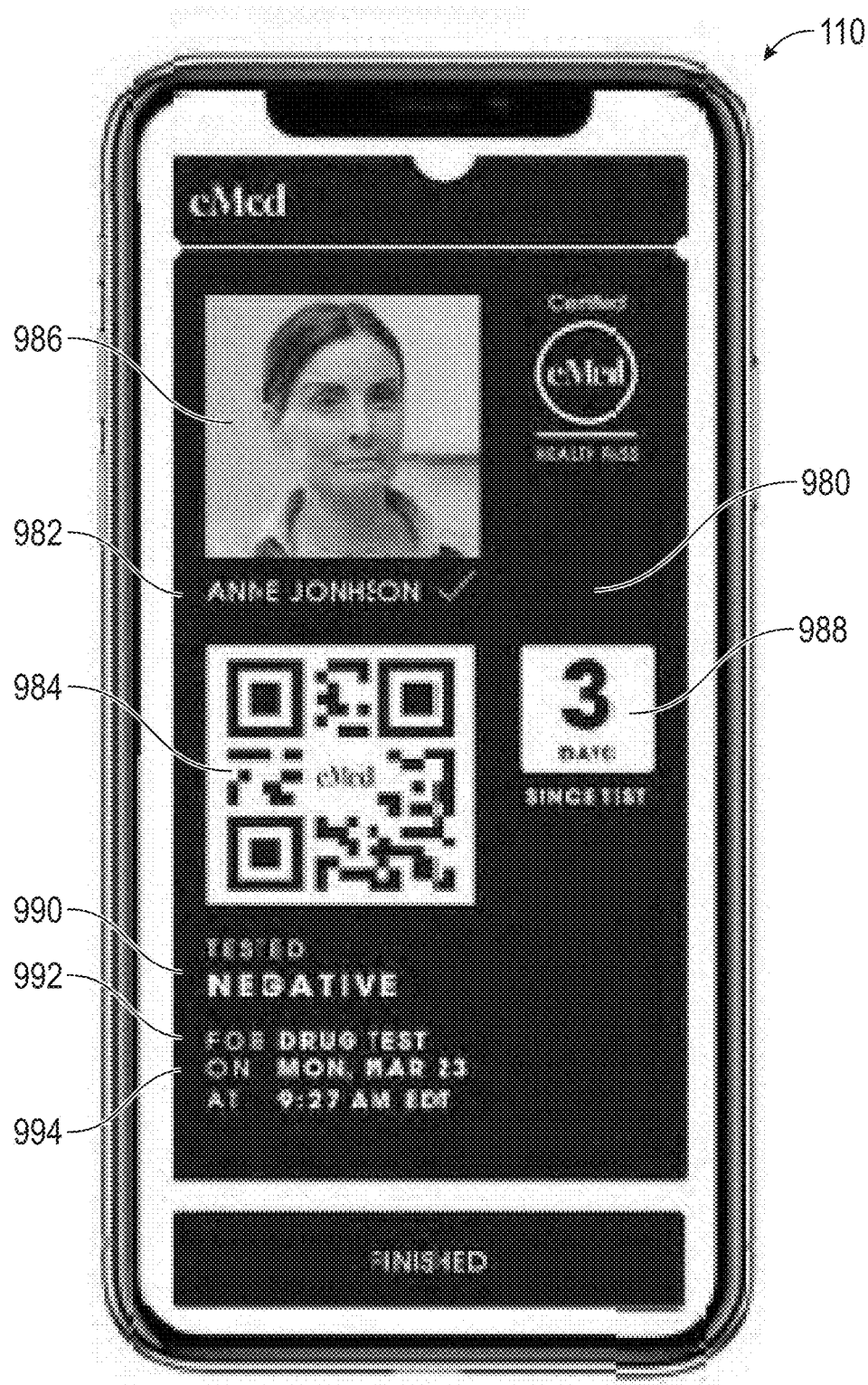
FIG. 9G illustrates an example of a virtual test pass that can be generated following completion of one of the at-home medical diagnostic tests contained within the medical diagnostic test kit container of FIG. 1 according to some embodiments described herein.

FIG. 9G illustrates an example of a certified virtual test pass 980 that can be generated by the provider health platform following completion of one of the at-home medical diagnostic tests contained within the medical diagnostic test kit container or package 100, such as the drug test or a COVID-19 test. The virtual test pass 980 may comprise a digital test completion pass that may be shown or displayed on a user device (e.g., mobile phone or tablet) or sent via email or text message to a recipient requiring proof of the test results.

The test pass 980 can be provided and associated with the remote health testing and diagnostic platform that is used to identify the user and communicate the user's test results. In some implementations, the test pass 980 can be provided at and/or used to verify a user's identity at a point of care, such as the location where the test is taken (e.g., a medical facility, a care facility, an assisted living center, a home, a hotel, an airport, a etc.), and also used to verify the user's test results at a point of verification (e.g., a location where the user's results are checked (such as the airport, a hotel, a place of employment, etc.). In some implementations, the point of care and the point of verification may be different. For example, a user may take the test at his or her home and receive the test pass 980 and then can use the test pass 980 to verify his or her results at the airport. In some implementations, the point of care and the point of verification may be the same. For example, a user desiring to board a flight at an airport can take a test and receive a test pass 980 at the airport and then use that pass to verify the results and board a flight.

In some implementations, the test pass 980 can be configured to perform one or more of several functions. For example, the test pass 980 can include proof of the user's identity. For example, in FIG. 9E, the test pass 980 includes personal information 982. The personal information 982 can include the user's name and other identifying information such as photo or other biometric information. The test pass 980 can be configured to show this information to prove the user's identity at a point of care (e.g., at medical facility or home at which the test is taken) and at point of verification (e.g., at an airport, stadium, etc., where the test result is checked). In some implementations, the test pass 980 includes a positive identifier that checks or verifies the user's identity against a driver's license, passport, or other verifiable biometric data. In various implementations, identity verification using the test pass 980 should be simple and quick. Additionally, the test pass 980 should be configured such that the results reported by the test pass 980 should be able to be trusted at point of verification. For example, the test pass 980 can ensure that results stored on the pass were gathered using an FDA-approved method. The test pass 980 can also be configured for information security. For example, the test pass 980 can provide the user with a mechanism for controlling who accesses their data and when.

A test pass 980 can be provided in either a physical or virtual manner. For example, a physical test pass may comprise forgery-resistant card provided by the test pass issuer that includes user's name and photo for identification. The physical test pass may also include a barcode, QR code, NFC chip, contact chip, alphanumeric code, or other unique identifier that will access test results from a secure database when scanned. A virtual test pass, or digital health pass, may be available over a computer network or through a Web application. When accessed, it can display a machine-readable code 984 (e.g., QR code) or use NFC or other means for quick communication at point of verification. The machine-readable code 984 may direct interested parties to a webpage containing additional information about the patient, the test, the test results, and/or other tests that the patient has undergone. In some implementations, the test pass 980 can be linked to a user's existing ID. For example, test results can be linked to an existing form of ID by name and unique number (driver's license number, passport number, etc.). In some configurations, the user must have this ID at point of care and point of verification, where their name and unique number are used to access results from a secure database. The test pass 980 may also include a photo 986 of the user, an indication of the number of days since the test 988, a general result of the test 990, a test type 992, and further details regarding date and time of the test result 994. In addition, the test pass 980 may comprise an expiration, which may comprise easily accessible information regarding expiration of the dependability of the test result based on health guidelines provided by government entities or otherwise.

In some implementations, each user is provided with a new virtual test pass 980 each time they complete a test. For example, a user may be provided with a new virtual test pass indicating the most recent test result. In other implementations, in which the user already has a test pass, upon completion of a new test, the existing test pass can be updated to include the most recent result. For example, the machine-readable code 984 on the virtual test pass 980 may be linked to the newest test result.

In some implementations of the virtual test pass 980, the user's ID may be verified each time that the virtual test pass is displayed. For example, the user may be required to be biometrically authenticated each time the virtual test pass 980 is to be displayed. As one example, the user may use face recognition on his or her phone in order to verify his or her identity before the virtual test pass 980 can be displayed.

FIGS. 10A-10H illustrate a series of example screen displays that can be displayed to a user to guide the user through the steps of completing an at-home UTI test according to some embodiments described herein. The screen displays may include augmented reality display content that is overlaid on real-time, real-world camera images of components or portions of the medical diagnostic test kit 115 and/or the user. As shown, the screen displays may also include infographics, text instructions, and user-selectable content (e.g., buttons) to facilitate receipt of user indication of completion of each step of the testing process in order to continue on to the next step.

Figure 10B:
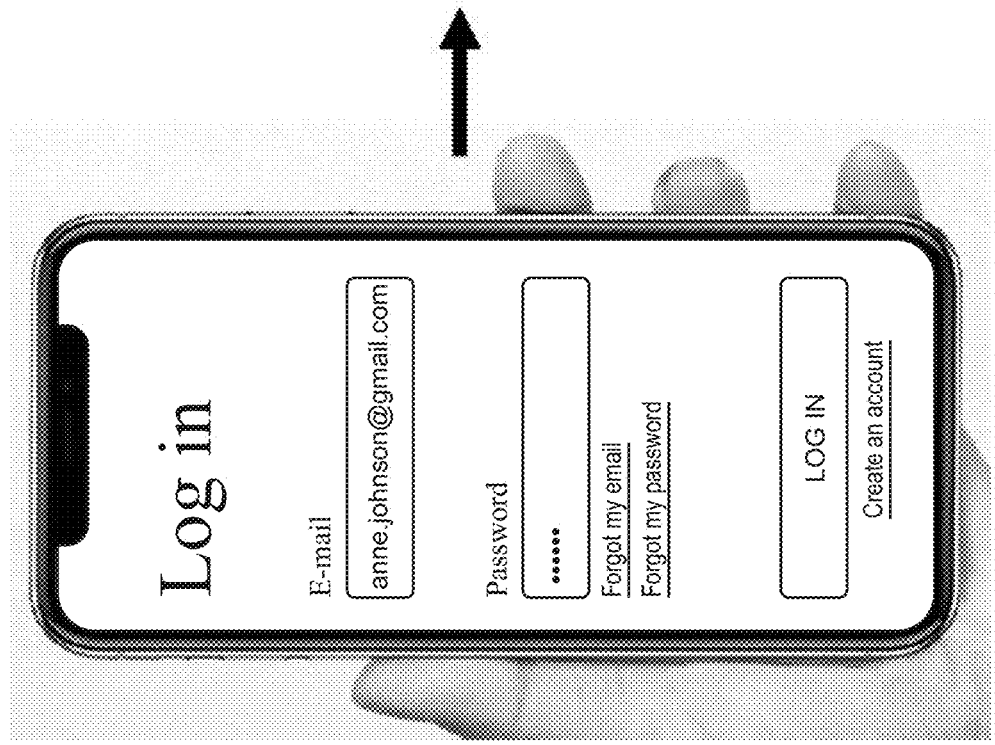
Figure 10A:
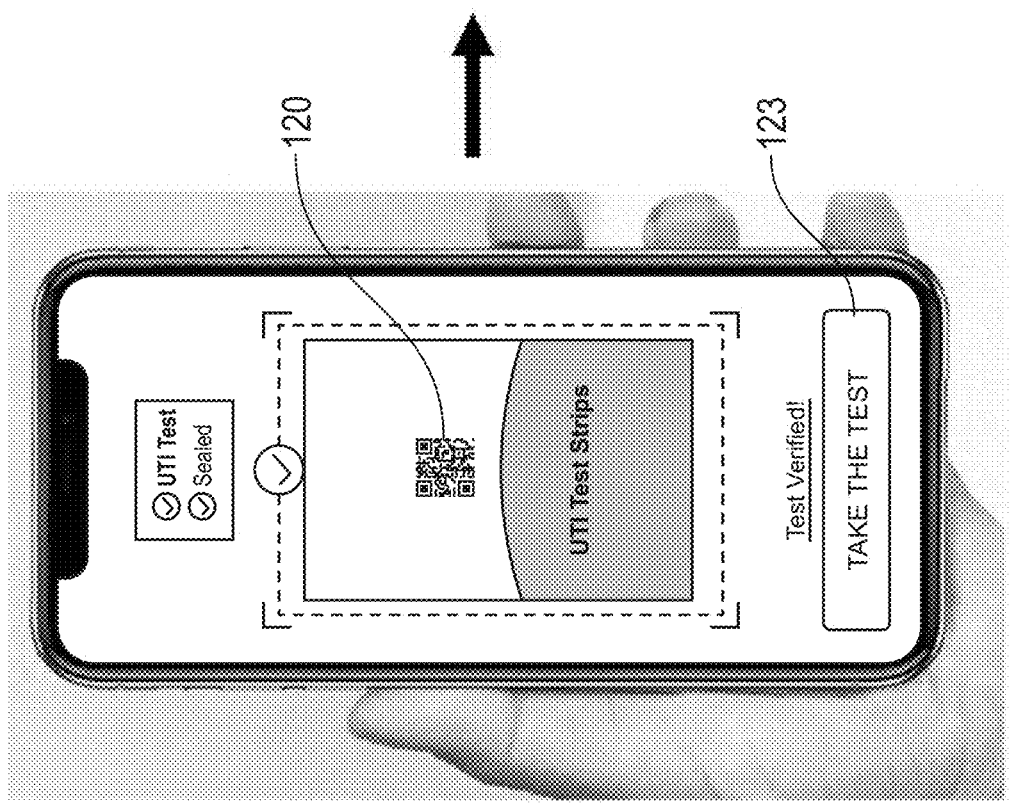

FIG. 10A shows a screen that may be displayed after scanning of the machine-readable code 120 on a UTI test kit and provides a user-selectable option on the graphical user interface (e.g., a user-selectable button 123) to facilitate receipt of user input data to proceed with administration of the medical diagnostic test. The display may also indicate verification of the particular medical diagnostic test. In some implementations, as shown in FIG. 10B, the user must log in to the health testing platform or Web application prior to proceeding with the diagnostic test (e.g., UTI test) in order to authenticate the user and to facilitate tracking and processing of test results and potentially later ordering of prescription medication, such as an antibiotic to treat the UTI.

FIG. 10C includes a display that instructs the user to take the contents out of the UTI test kit. The display may also instruct the user to take an image capture of the contents of the UTI test kit prior to testing. FIG. 10D includes a display that instructs the user to complete certain steps in the UTI testing process. The graphical user interface may include checkboxes that a user must check in order to continue with the testing process. Because certain tests may involve interaction with private body parts of the user, the camera and overlaid augmented reality content may not be used during certain parts of the testing process for privacy reasons.

Figure 10F:
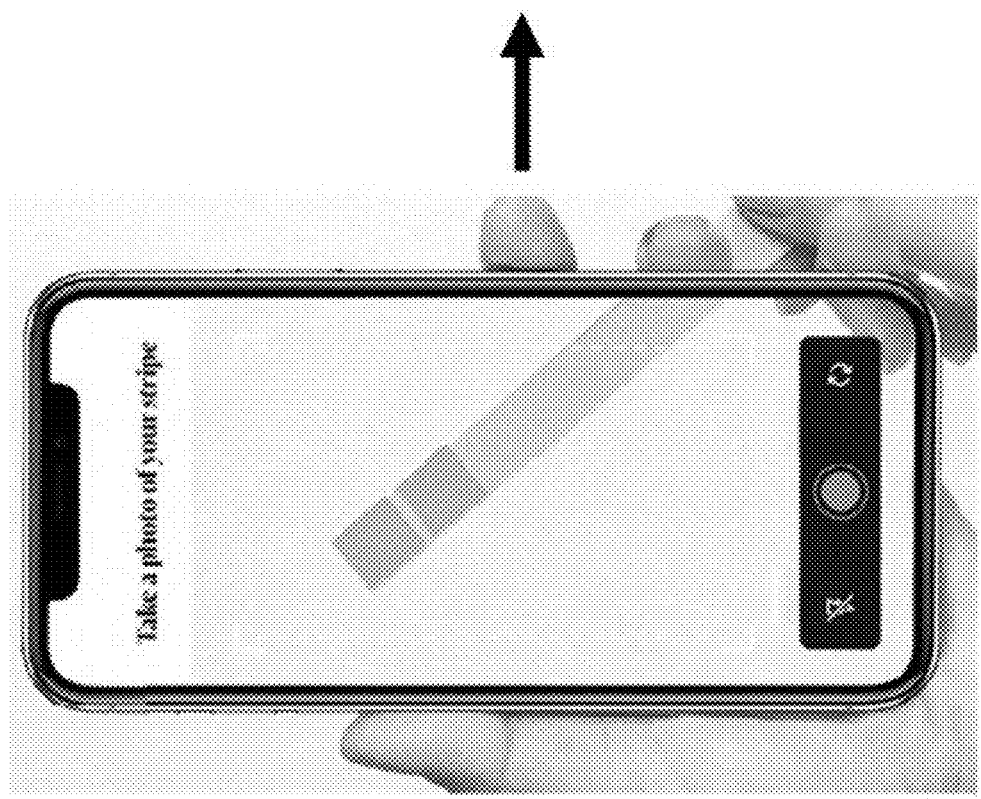
Figure 10E:
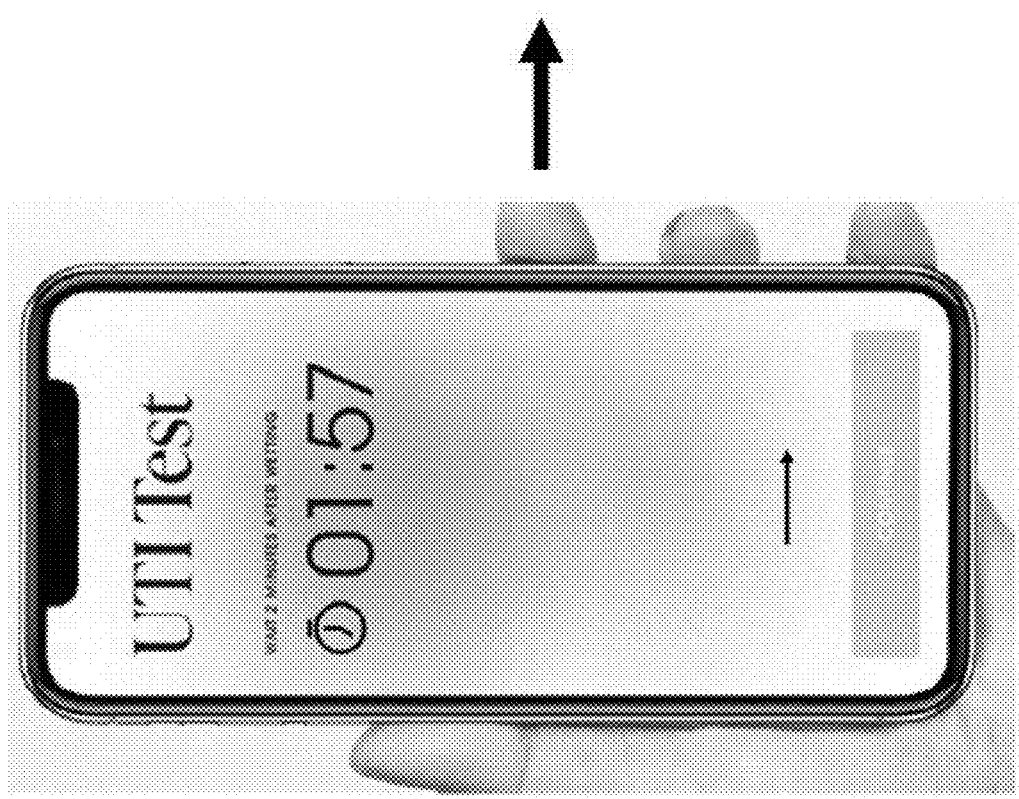

FIG. 10E shows an example screen display including a timer to guide the user as to how long to wait until the results can be viewed for accuracy. FIG. 10F instructs the user to take a photo of a portion of the test strip indicative of the result and facilitates the image capture process. FIG. 10G show example displays indicating the test results to the user along with additional details for more information.

In several implementations of completion of the medical diagnostic tests, such as those described above, the user device 110 may be positioned such that the user is visible within the field of view (FOV) of the user device's forward-facing camera and the medical diagnostic test kit 115 is positioned within the FOV of the user device's rearward facing camera. Such a set up may be advantageous as it allows the user and the medical diagnostic test kit 115 to remain within the different FOVs of the forward and rearward facing cameras of the user device 110 during the entire testing procedure. Further, at different portions of the procedure, the output of the frontward or rearward facing camera can be displayed to the user and supplemented with AR-based guidance.

For example, during one portion of the testing procedure, the output of the rearward facing camera (e.g., FOV in which is positioned the test kit 115) can be displayed to the user such that the user can view the test kit 115 on the display of the user device 110. The display can be updated with AR-based guidance to highlight certain areas of the test kit 115 or items in the test kit 115 or overlaid with other types of instructions to aid the user in performing the testing procedure. During another portion of the testing procedure, the output of the frontward facing camera (e.g., FOV in which the user is positioned) can be displayed to the user such that the user can view his or herself on the display of the user device 110. The display can be updated with AR-based guidance to highlight certain areas of the user (e.g., a nostril) or overlaid with other types of instructions to aid the user in performing the testing procedure.

Although the figures have illustrated examples of AR-based guidance in cases where the user device comprises a smartphone, AR-based guidance can also be provided for other types of user device. For example, in the case of a laptop, the aforementioned camera might be a camera on the laptop located above the screen. In the case of a smartphone, the aforementioned camera might be an inward-facing camera on the front of the smartphone above the screen. Accordingly, in some smartphone embodiments (or other embodiments where the user device includes both forward- and rearward-facing cameras) some steps may be performed using the forward-facing camera and some steps can be performed using the rearward-facing camera. The display shown to the user (e.g., on the screen on the front of the device) can change from the forward- to the rearward-facing camera depending on the step being performed. In some embodiments, the change of cameras occurs automatically.

In some examples, the user may place the smartphone in a smartphone stand, and may be instructed to position the test kit in front of the smartphone such that both the user and the test kit are visible in the inward-facing camera on the front of the smartphone above the screen. With continued reference to examples where the user accesses the platform using a smartphone, the user may be instructed to seat themselves at a table (with a flat surface), place the test kit on the table about 1.5 to 2 feet from the edge of the table, place their smartphone in a smartphone stand (e.g., that is included in the medical diagnostic test kit container 100), and position the smartphone in the smartphone stand on the table between themselves and the test kit such that their face and upper body is within the field of view of the smartphone's inward-facing camera and the test kit is within the field of the smartphone's outward-facing camera. Depending on whether the user is being given test kit guidance or sample collection guidance, the live video feed that's displayed for the user and overlaid with graphics may switch between the outward- and inward-facing cameras.

Test Integrity and Verification

In some embodiments, during a remote testing procedure, various steps can be implemented before, during, and after the test in order to ensure test integrity and verify the result of the test. For example, before the test is taken, it can be desirable to verify the user's identify and to verify that the test kit is valid (e.g., to verify that the test kit is one that has been purchased or otherwise obtained through an official channel, has not expired, and has not been previously used). During the test, it can be desirable to verify that any sample obtained is actually obtained from the previously verified user and that all test instructions and procedures are followed correctly. Finally, after the test, it can be desirable to ensure that the test result is obtained from the previously verified test kit and to ensure that the test result is interpreted correctly.

As noted above, it can be important to verify the user's identity before the test is taken. This can be because it ensures that the results will be attributed to the correct person. Verifying the user's identity is particularly important in cases of remote testing as the person being tested is not physically located with the person administering the test. Thus, in many situations, extra precaution may be advantageously taken to correctly identify the user's identity. Verification of the user's identity can be accomplished in several ways. For example, the user can be asked to upload a copy of an official identification (e.g., a driver's license or passport) as part of an account creation or pre-qualification step. In some embodiments, the user may be asked to show the official identification to the proctor during the testing session. During the testing session, the proctor can then compare the uploaded or shown identification to the person's appearance in the video feed. In this way the proctor can verify the user's identity by comparing a live (or other) video feed of the user to an identification card associated with the user. In some embodiments, once the user's identity is verified, the user's identity can be associated with the user's account for future tests. For example, after verification, future verifications may be automated with face matching technology.

In another example, user identification can be achieved using biometrics. For example, in some embodiments, a user accessing the platform may be given the option to perform a biometric initialization, in which the user goes to a physical location where their fingerprint or a unique segment of DNA can be sampled and stored. Thereafter, every test taken can sample their fingerprint or DNA to verify identity. This may also be automated. In other embodiments, biometrics may be performed using biometric features of the user's device. For example, many smartphones today are capable of taking a user's fingerprint or recognizing a user's face. These features may be used to verify the user's identity in some embodiments.

In addition to verifying the user's identity, the test or test kit that will be used during the test may be verified as well. This can be important because it ensures that the test results are scientifically valid and can be trusted. Again, this can be particularly important in the case of remote testing where the user is not physically located with the person administering the test. In one embodiment, the test or test kit can be provided with a unique ID (e.g., a UID or serial number) assigned during manufacture, which can be queried when the test is taken. This can take the form of a printed string of characters, barcode/QR code, NFC/RFID tag, or other. This code may either explicitly encode information associated with the test (such as a test identifier, test expiration date, batch/lot codes, indication of whether this number has been used for a test or not) or it may encode a link to a database entry that includes such information. Prior to beginning the test, the code may be scanned to verify the test kit. If anything is amiss, the test does not proceed and the user may be instructed to obtain a new test kit. In some embodiments, it may be preferable to provide the unique ID in a non-human readable manner. This may provide an advantage in that they are harder to misrepresent. A visible code could be duplicated and used on an expired test, for example.

During a test, a sample may be collected from the user, for example, using the test kit. To ensure the integrity of the test, steps may be taken to ensure that the sample is actually collected from the same user whose identity was verified before beginning the test. Again, this can be especially important in the case of remote tests since the user is not physically located with the person administering the test. It can be important to ensure that a user does not swap in a sample obtained from another user when performing the test. Various mechanisms for verifying that the sample is collected from the previously verified user are possible. For example, during a proctored testing session, the proctor (or an automated system) can observe the sample collection process. For example, in the case of a nasal swab test, the proctor or the automated system can observe the user performing the swab procedure. Such observation can be performed live (e.g., over a live video connection) or through a pre-recorded video. In either event, it may be important that all sample collection materials remain in view of the camera at all times. This would prevent a user from swabbing his or her nose and then switching out the swab with another that has been used by a different person. Additionally, it may be beneficial to positively identify the user during the collection process. This can be accomplished by, for example, checking the user's identity immediately before the sample collection process.

During the test, it is also important to ensure that all test instructions and procedures are followed correctly. This can ensure the accuracy and validity of the test results. Similar to verifying that the sample is obtained from the correct user, ensuring that all test instructions and procedures are followed correctly can be accomplished by directly viewing the testing procedure, either over a live video feed or be watching a recording of the testing process. In some embodiments, such observation is provided by a live proctor. In some embodiments, such observation is provided through an automated system (e.g., a computer system that is configured to analyze live or pre-recorded video). In the case of a swab, for example, the swab can include stripes or other markings along its length to be able to quantify swab insertion depth in an orifice, such as a nostril. In this manner, a proctor can easily observe that the swab is inserted to a sufficient depth. Additionally, the automated system can be configured to recognize the stripes or markings on the swabs in the video to automate determination of proper insertion depth. In some embodiment, in which test a test must sit for a certain amount of time (e.g., dwell example), the user can be instructed to place the test on a suitable surface in view of the camera for an appropriate amount of time. The proctor or system can observe that the test is placed on the appropriate surface and remains in view during the entire dwell length. In the case of a nasal swab COVID-19 test, for example, an appropriate amount of liquid may need to be added to a testing card, a nasal swab may need to be inserted into the nostril to a sufficient depth, the swab must then be correctly applied to the liquid on the card, and the card must be left undisturbed on a flat surface for at least fifteen minutes. Each of these steps can be observed and verified by a proctor and/or an automated system to ensure the integrity of the test.

Additionally, it is important to ensure that submitted test results actually come from the originally verified test or test kit. This can ensure test continuity, making sure that the same test is used throughout the test (e.g., that the test that was verified is the one for which results are obtained). Otherwise, tests could be exchanged during the process, leading to improper results. In some embodiments, this can be accomplished by reverifying the test or test kit throughout the testing procedure. For example, the method that was used previously to determine the test kit was valid (e.g., scanning the unique ID of the test kit) can be repeated to ensure the UID/serial number are the same. In some embodiments, the test kits can be designed such that the test such that the results are reported in a manner that includes the UID/serial number, such as in a custom visible code (barcode, QR code, etc.) or NFC/RFID, so that when the results are read, the UID can be verified. For example, in some embodiments, test results are verified by viewing strips that appear on a test card. The test card can include the unique ID of the test kit near the area at which the strips will appear such that a view of the strips also includes a view of the unique ID.

Finally, it can also be important to ensure that the test results are interpreted correctly. As described previously, in some embodiments, a proctor interprets the test results by viewing strips that appear on a test card, for example. In some embodiments, an automated system may interpret the test results. In some embodiments, the test results can be reviewed and verified by another proctor or automated system to provide a second layer of verification.

At-Home Medical Diagnostic Test Kit Container Labels and Inserts

Figure 11:
FIG. 11 illustrates an example of a graphic label (including a machine-readable code) that can be printed on or adhered to an external surface of a medical diagnostic test kit within the medical diagnostic test kit container or package of FIG. 1 according to some embodiments described herein.

FIG. 11 illustrates an example of a graphic label 1100 (including a machine-readable code 120) that can be printed on or adhered to an external surface of a medical diagnostic test kit 115 within the medical diagnostic test kit container or package 100. In various implementations, the external surface may be a top external surface, a bottom external surface, or an inner surface (e.g., underside of lid). As can be appreciated, the graphics can be arranged or altered as desired and/or required. The graphic label 1100, or variations thereof, may also be positioned on multiple external and/or internal surfaces of the medical diagnostic test kit container 100.

Figure 12:
FIG. 12 is an example of a graphic label (including a machine-readable code) that can be printed on or adhered to an external surface of the medical diagnostic test kit container or package of FIG. 1 according to some embodiments described herein.

FIG. 12 is an example of a graphic label 1200 (including a machine-readable code 105) that can be printed on or adhered to an external surface of the medical diagnostic test kit container or package 100. In various implementations, the external surface may be a top external surface, a bottom external surface, or an inner surface (e.g., underside of lid). As can be appreciated, the graphics can be arranged or altered as desired and/or required. The graphic label 1200, or variations thereof, may also be positioned on multiple external and/or internal surfaces of the medical diagnostic test kit container 100. As shown, the graphics of the graphic label 1200 include an indication of the types and quantity of each type of medical diagnostic test kits located within the medical diagnostic test kit container 100. As can be appreciated, the graphics can be arranged or altered as desired and/or required.

FIGS. 13 and 14 are examples of graphic labels or inserts that may be provided on or inside the medical diagnostic test kit container or package 100 according to some embodiments described herein. The labels or inserts or graphics of FIGS. 11-14 may indicate the types of tests included, general instructions regarding an overview of the remote at-home testing process, and additional details regarding how the test results can be validated and certified so that the test results can be used to facilitate travel or to comply with testing requirements.

The labels or inserts or graphics of FIGS. 11-14 may also include (i) a QR code or other machine-readable code or computer-readable graphic that, when scanned by a user device, directs the user device to one or more resources (e.g., web pages, application screens, etc.) that are associated with the medical diagnostic kit container 100 and/or one or more of the medical diagnostic test kits 115 associated therewith, (ii) steps or directions for taking any of the medical diagnostic tests associated with the container 100 and/or starting a proctoring session for verifying the results of any of the medical diagnostic tests, (iii) information on how to obtain treatment for conditions associated with any of the medical diagnostic tests, (iv) information on the contents of the box, (v) information on the health pass that can be obtained upon testing negative on any of the medical diagnostic tests, or a combination thereof. As can be appreciated, the graphics can be arranged or altered as desired and/or required.

Prescription Medicine Order Fulfillment and Delivery Coordination

Figure 15:
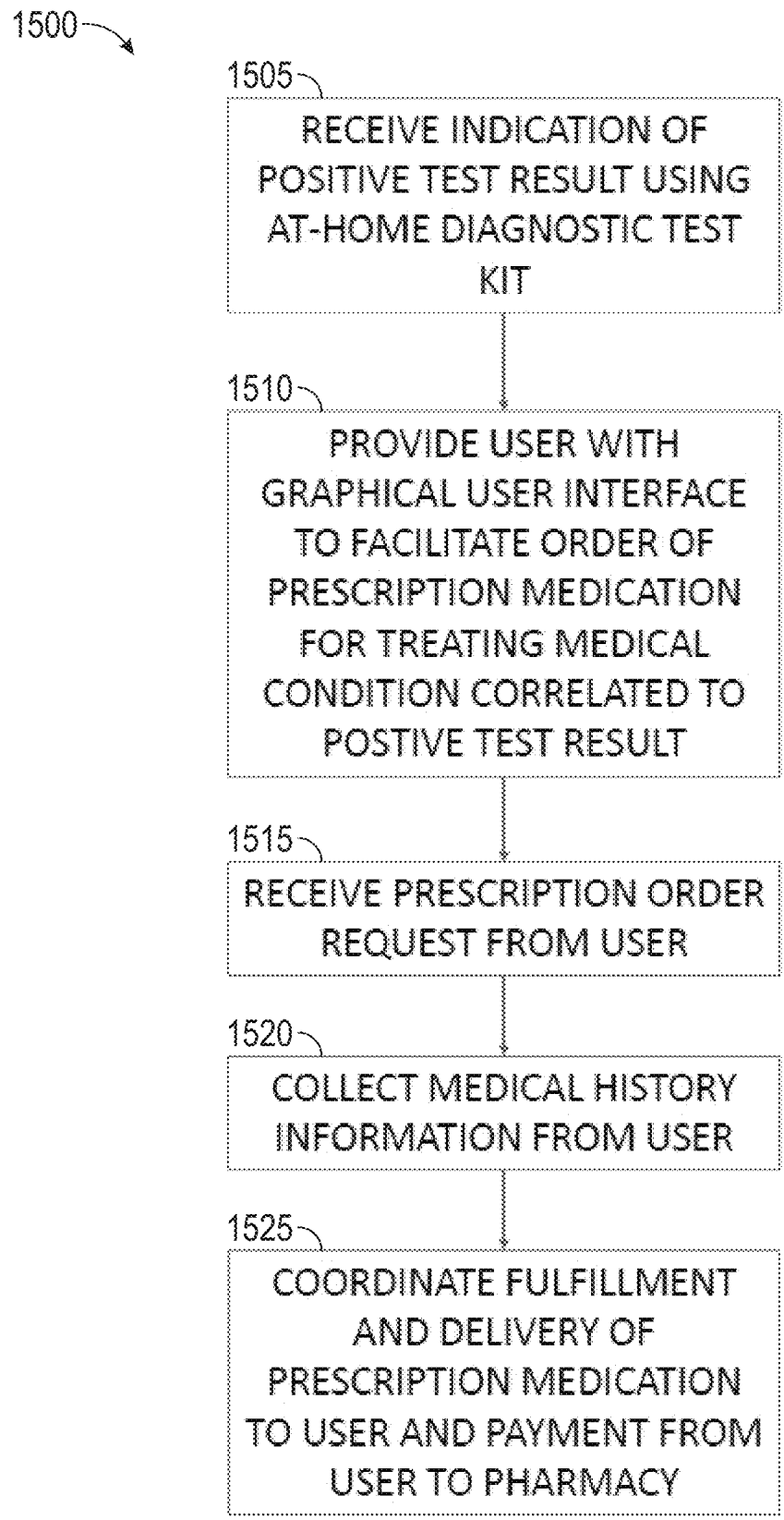
FIG. 15 illustrates an example flowchart of a method for facilitating ordering, fulfillment, and or delivery of prescription medication following a test result indicative of a medical condition that can be treated with prescription medication according to some embodiments described herein.

FIG. 15 illustrates an example flowchart of a method 1500 for facilitating ordering, fulfillment, and or delivery of prescription medication following a test result indicative of a medical condition that can be treated with prescription medication according to some embodiments described herein. At Block 1505, the remote health testing and diagnostic platform (e.g., platform 1902 shown in FIG. 19) receives an indication of a test result using an at-home diagnostic test kit (e.g., medical diagnostic test kits 115 in medical diagnostic test kit container 100) that the user has a particular medical condition (e.g., UTI, STI, influenza, COVID-19). In some embodiments, the indication of the test result may correspond to a test result as interpreted and submitted by the user and/or a proctor.

Figure 17A:
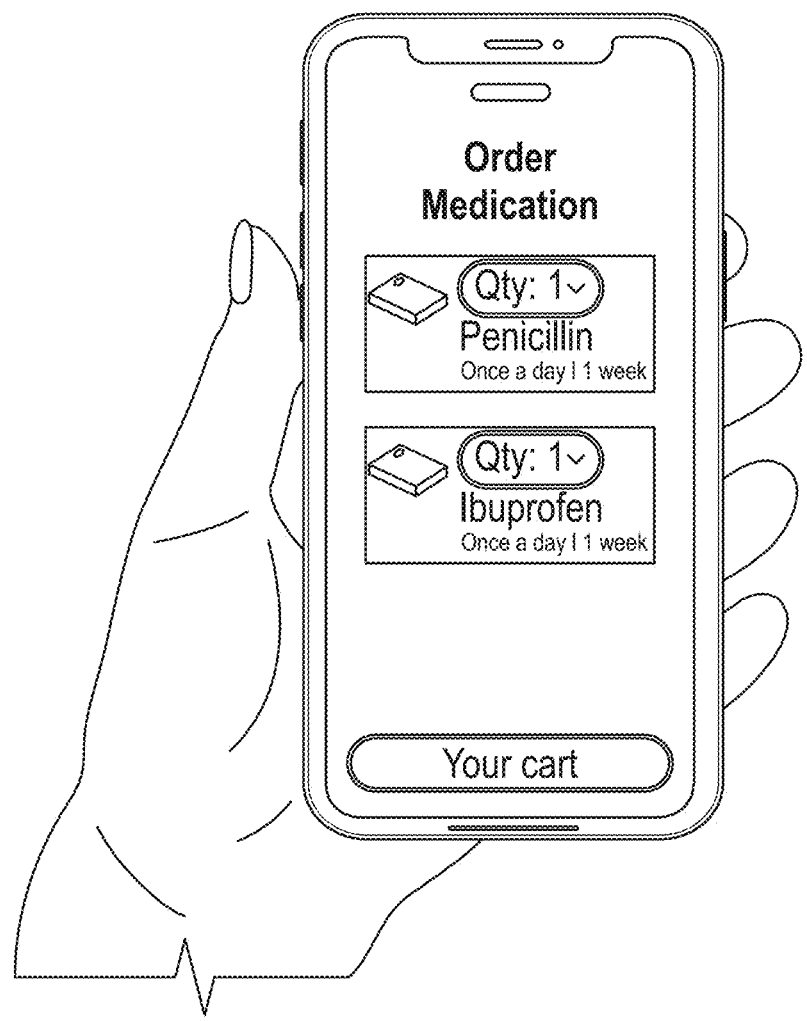
FIGS. 17A and 17B illustrate examples of screen displays and graphical user interfaces that may be displayed to a user on a user device, such as a mobile phone, to facilitate ordering of prescription medication and tracking of delivery of the prescription medication according to some embodiments described herein.

At Block 1510, the user is provided with a graphical user interface on a display screen of a user device (e.g., smart phone, laptop, tablet, smartwatch) that allows the user to initiate ordering of a prescription medication for treating the medical condition correlated to the test result obtained using the at-home diagnostic test kit 115. For example, the graphical user interface may include user-selectable graphics or text links (e.g., buttons) to facilitate ordering, such as shown in FIG. 17A.

At Block 1515, a prescription order request is received from a user (e.g., via input data received from the user-selectable graphics or text links (e.g., buttons) of the graphical user interface on the user device (e.g., smartphone or tablet)). At Block 1520, medical history information may be collected from the user to facilitate screening to be performed by a pharmacy provider or prescription medication fulfillment center.

At Block 1520, the remote health testing and diagnostic platform may coordinate fulfillment and delivery of requested prescription medication to the user and may coordinate payment from the user to the pharmacy or other prescription medication provider.

Figure 16:
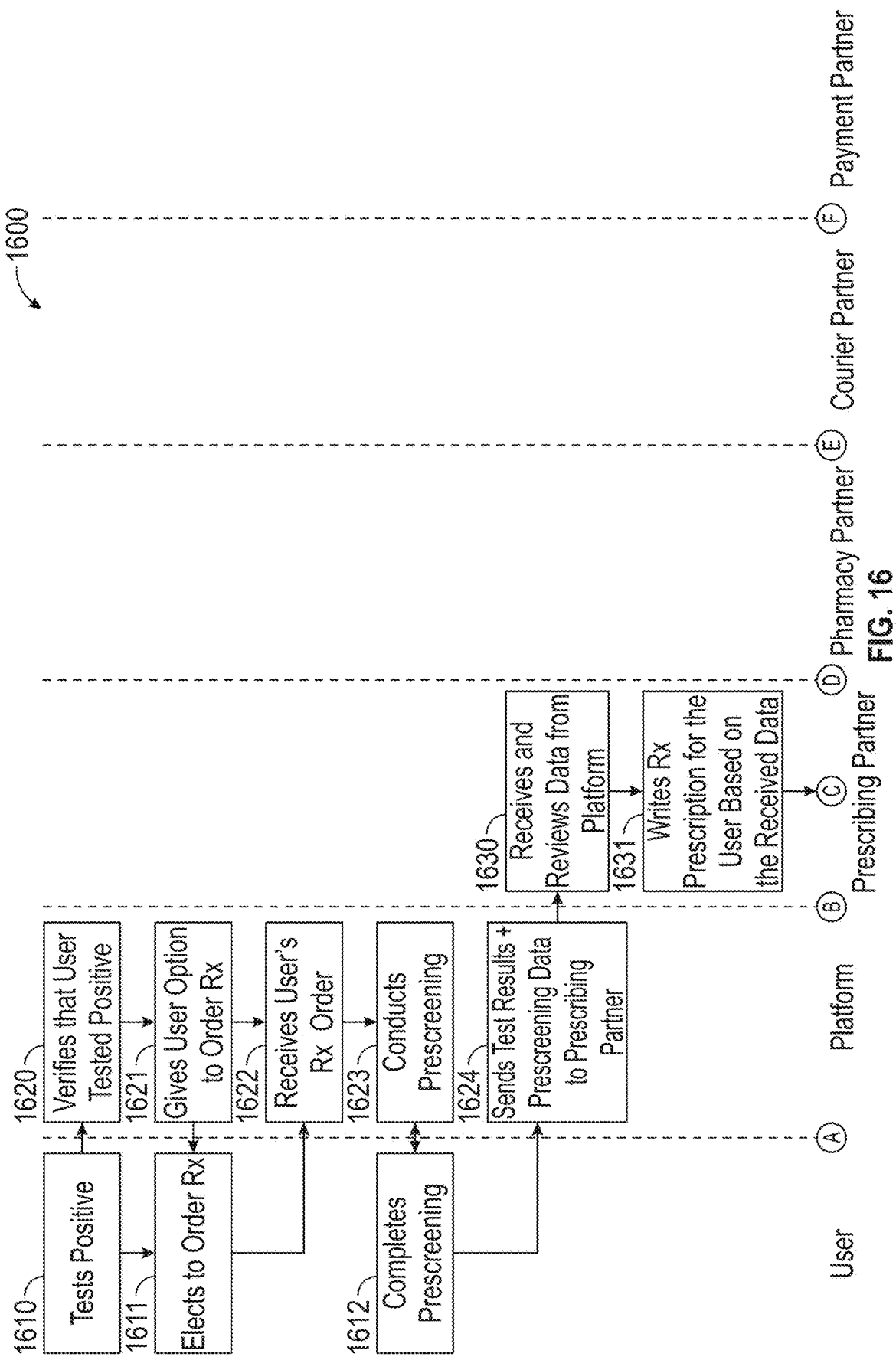
FIG. 16 illustrates an example flowchart of a method for facilitating ordering, fulfillment, and or delivery of prescription medication, with steps broken down by the entity performing the steps according to some embodiments described herein.
Figure 16:
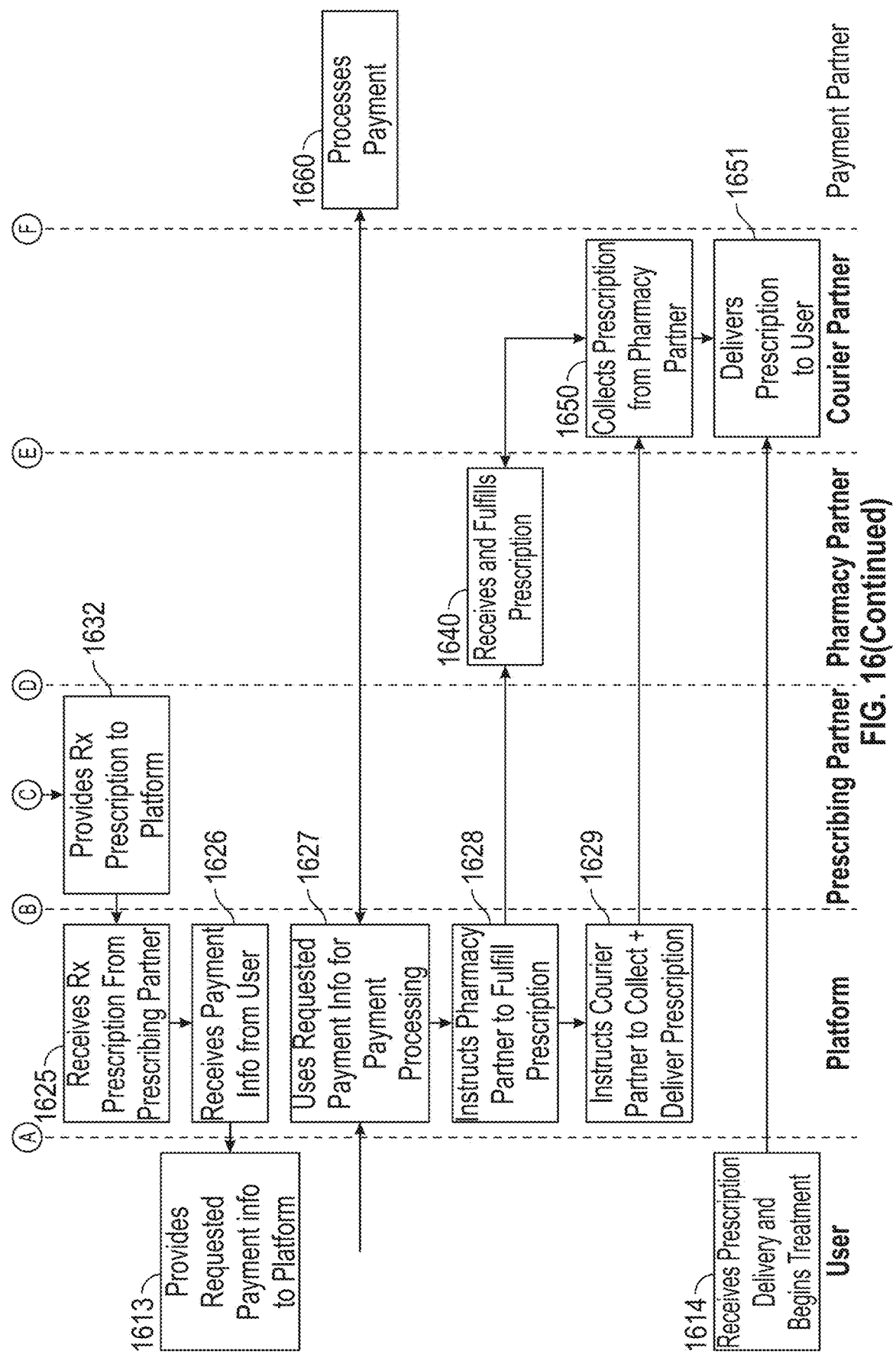

FIG. 16 illustrates an example flowchart of a method 1600 for facilitating ordering, fulfillment, and or delivery of prescription medication, with steps broken down by the entity performing the steps according to some embodiments described herein.

In some implementations, the entirety of the method 1600 can be performed in under an hour (e.g., between 30 minutes and 60 minutes, between 20 minutes and 45 minutes, between 10 minutes and 30 minutes, or overlapping ranges thereof). In some implementations, the methods disclosed herein can enable a user to receive a diagnosis and treatment for a health condition in an easy, rapid, safe, and affordable manner.

At Block 1610, a user who is interacting with the remote health testing and diagnostic platform (e.g., platform 1902 shown in FIG. 19) through a user device 110 (e.g., smartphone, tablet, laptop, etc.) for the purposes of taking a diagnostic test for a given medical condition (e.g., COVID-19, influenza A/B, UTI, strep throat, etc.) has tested positive for the given health condition (e.g., as indicated by diagnostic testing materials such as diagnostic test kits 115).

At Block 1620, the remote health testing and diagnostic platform verifies that the user has tested positive for the given medical condition. For instance, a live proctor may observe (e.g., by way of a camera on the user device 110) the diagnostic test that was taken by the user to interpret the test results, and may further verify that the test was taken correctly and therefore that the results yielded are valid. In some implementations, verification may include review of a virtual test pass or digital health pass (e.g., test pass 980) by the prescriber partner or pharmacy partner.

At Block 1621, the remote health testing platform provides the user with an opportunity to order prescription medication for treating the given medical condition (e.g., by way of a prompt presented to the user through a graphical user interface displayed on the user device 110 or through an electronic mail notification or text message notification via a telecommunications network). An example of a graphical user interface or e-commerce portal that may be provided for the user at this juncture is depicted in FIG. 17A.

At Block 1611, the user elects to order prescription medication for treating the given medical condition and, at Block 1622, the remote health testing and diagnostic platform receives user input data indicative of the user's decision to do so.

At block 1623, the remote health testing and diagnostic platform directs the user to a prescreening test for the prescription treatment that they will receive. For instance, in some examples, at this juncture the remote health testing and diagnostic platform may present the user with one or more questions to obtain information regarding whether the user has any known allergies to medications and/or any other information that may be of pertinence or relevance in the prescription fulfillment process, such as described in connection with FIG. 3E.

At Block 1612, the user completes the prescreening process (e.g., finishes submitting answers to questions posed by the remote health testing platform). At Block 1624, the remote health testing and diagnostic platform sends data including (i) data indicating the user's test results and (ii) data indicating the results of the user's prescreening to a prescriber partner. For example, the data indicating the user's test results may include images of the user's diagnostic testing materials, information supplied by the proctor, or a combination thereof. In some examples, the remote health testing and diagnostic platform also sends additional information about the user (e.g., name, date of birth, location, medical history, etc.) to the prescriber partner at this juncture. The data may include a digital health pass or test completion pass (e.g., test pass 980 described above)

At Block 1630, the prescriber partner receives and reviews the data associated with the user as sent by the remote health testing and diagnostic platform. At Block 1631, a licensed healthcare professional associated with the prescriber partner may write a prescription for treating the user's condition based on a review of the data sent by the remote health testing platform. For instance, if the licensed healthcare professional determines that the data provided by the remote health testing and diagnostic platform indicates that the user has the flu, then the licensed healthcare professional may write the user a prescription for Tamiflu. Similarly, a determination that the user has strep throat may lead the licensed healthcare professional to write the user a prescription for Amoxicillin, and a determination that the user has a UTI may lead the licensed healthcare professional to write the user a prescription for Cipro. In some examples, the licensed healthcare professional may write prescriptions for different medications based on any of a variety of factors including the user's allergies, possible interactions with other medications the user is taking, the availability of certain medications, and the like.

At Block 1632, the prescriber partner provides the prescription to the remote health testing and diagnostic platform, which in turn receives the prescription from the prescriber partner at Block 1625. In some implementations, the user may be connected with or given the option to connect with a licensed healthcare professional or other medical professional (e.g., via a remote telehealth appointment) at one or more points in the method 1600 as described above to receive guidance, medical advice, and the like.

At Block 1626, the remote health testing and diagnostic platform requests payment information from the user. At Block 1613, the user provides the requested payment information to the remote health testing and diagnostic platform. In some implementations, the payment information provided by the user at Block 1613 may include information regarding the user's credit or debit card, payment preferences, insurance information, and the like.

At Block 1627, the remote health testing and diagnostic platform uses the payment information received from the user for payment processing. In some implementations, one or more of the operations of Block 1627 are performed in coordination with a payment partner that processes payment for the fulfilment of the user's prescription at Block 1660.

In some embodiments, some or all of steps of Blocks 1613, 1626, 1627, and 1660 may be performed at different points in time and/or in a different order.

At Block 1628, the remote health testing and diagnostic platform instructs a pharmacy partner (e.g., Walgreens, CVS, Target, etc.) to fulfill the prescription for treating the user's condition. At Block 1629, the remote health testing and diagnostic platform instructs a courier partner (e.g., Uber) to collect the user's prescription medication as fulfilled by the pharmacy partner and deliver said prescription directly to the user. The courier partner may be affiliated with the pharmacy partner or may be unaffiliated with the pharmacy partner.

Figure 17B:
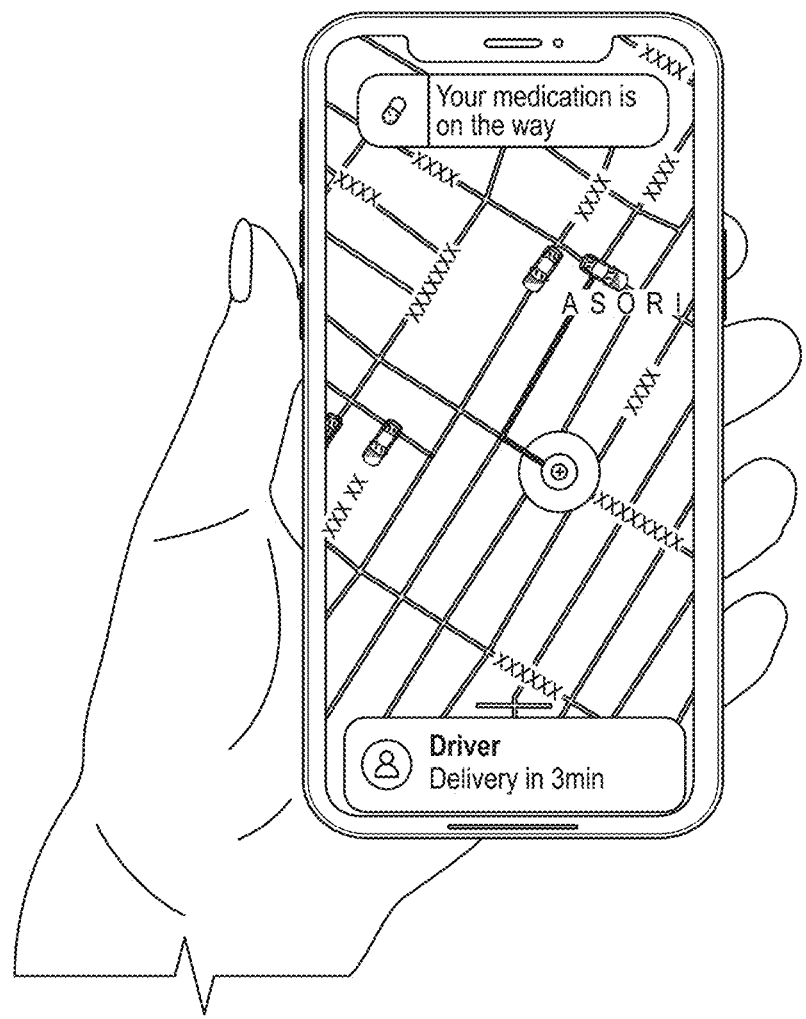

At Block 1640, the pharmacy partner fulfills the prescription for treating the user's condition. At Block 1650, the courier partner collects the prescription as fulfilled by the pharmacy partner. At Block 1651, the courier partner delivers the prescription directly to the user and, at Block 1614, the user receives the delivered prescription and begins treating their medical condition. In some implementations, the user may be provided with information regarding the status of the delivery, expected time of arrival, and/or the current location of the courier through an interface similar to that which is depicted in FIG. 17B. In some implementations, users may have the option to have test kit orders and/or prescription drug orders delivered to them via a shipping service or a courier service for rapid same day delivery.

FIGS. 17A and 17B illustrate examples of screen displays and graphical user interfaces that may be displayed to a user on a portable computing device (e.g., smartphone or tablet) to facilitate ordering of prescription medication and tracking of delivery of the prescription medication according to some embodiments described herein.

In some implementations, one or more of the exchanges between the user and the remote health testing and diagnostic platform as described above with reference to FIGS. 16, 17A and 17B may be made through and/or facilitated by an inline frame or "iFrame" HTML element of a web site or web application. In at least some of these implementations, the website or web application may be hosted by an entity other than that which maintains the remote health testing and diagnostic platform, such as a pharmacy, courier, or e-commerce business. Such an iFrame may effectively enable a website, web application, or components thereof that are hosted by the entity that maintains the testing platform to be embedded in the website or web application that is hosted by this other entity. In this way, users of the website or web application hosted by another entity, e.g., a pharmacy or e-commerce business, can quickly and seamlessly connect with the testing platform to order test kits, among other things. In some cases, test kit orders and/or prescription drug orders may be fulfilled at least in part by the other entity. For instance, if the other entity is a pharmacy, then test kit orders and/or prescription drug orders may be made available to users for pickup at their nearest pharmacy branch. Similarly, if the other entity is an e-commerce business, then test kit orders and/or prescription drug orders may be delivered to users by leveraging the business's existing supply chain and logistics infrastructure.

As an example, the website for "Duncan's Pharmacy" may include an iFrame element that enables users of the website to interface with the entity that maintains the testing platform without having to manually navigate away from and/or back to the Duncan's Pharmacy website.

Computer Systems

Figure 18:
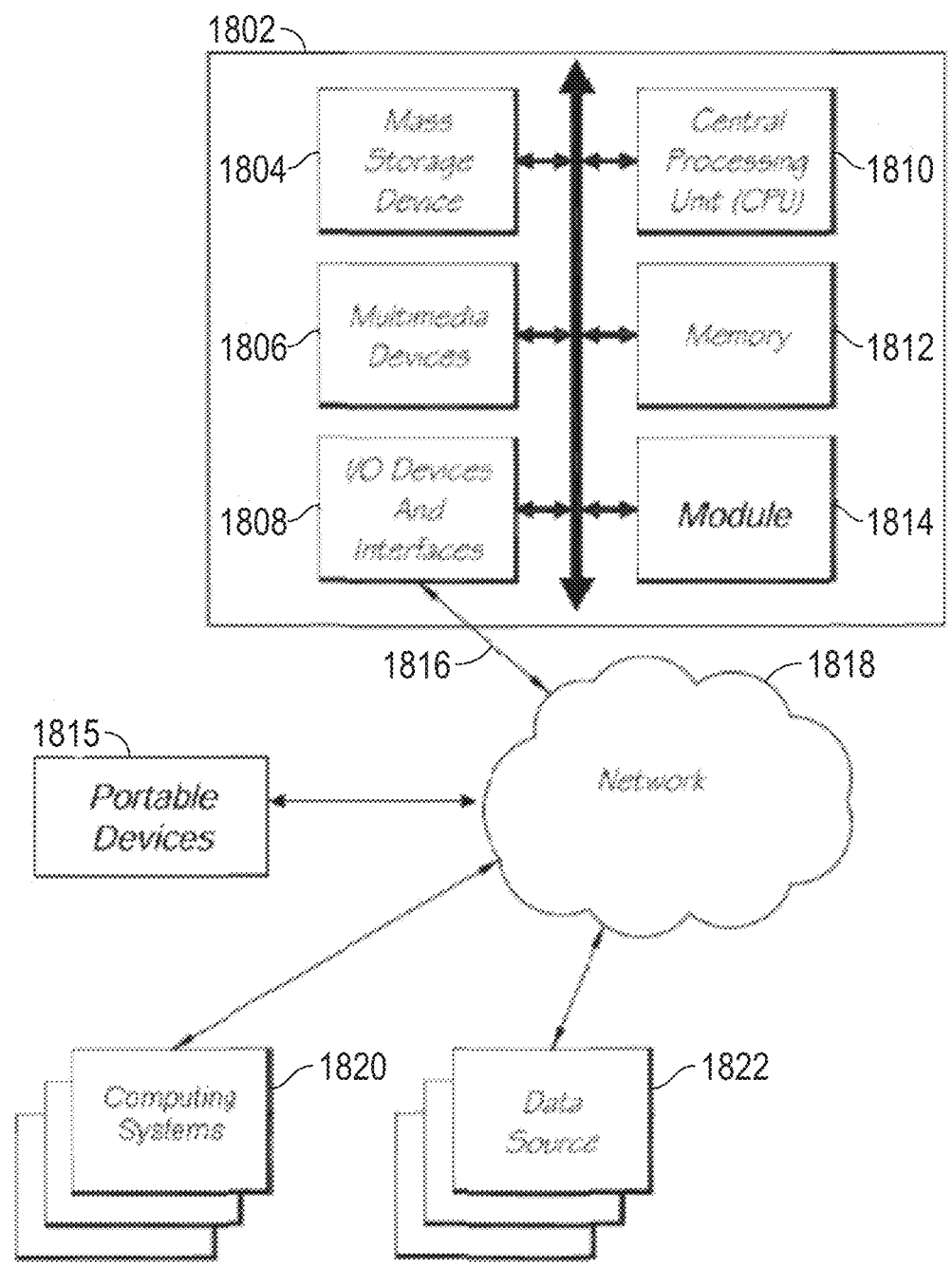
FIG. 18 is a block diagram illustrating an example embodiment of a computer system configured to run software for implementing one or more embodiments of the systems, methods, and devices disclosed herein.

FIG. 18 is a block diagram depicting an embodiment of a computer hardware system 1800 configured to run software for implementing one or more embodiments of the health testing and diagnostic systems, methods, and devices disclosed herein.

In some embodiments, the systems, processes, and methods described herein are implemented using a computing system, such as the one illustrated in FIG. 18. The example computer system 1802 is in communication with one or more computing systems 1820 and/or one or more data sources 1822 via one or more networks 1818. While FIG. 18 illustrates an embodiment of a computing system 1802, it is recognized that the functionality provided for in the components and modules of computer system 1802 may be combined into fewer components and modules, or further separated into additional components and modules.

The computer system 1802 can comprise a health testing and diagnostic module 1814 that carries out the functions, methods, acts, and/or processes described herein (e.g., via health testing and diagnostic platform 1902 shown in FIG.

19). The health testing and diagnostic module 1814 is executed on the computer system 1802 by a central processing unit 1806 discussed further below.

In general, the word "module," as used herein, refers to logic embodied in hardware or firmware or to a collection of software instructions, having entry and exit points. Modules are written in a program language, such as JAVA, C or C++, PYPHON or the like. Software modules may be compiled or linked into an executable program, installed in a dynamic link library, or may be written in an interpreted language such as BASIC, PERL, LUA, or Python. Software modules may be called from other modules or from themselves, and/or may be invoked in response to detected events or interruptions. Modules implemented in hardware include connected logic units such as gates and flip-flops, and/or may include programmable units, such as programmable gate arrays or processors.

Generally, the modules described herein refer to logical modules that may be combined with other modules or divided into sub-modules despite their physical organization or storage. The modules are executed by one or more computing systems and may be stored on or within any suitable computer readable medium or implemented in-whole or in-part within special designed hardware or firmware. Not all calculations, analysis, and/or optimization require the use of computer systems, though any of the above-described methods, calculations, processes, or analyses may be facilitated through the use of computers. Further, in some embodiments, process blocks described herein may be altered, rearranged, combined, and/or omitted.

The computer system 1802 includes one or more processing units (CPU) 1806, which may comprise a microprocessor. The computer system 1802 further includes a physical memory 1810, such as random access memory (RAM) for temporary storage of information, a read only memory (ROM) for permanent storage of information, and a mass storage device 1804, such as a backing store, hard drive, rotating magnetic disks, solid state disks (SSD), flash memory, phase-change memory (PCM), 3D XPoint memory, diskette, or optical media storage device. Alternatively, the mass storage device may be implemented in an array of servers. Typically, the components of the computer system 1802 are connected to the computer using a standards-based bus system. The bus system can be implemented using various protocols, such as Peripheral Component Interconnect (PCI), Micro Channel, SCSI, Industrial Standard Architecture (ISA) and Extended ISA (EISA) architectures.

The computer system 1802 includes one or more input/output (I/O) devices and interfaces 1812, such as a keyboard, mouse, touch pad, and printer. The I/O devices and interfaces 1812 can include one or more display devices, such as a monitor, that allows the visual presentation of data to a user. More particularly, a display device provides for the presentation of GUIs as application software data, and multi-media presentations, for example. The I/O devices and interfaces 1812 can also provide a communications interface to various external devices. The computer system 1802 may comprise one or more multi-media devices 1808, such as speakers, video cards, graphics accelerators, and microphones, for example.

The computer system 1802 may run on a variety of computing devices, such as a server, a Windows server, a Structure Query Language server, a Unix Server, a personal computer, a laptop computer, and so forth. In other embodiments, the computer system 1802 may run on a cluster computer system, a mainframe computer system and/or other computing system suitable for controlling and/or communicating with large databases, performing high volume transaction processing, and generating reports from large databases. The computing system 1802 is generally controlled and coordinated by an operating system software, such as z/OS, Windows, Linux, UNIX, BSD, SunOS, Solaris, MacOS, or other compatible operating systems, including proprietary operating systems. Operating systems control and schedule computer processes for execution, perform memory management, provide file system, networking, and I/O services, and provide a user interface, such as a graphical user interface (GUI), among other things.

The computer system 1802 illustrated in FIG. 18 is coupled to a network 1818, such as a LAN, WAN, or the Internet via a communication link 1816 (wired, wireless, or a combination thereof). Network 1818 communicates with various computing devices and/or other electronic devices. Network 1818 is communicating with one or more computing systems 1820 and one or more data sources 1822. The health testing and diagnostic module 1814 may access or may be accessed by computing systems 1820 and/or data sources 1822 through a web-enabled user access point. Connections may be a direct physical connection, a virtual connection, and other connection type. The web-enabled user access point may comprise a browser module that uses text, graphics, audio, video, and other media to present data and to allow interaction with data via the network 1818.

Access to the health testing and diagnostic module 1814 of the computer system 1802 by computing systems 1820 and/or by data sources 1822 may be through a web-enabled user access point such as the computing systems' 1820 or data source's 1822 personal computer, cellular phone, smartphone, laptop, tablet computer, e-reader device, audio player, or another device capable of connecting to the network 1818. Such a device may have a browser module that is implemented as a module that uses text, graphics, audio, video, and other media to present data and to allow interaction with data via the network 1818.

The output module may be implemented as a combination of an all-points addressable display such as a cathode ray tube (CRT), a liquid crystal display (LCD), a plasma display, or other types and/or combinations of displays. The output module may be implemented to communicate with input devices 1812 and they also include software with the appropriate interfaces which allow a user to access data through the use of stylized screen elements, such as menus, windows, dialogue boxes, tool bars, and controls (for example, radio buttons, check boxes, sliding scales, and so forth). Furthermore, the output module may communicate with a set of input and output devices to receive signals from the user.

The input device(s) may comprise a keyboard, roller ball, pen and stylus, mouse, trackball, voice recognition system, or pre-designated switches or buttons. The output device(s) may comprise a speaker, a display screen, a printer, or a voice synthesizer. In addition, a touch screen may act as a hybrid input/output device. In another embodiment, a user may interact with the system more directly such as through a system terminal connected to the score generator without communications over the Internet, a WAN, or LAN, or similar network.

In some embodiments, the system 1802 may comprise a physical or logical connection established between a remote microprocessor and a mainframe host computer for the express purpose of uploading, downloading, or viewing interactive data and databases on-line in real time. The remote microprocessor may be operated by an entity operating the computer system 1802, including the client server systems or the main server system, an/or may be operated by one or more of the data sources 1822 and/or one or more of the computing systems 1820. In some embodiments, terminal emulation software may be used on the microprocessor for participating in the micro-mainframe link.

In some embodiments, computing systems 1820 who are internal to an entity operating the computer system 1802 may access the health testing and diagnostic module 1814 internally as an application or process run by the CPU 1806.

In some embodiments, one or more features of the systems, methods, and devices described herein can utilize a URL and/or cookies, for example for storing and/or transmitting data or user information. A Uniform Resource Locator (URL) can include a web address and/or a reference to a web resource that is stored on a database and/or a server. The URL can specify the location of the resource on a computer and/or a computer network. The URL can include a mechanism to retrieve the network resource. The source of the network resource can receive a URL, identify the location of the web resource, and transmit the web resource back to the requestor. A URL can be converted to an IP address, and a Domain Name System (DNS) can look up the URL and its corresponding IP address. URLs can be references to web pages, file transfers, emails, database accesses, and other applications. The URLs can include a sequence of characters that identify a path, domain name, a file extension, a host name, a query, a fragment, scheme, a protocol identifier, a port number, a username, a password, a flag, an object, a resource name and/or the like. The systems disclosed herein can generate, receive, transmit, apply, parse, serialize, render, and/or perform an action on a URL.

A cookie, also referred to as an HTTP cookie, a web cookie, an internet cookie, and a browser cookie, can include data sent from a website and/or stored on a user's computer. This data can be stored by a user's web browser while the user is browsing. The cookies can include useful information for websites to remember prior browsing information, such as a shopping cart on an online store, clicking of buttons, login information, and/or records of web pages or network resources visited in the past. Cookies can also include information that the user enters, such as names, addresses, passwords, credit card information, etc. Cookies can also perform computer functions. For example, authentication cookies can be used by applications (for example, a web browser) to identify whether the user is already logged in (for example, to a web site). The cookie data can be encrypted to provide security for the consumer. Tracking cookies can be used to compile historical browsing histories of individuals. Systems disclosed herein can generate and use cookies to access data of an individual. Systems can also generate and use JSON web tokens to store authenticity information, HTTP authentication as authentication protocols, IP addresses to track session or identity information, URLs, and the like.

The computing system 1802 may include one or more internal and/or external data sources (for example, data sources 1822). In some embodiments, one or more of the data repositories and the data sources described above may be implemented using a relational database, such as DB2, Sybase, Oracle, CodeBase, and Microsoft® SQL Server as well as other types of databases such as a flat-file database, an entity relationship database, and object-oriented database, and/or a record-based database.

The computer system 1802 may also access one or more databases 1822. The databases 1822 may be stored in a database or data repository. The computer system 1802 may access the one or more databases 1822 through a network 1818 or may directly access the database or data repository through I/O devices and interfaces 1812. The data repository storing the one or more databases 1822 may reside within the computer system 1802.

FIG. 19 is a block diagram illustrating an example embodiment of a computer system configured to run software for implementing one or more embodiments of the health testing and diagnostic systems, methods, and devices disclosed herein. In some embodiments, the various systems, methods, and devices described herein may also be implemented in decentralized systems such as, for example, blockchain applications. For example, blockchain technology may be used to maintain user profiles, proctor profiles, test results, test site databases, and/or financing databases or ledgers, dynamically generate, execute, and record testing plan agreements, perform searches, coordinate inventory tracking and reordering of medical diagnostic test kits, coordinate generation of virtual test completion passes, coordinate augmented reality content display, conduct patient-proctor matching, determine pricing, coordinate prescription medication order, fulfillment, and delivery, and conduct any other functionalities described herein.

In some embodiments, a remote health testing and diagnostic platform 1902 may be comprised of a registration and purchase module 1904, a testing module 1906, an analytics module 1908, and a reporting module 1910. The health testing and diagnostic platform 1902 may also comprise a user profile database 1912, a proctor database 1914, a test database 1916, and/or a site database 1918. The health testing and diagnostic platform 1902 can be connected to a network 1920. The network 1920 can be configured to connect the health testing and diagnostic platform 1902 to one or more proctor devices 1922, one or more user devices 1924, one or more pharmacy systems 1926, one or more third-party provider systems 1928 (e.g., payment providers, prescriber providers, courier service providers), and/or one or more government systems 1930.

The registration and purchase 1904 may function by facilitating patient registration through one or more registration interfaces and in conjunction with the user database 1912, store user registration data. The testing module 1906 may be configured to allow a user to initiate and complete a medical test or visit with a proctor through a series of pre-testing and testing interfaces, as described herein. The analytics module 1908 may be configured to dynamically analyze patient tests across a given population stored in the test database 1916 and provide structured data of the test results. The reporting module 1910 may function by dynamically and automatically reporting test results to government entities, patients, and third parties using one or more interfaces, such as one or more application programming interfaces. Each of the modules can be configured to interact with each other and the databases discussed herein.

Additional Embodiments

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than restrictive sense.

Indeed, although this invention has been disclosed in the context of certain embodiments and examples, it will be understood by those skilled in the art that the invention extends beyond the specifically disclosed embodiments to other alternative embodiments and/or uses of the invention and obvious modifications and equivalents thereof. In addition, while several variations of the embodiments of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the embodiments of the disclosed invention. Any methods disclosed herein need not be performed in the order recited. Thus, it is intended that the scope of the invention herein disclosed should not be limited by the particular embodiments described above.

It will be appreciated that the systems and methods of the disclosure each have several innovative aspects, no single one of which is solely responsible or required for the desirable attributes disclosed herein. The various features and processes described above may be used independently of one another or may be combined in various ways. All possible combinations and subcombinations are intended to fall within the scope of this disclosure.

Certain features that are described in this specification in the context of separate embodiments also may be implemented in combination in a single embodiment. Conversely, various features that are described in the context of a single embodiment also may be implemented in multiple embodiments separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination. No single feature or group of features is necessary or indispensable to each and every embodiment.

It will also be appreciated that conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. In addition, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise. Similarly, while operations may be depicted in the drawings in a particular order, it is to be recognized that such operations need not be performed in the particular order shown or in sequential order, or that all illustrated operations be performed, to achieve desirable results. Further, the drawings may schematically depict one more example processes in the form of a flowchart. However, other operations that are not depicted may be incorporated in the example methods and processes that are schematically illustrated. For example, one or more additional operations may be performed before, after, simultaneously, or between any of the illustrated operations. Additionally, the operations may be rearranged or reordered in other embodiments. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products. Additionally, other embodiments are within the scope of the following claims. In some cases, the actions recited in the claims may be performed in a different order and still achieve desirable results.

Further, while the methods and devices described herein may be susceptible to various modifications and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various implementations described and the appended claims. Further, the disclosure herein of any particular feature, aspect, method, property, characteristic, quality, attribute, element, or the like in connection with an implementation or embodiment can be used in all other implementations or embodiments set forth herein. Any methods disclosed herein need not be performed in the order recited. The methods disclosed herein may include certain actions taken by a practitioner; however, the methods can also include any third-party instruction of those actions, either expressly or by implication. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 3.5 mm" includes "3.5 mm." Phrases preceded by a term such as "substantially" include the recited phrase and should be interpreted based on the circumstances (e.g., as much as reasonably possible under the circumstances). For example, "substantially constant" includes "constant." Unless stated otherwise, all measurements are at standard conditions including temperature and pressure.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y, and at least one of Z to each be present. The headings provided herein, if any, are for convenience only and do not necessarily affect the scope or meaning of the devices and methods disclosed herein.

Accordingly, the claims are not intended to be limited to the embodiments shown herein, but are to be accorded the widest scope consistent with this disclosure, the principles and the novel features disclosed herein.

What is claimed is:

1. A computer-implemented system for a proctored examination platform for a medical diagnostic test, the computer-implemented system comprising:
    an electronic storage medium of a computing system, the electronic storage medium comprising computer-executable instructions;
    one or more processors of the computing system, the one or more processors in electronic communication with the electronic storage medium, the one or more processors in electronic communication through an electronic network with a user computing device, the one or more processors configured to execute the computer-executable instructions stored in the electronic storage medium for implementing the proctored examination platform for the medical diagnostic test by:
        receiving, by the computing system through an electronic network, a user request from the user computing device for a proctored examination for a medical diagnostic test, wherein the medical diagnostic test is provided in a medical diagnostic test kit container, wherein the medical diagnostic test kit container comprises a machine-readable code configured to be imaged by a camera of the user computing device to enable:
            providing a fiducial point from which a coordinate frame for an augmented reality presentation can be established using the camera and a display of the user computing device; and
            causing the user computing device to display a user selectable graphic on the display of the user computing device that, when selected by a user, causes a software application stored on the user computing device to access the computing system for initiation of the augmented reality presentation that includes display of augmented reality content relating to the medical diagnostic test provided in the medical diagnostic test kit container,
        wherein the medical diagnostic test kit container comprises equipment to perform the medical diagnostic test;
        generating, by the computing system, first proctor display data for displaying a graphical user interface (GUI) on a display of a proctor device, the first proctor display data configured to display to a proctor a phase of the medical diagnostic test;
        transmitting, by the computing system through the electronic network, the first proctor display data to the proctor device;
        receiving, by the computing system, through the electronic network, a first video conference connection request from the proctor device,
        establishing, by the computing system, a first electronic video conference session between the proctor device and the user computing device;
        receiving, by the computing system through the electronic network, video frame data associated with the medical diagnostic test;
        receiving, by the computing system through the electronic network, a request to order prescription drugs from the user computing device, wherein the request to order the prescription drugs is based on a verified positive test result from the user taking the medical diagnostic test, and wherein the verified positive test result is based on the computing system dynamically verifying that the medical diagnostic test was administered by the user without abnormalities by analyzing the received video frame data to automatically determine that a test card associated with the medical diagnostic test remains undisturbed during a predetermined dwell time associated with the medical diagnostic test;
        causing the computing system to transmit the verified positive test result to a third party;
        transmitting, by the computing system through the electronic network, a prescription for the prescription drugs to a pharmacy device.

2. The computer-implemented system of claim 1, wherein the computing system comprises one or more computing systems.

3. The computer-implemented system of claim 1, wherein the machine-readable code is a QR code.

4. The computer-implemented system of claim 1, wherein the machine-readable code is a QR code printed on an external surface of the medical diagnostic test kit container.

5. The computer-implemented system of claim 1, wherein the machine-readable code is a QR code printed on an adhesive sticker adhered to an external surface of the medical diagnostic test kit container.

6. The computer-implemented system of claim 1, wherein the machine-readable code is an augmented reality QR code.

7. The computer-implemented system of claim 1, wherein the machine-readable code is located on an external surface of the equipment to perform the medical diagnostic test.

8. The computer-implemented system of claim 1, wherein the augmented reality content comprises an identification of the equipment to perform the medical diagnostic test.

9. The computer-implemented system of claim 1, wherein the augmented reality content comprises instructions for using the equipment to perform the medical diagnostic test.

10. The computer-implemented system of claim 1, wherein the augmented reality content comprises a test accuracy of the medical diagnostic test.

11. The computer-implemented system of claim 1, wherein the augmented reality content comprises a time to result of the medical diagnostic test.

12. A computer-implemented method performed by a computing system of a proctored examination platform for a medical diagnostic test, the computer-implemented method comprising:
    receiving, through an electronic network, a user request from a user for a proctored examination for a medical diagnostic test, wherein the medical diagnostic test is provided in a medical diagnostic test kit container, the medical diagnostic test kit container comprises a machine-readable code configured to be imaged by a camera of a user computing device to enable:
        providing a fiducial point from which a coordinate frame for an augmented reality presentation can be established using the camera and display of the user computing device; and
        causing the user computing device to display a user selectable graphic on the display of the user computing device that, when selected by the user, causes a software application stored on the user computing device to access the computing system for initiation of the augmented reality presentation that includes display of augmented reality content relating to the medical diagnostic test provided in the medical diagnostic test kit container, wherein the medical diagnostic test kit container comprises equipment to perform the medical diagnostic test;

generating first proctor display data for displaying a graphical user interface (GUI) on a display of a proctor device, the first proctor display data configured to display to a proctor a phase of the medical diagnostic test;

transmitting, through the electronic network, a first video conference connection request to the proctor device;

receiving, through the electronic network, a first video conference connection request from the proctor device;

establishing a first electronic video conference session between the proctor device and the user computing device;

receiving, through the electronic network, video frame data associated with the medical diagnostic test;

receiving, through the electronic network, a request to order prescription drugs from the user computing device, wherein the request to order the prescription drugs is based on a verified positive test result from the user taking the medical diagnostic test, and wherein the verified positive test result is based on dynamically verifying that the medical diagnostic test was administered by the user without abnormalities by analyzing the received video frame data to automatically determine that a test card associated with the medical diagnostic test remains undisturbed during a predetermined dwell time associated with the medical diagnostic test;

transmitting the verified positive test result to a third party; and transmitting, through the electronic network, a prescription for the prescription drugs to a pharmacy device, wherein the computing system comprises one or more processors and an electronic memory.

13. The computer-implemented method of claim 12, wherein the machine-readable code is a QR code.

14. The computer-implemented method of claim 12, wherein the machine-readable code is a QR code printed on an external surface of the medical diagnostic test kit container.

15. The computer-implemented method of claim 12, wherein the machine-readable code is an augmented reality QR code.

16. The computer-implemented method of claim 12, wherein the machine-readable code is located on an external surface of the equipment to perform the medical diagnostic test.

17. The computer-implemented method of claim 12, wherein the augmented reality content comprises an identification of the equipment to perform the medical diagnostic test.

18. The computer-implemented method of claim 12, wherein the augmented reality content comprises instructions for using the equipment to perform the medical diagnostic test.

19. The computer-implemented method of claim 12, wherein the augmented reality content comprises a test accuracy of the medical diagnostic test.

20. The computer-implemented method of claim 12, wherein the augmented reality content comprises a time to result of the medical diagnostic test.

* * * * *